US010472362B2

(12) United States Patent
Jackson et al.

(10) Patent No.: US 10,472,362 B2
(45) Date of Patent: Nov. 12, 2019

(54) FUSED TRICYCLIC IMIDAZO PYRAZINES AS MODULATORS OF TNF ACTIVITY

(71) Applicant: UCB Biopharma SPRL, Brussels (BE)

(72) Inventors: Victoria Elizabeth Jackson, Slough (GB); Jag Paul Heer, Slough (GB); Uwe Heinelt, Frankfurt am Main (DE)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

(21) Appl. No.: 15/580,137

(22) PCT Filed: Jun. 7, 2016

(86) PCT No.: PCT/EP2016/062898
§ 371 (c)(1),
(2) Date: Dec. 6, 2017

(87) PCT Pub. No.: WO2016/198398
PCT Pub. Date: Dec. 15, 2016

(65) Prior Publication Data
US 2018/0298006 A1 Oct. 18, 2018

(30) Foreign Application Priority Data
Jun. 8, 2015 (GB) .................. 1509888.2

(51) Int. Cl.
C07D 487/04 (2006.01)
C07D 491/147 (2006.01)
C07D 491/04 (2006.01)

(52) U.S. Cl.
CPC .......... *C07D 487/04* (2013.01); *C07D 491/04* (2013.01); *C07D 491/147* (2013.01)

(58) Field of Classification Search
CPC .................. C07D 487/04; C07D 491/147
See application file for complete search history.

(56) References Cited

U.S. PATENT DOCUMENTS

2011/0183928 A1 7/2011 Thede et al.

FOREIGN PATENT DOCUMENTS

| WO | 2009/156091 A1 | 12/2009 |
|---|---|---|
| WO | 2013/186229 A1 | 12/2013 |
| WO | 2014/009295 A1 | 1/2014 |
| WO | 2014/009296 A1 | 1/2014 |
| WO | 2015/086525 A1 | 6/2015 |
| WO | 2015/086526 A1 | 6/2015 |
| WO | 2015/086527 A1 | 6/2015 |
| WO | 2016/177690 A1 | 11/2016 |

OTHER PUBLICATIONS

Tansey et al., "The TNF superfamily in 2009: new pathways, new indications, and new drugs", Drug Discovery Today, 2009, 14(23/24), 1082-1088.
Carneiro et al., "Emerging Role for TNF-alpha in Erectile Dysfunction", Journal of Sexual Medicine, 2010, vol. 7, 3823-3834.
Wu et al., "Do TNF Inhibitors Reduce the Risk of Myocardial Infarction in Psoriasis Patients?", JAMA, 2013, 309(19), 2043-2044.
Hauwermeiren et al., "Safe TNF-based antitumor therapy following p55TNFR reduction in intestinal epithelium", The Journal of Clinical Investigation, 2013, 123(6), 2590-2603.
Nawrocka et al., "Immunotropic Properties of 2-Aminobenzimidazole Derivatives in Cultures of Human Peripheral Blood Cells, Part 5", Arch. Pharm. Pharm. Med. Chem., 1999, 85-90.

Primary Examiner — Karen Cheng
(74) Attorney, Agent, or Firm — McDonnell Boehnen Hulbert & Berghoff LLP

(57) ABSTRACT

A series of substituted fused tricyclic imidazo pyrazine derivatives and analoges thereof, represented by formula (I), being potent modulators of human TNFa activity, are accordingly of benefit in the treatment and/or prevention of various human ailments, including autoimmune and inflammatory disorders; neurological and neurodegenerative disorders; pain and nociceptive disorders; cardiovascular disorders; metabolic disorders; ocular disorders; and oncological disorders.

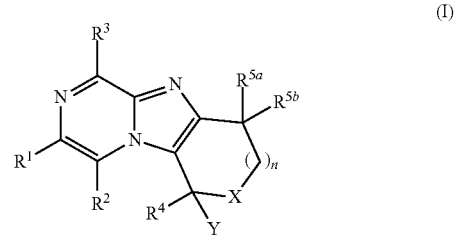

(I)

11 Claims, No Drawings

FUSED TRICYCLIC IMIDAZO PYRAZINES AS MODULATORS OF TNF ACTIVITY

This application is a U.S. national phase application under 35 USC 371 of International Patent Application no. PCT/EP2016/062898, filed Jun. 7, 2016, which claims the benefit of Great Britain Application no. 1509888.2, filed Jun. 8, 2015.

The present invention relates to a class of fused imidazole derivatives, and to their use in therapy. More particularly, this invention is concerned with pharmacologically active substituted fused tricyclic imidazo pyrazine derivatives and analogs thereof.

These compounds are modulators of the signalling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certolizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, *Drug Discovery Today*, 2009, 14, 1082-1088; and F. S. Carneiro et al., *J. Sexual Medicine*, 2010, 7, 3823-3834).

The compounds in accordance with the present invention, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, certain compounds of this invention may be useful for coupling to a fluorophore to provide fluorescent conjugates that can be utilised in assays (e.g. a fluorescence polarisation assay) for detecting pharmacologically active compounds.

International patent applications WO 2013/186229, WO 2014/009295 and WO 2014/009296 describe fused imidazole derivatives which are modulators of human TNFα activity.

International patent applications WO2015/086525 and WO2015/086526 published Jun. 18, 2015 relate to fused tricyclic imidazole derivatives which are modulators of the signalling of TNFα.

None of the prior art available to date, however, discloses or suggests the precise structural class of fused imidazo pyrazine derivatives as provided by the present invention.

The present invention provides a compound of formula (I) or an N-oxide thereof, or a pharmaceutically acceptable salt or solvate thereof, or a glucuronide derivative thereof, or a co-crystal thereof:

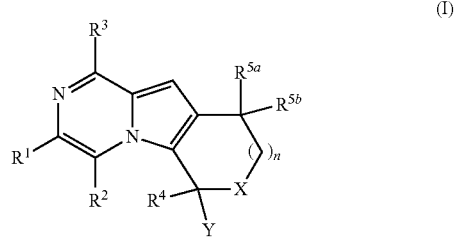

(I)

wherein n represents an integer equal to 0 or 1.

Y represents $C_{3-7}$ cycloalkyl, aryl, $C_{3-7}$ heterocycloalkyl or heteroaryl, any of which groups may be optionally substituted by one or more substituents;

X represents oxygen, sulphur, S(O), S(O)$_2$, S(O)(N—R$^d$), N(C(O)R$^d$), N(COOR$^d$), N(SO$_2$R$^d$), or N(R$^d$); or an optionally substituted straight or branched $C_{1-4}$ alkylene chain;

R$^1$ represents hydrogen, halogen, cyano, nitro, hydroxy, trifluoromethyl, trifluoromethoxy, —OR$^a$, —SR$^a$, —SOR$^a$, —SO$_2$R$^a$, —SF$_5$, —NR$^b$R$^c$, —NR$^c$COR$^d$, —NR$^c$CO$_2$R$^d$, —NHCONR$^b$R$^c$, —NR$^c$SO$_2$R$^e$, —N(SO$_2$R$^e$)$_2$, —NHSO$_2$NR$^b$R$^c$, —COR$^d$, —CO$_2$R$^d$, —CONR$^b$R$^c$, —CON(OR$^a$)R$^b$, —SO$_2$NR$^b$R$^c$, or —S(O)(N—R$^d$)R$^a$; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl($C_{1-6}$)alkyl, aryl, aryl($C_{1-6}$) alkyl, $C_{3-7}$ heterocycloalkyl, $C_{3-7}$ heterocycloalkyl($C_{1-6}$) alkyl, $C_{3-7}$ heterocycloalkenyl, $C_{4-9}$ heterobicycloalkyl, heteroaryl, heteroaryl($C_{1-6}$)alkyl, ($C_{3-7}$)heterocycloalkyl($C_{1-6}$) alkyl-aryl-, heteroaryl($C_{3-7}$)heterocycloalkyl-, ($C_{3-7}$) cycloalkyl-heteroaryl-, ($C_{3-7}$)cycloalkyl($C_{1-6}$)alkyl-heteroaryl-, ($C_{4-7}$)cycloalkenyl-heteroaryl-, ($C_{4-9}$) bicycloalkyl-heteroaryl-, ($C_{4-9}$)bicycloalkenyl-heteroaryl-, ($C_{3-7}$)heterocycloalkyl-heteroaryl-, ($C_{3-7}$)heterocycloalkyl ($C_{1-6}$)alkyl-heteroaryl-, ($C_{3-7}$)heterocycloalkenyl-heteroaryl-, ($C_{4-9}$)heterobicycloalkyl-heteroaryl-, heteroaryl-aryl- or ($C_{4-9}$)spiroheterocycloalkyl-heteroaryl-, any of which groups may be optionally substituted by one or more substituents;

R$^2$ and R$^3$ independently represent hydrogen, halogen, cyano, nitro, hydroxy, trifluoromethyl, trifluoromethoxy or —OR$^a$; or $C_{1-6}$ alkyl optionally substituted by one or more substituents;

R$^4$ represents hydrogen, hydroxy, halogen, trifluoromethyl, —NR$^b$R$^c$, —NR$^c$C(O)R$^d$, —(CO)—NR$^c$R$^d$, —NH—S(O)$_2$R$^e$, —S—R$^a$, —(SO)—R$^a$, —S(O)$_2$R$^a$, —S(O)(N—

$R^d)R^a$, —SO$_2$NR$^b$R$^c$, —OR$^a$, —C(O)—OR$^d$, or —O(CO)—R$^d$—; or C$_{1-6}$ alkyl, C$_{2-6}$ alkenyl, C$_{2-6}$ alkynyl, aryl, heteroaryl, any of which groups may be optionally substituted by one or more substituents; or R$^4$ and Y together with the carbon to which they are attached form a C$_{3-7}$ cycloalkyl or C$_{3-7}$ heterocycloalkyl, optionally substituted with one or more substituents;

R$^{5a}$ and R$^{5b}$ independently represent hydrogen, hydroxy, halogen, trifluoromethyl, cyano, —NR$^b$R$^c$, —NR$^c$C(O)R$^d$, —(CO)—NR$^c$R$^d$, —NH—S(O)$_2$R$^e$, —S—R$^a$, —(SO)—R$^a$, —S(O)$_2$R$^a$, —S(O)(N—R$^d$)R$^a$, —SO$_2$NR$^b$R$^c$, —OR$^a$, —C(O)—OR$^d$, or —O(CO)—R$^d$; or C$_{1-6}$ alkyl, C$_{2-6}$ alkenyl, C$_{2-6}$ alkynyl, aryl, heteroaryl, any of which groups may be optionally substituted by one or more substituents; or R$^{5a}$ and R$^{5b}$ when taken together with the carbon to which they are attached represent a carbonyl, thiocarbonyl or —C=N—OH; and R$^a$ represents C$_{1-6}$ alkyl, aryl, aryl(C$_{1-6}$)alkyl, C$_{3-7}$ cycloalkyl, C$_{3-7}$ heterocycloalkyl, heteroaryl or heteroaryl (C$_{1-6}$)alkyl, any of which groups may be optionally substituted by one or more substituents;

R$^b$ and R$^c$ independently represent hydrogen or trifluoromethyl; or C$_{1-6}$ alkyl, C$_{3-7}$ cycloalkyl, C$_{3-7}$ cycloalkyl (C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, heteroaryl or heteroaryl(C$_{1-6}$) alkyl, any of which groups may be optionally substituted by one or more substituents; or R$^b$ and R$^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl, homopiperazin-1-yl, (imino)(oxo)thiazinan-4-yl, (oxo)thiazinan-4-yl or (dioxo)thiazinan-4-yl, any of which groups may be optionally substituted by one or more substituents;

R$^d$ represents hydrogen; or C$_{1-6}$ alkyl, C$_{3-7}$ cycloalkyl, aryl, C$_{3-7}$ heterocycloalkyl or heteroaryl, any of which groups may be optionally substituted by one or more substituents; and R$^e$ represents C$_{1-6}$ alkyl, aryl or heteroaryl, any of which groups may be optionally substituted by one or more substituents.

The present invention also provides a compound of formula (I) as defined above or an N-oxide thereof, or a pharmaceutically acceptable salt or solvate thereof, or a glucuronide derivative thereof, or a co-crystal thereof, for use in therapy.

The present invention also provides a compound of formula (I) as defined above or an N-oxide thereof, or a pharmaceutically acceptable salt or solvate thereof, or a glucuronide derivative thereof, or a co-crystal thereof, for use in the treatment and/or prevention of disorders for which the administration of a modulator of TNFα function is indicated.

In another aspect, the present invention provides for the use of a compound of formula (I) as defined above, or an N-oxide thereof, or a pharmaceutically acceptable salt thereof, for the manufacture of a medicament useful for the treatment of an inflammatory or autoimmune disorder, a neurological or neurodegenerative disorder, pain or a nociceptive disorder, a cardiovascular disorder, a metabolic disorder, an ocular disorder, or an oncological disorder.

In another aspect, the present invention provides a compound of formula (I) as defined above or an N-oxide thereof, or a pharmaceutically acceptable salt or solvate thereof, or a glucuronide derivative thereof, or a co-crystal thereof, for use in the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides a method for the treatment and/or prevention of disorders for which the administration of a modulator of TNFα function is indicated which comprises administering to a patient in need of such treatment an effective amount of a compound of formula (I) as defined above or an N-oxide thereof, or a pharmaceutically acceptable salt or solvate thereof, or a glucuronide derivative thereof, or a co-crystal thereof.

In another aspect, the present invention provides a method for the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder, which comprises administering to a patient in need of such treatment an effective amount of a compound of formula (I) as defined above or an N-oxide thereof, or a pharmaceutically acceptable salt or solvate thereof, or a glucuronide derivative thereof, or a co-crystal thereof.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of use in the invention or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of use in the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; ammonium salts; and salts formed with suitable organic ligands, e.g. quaternary ammonium salts, and meglumine salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

The present invention also includes co-crystals within its scope. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012). Typical examples of co-crystal formers, which may be present in the co-crystal alongside the active pharmaceutical ingredient, include L-ascorbic acid, citric acid, glutaric acid, urea and nicotinamide.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in *Design of Prodrugs*, ed. H. Bundgaard, Elsevier, 1985.

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The expression "$C_{1-4}$ alkylene chain" refers to a divalent straight or branched alkylene chain containing 1 to 4 carbon atoms. Typical examples include methylene, ethylene, methylmethylene, ethylmethylene and dimethylmethylene.

Suitable $C_{2-6}$ alkenyl groups include vinyl and allyl.

Suitable $C_{2-6}$ alkynyl groups include ethynyl, propargyl and butynyl.

The term "$C_{3-7}$ cycloalkyl" as used herein refers to monovalent groups of 3 to 7 carbon atoms derived from a saturated monocyclic hydrocarbon, and may comprise benzo-fused analogues thereof. Suitable $C_{3-7}$ cycloalkyl groups include cyclopropyl, cyclobutyl, benzocyclobutenyl, cyclopentyl, indanyl, cyclohexyl and cycloheptyl.

The term "$C_{4-7}$ cycloalkenyl" as used herein refers to monovalent groups of 4 to 7 carbon atoms derived from a partially unsaturated monocyclic hydrocarbon. Suitable $C_{4-7}$ cycloalkenyl groups include cyclobutenyl, cyclopentenyl, cyclohexenyl and cycloheptenyl.

The term "$C_{4-9}$ bicycloalkyl" as used herein refers to monovalent groups of 4 to 9 carbon atoms derived from a saturated bicyclic hydrocarbon. Typical $C_{4-9}$ bicycloalkyl groups include bicyclo[3.1.0]hexanyl, bicyclo[4.1.0]heptanyl, bicyclo[2.2.2]octanyl and bicyclo[3.3.1]-nonanyl.

Typical ($C_{4-9}$)bicycloalkenyl groups include bicyclo[3.1.0]hexenyl.

The term "aryl" as used herein refers to monovalent carbocyclic aromatic groups derived from a single aromatic ring or multiple condensed aromatic rings. Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzo-furanyl, dihydrobenzothienyl, pyrrolidinyl, indolinyl, dihydroisoindolyl, isoindolinyl, oxazolidinyl, thiazolidinyl, isothiazolidinyl, imidazolidinyl, tetrahydropyranyl, chromanyl, tetrahydrothiopyranyl, piperidinyl, 1,2,3,4-tetrahydroquinolinyl, 1,2,3,4-tetrahydroisoquinolinyl, piperazinyl, 1,2,3,4-tetrahydroquinoxalinyl, hexahydro-[1,2,5]thiadiazolo[2,3-a]pyrazinyl, homopiperazinyl, morpholinyl, benzoxazinyl, thiomorpholinyl, azepanyl, oxazepanyl, diazepanyl, thiadiazepanyl, azocanyl, (imino)(oxo)thiazinanyl, (oxo)thiazinanyl and (dioxo)thiazinanyl.

The term "$C_{3-7}$ heterocycloalkenyl" as used herein refers to monounsaturated or polyunsaturated monocyclic rings containing 3 to 7 carbon atoms and at least one heteroatom selected from oxygen, sulphur and nitrogen, and may comprise benzo-fused analogues thereof. Suitable heterocycloalkenyl groups include thiazolinyl, imidazolinyl, dihydropyranyl, dihydrothiopyranyl and 1,2,3,6-tetrahydropyridinyl.

The term "$C_{4-9}$ heterobicycloalkyl" as used herein corresponds to $C_{4-9}$ bicycloalkyl wherein one or more of the carbon atoms have been replaced by one or more heteroatoms selected from oxygen, sulphur and nitrogen. Typical heterobicycloalkyl groups include 3-azabicyclo[3.1.0]hexanyl, 2-oxa-5-azabicyclo[2.2.1]heptanyl, 6-azabicyclo[3.2.0]heptanyl, 3-azabicyclo[3.1.1]heptanyl, 3-azabicyclo[4.1.0]heptanyl, 2-oxabicyclo[2.2.2]octanyl, quinuclidinyl, 2-oxa-5-azabicyclo-[2.2.2]octanyl, 3-azabicyclo[3.2.1]octanyl, 8-azabicyclo[3.2.1]octanyl, 3-oxa-8-azabicyclo[3.2.1]octanyl, 3,8-diazabicyclo[3.2.1]octanyl, 3,6-diazabicyclo[3.2.2]nonanyl, 3-oxa-7-azabicyclo[3.3.1]nonanyl and 3,9-diazabicyclo[4.2.1]nonanyl.

The term "$C_{4-9}$ spiroheterocycloalkyl" as used herein refers to saturated bicyclic ring systems containing 4 to 9 carbon atoms and at least one heteroatom selected from oxygen, sulphur and nitrogen, in which the two rings are linked by a common atom. Suitable spiroheterocycloalkyl groups include 5-azaspiro[2.3]hexanyl, 5-azaspiro-[2.4]heptanyl, 2-azaspiro[3.3]heptanyl, 2-oxa-6-azaspiro[3.3]heptanyl, 2-oxa-6-azaspiro-[3.4]octanyl, 2-oxa-6-azaspiro[3.5]nonanyl, 7-oxa-2-azaspiro[3.5]nonanyl, 2-oxa-7-azaspiro[3.5]nonanyl and 2,4,8-triazaspiro[4.5]decanyl.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulphur and nitrogen. Suitable heteroaryl groups include furyl, benzofuryl, dibenzofuryl, thienyl, benzothienyl, thieno[2,3-c]pyrazolyl, thieno[3,4-b][1,4]dioxinyl, dibenzothienyl, pyrrolyl, indolyl, 2,3-dihydro-1H-isoindolyl, pyrrolo[2,3-b]pyridinyl, pyrrolo[3,2-c]pyridinyl, pyrrolo[3,4-b]pyridinyl, pyrazolyl, pyrazolo[1,5-a]pyridinyl, pyrazolo[3,4-d]pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]thiazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, [1,2,4]triazolo[1,5-a]pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of use in the invention possess two or more asymmetric centres, they may additionally exist as diastereomers. The invention is to be understood to extend to the use of all such enantiomers and diastereoisomers, and to mixtures thereof in any proportion, including racemates.

Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)↔enol ($CH=CHOH$) tautomers or amide ($NHC=O$)↔hydroxyimine ($N=COH$) tautomers. Formula (I) and the formulae depicted hereinafter are intended to represent all individual tautomers and all possible mixtures thereof, unless stated or shown otherwise.

An illustrative example of a tautomer in accordance with the present invention, is 2-oxo-(1H)-pyridinyl which is a tautomer of 2-hydroxy-pyridinyl.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

In one embodiment, n represents an integer equal to 0. In another embodiment, n represents an integer equal to 1.

In a particular embodiment, n represents an integer equal to 1.

Generally, X represents oxygen, sulphur, S(O), $S(O)_2$, $S(O)(N—R^d)$, $N(C(O)R^d)$, $N(COOR^d)$, $N(SO_2R^d)$, or $N(R^d)$; or an optionally substituted straight or branched $C_{1-4}$ alkylene chain.

Typically, X represents oxygen, sulphur, S(O), or $N(R^d)$; or an optionally substituted straight or branched $C_{1-4}$ alkylene chain;

In a first embodiment, X represents oxygen.
In a second embodiment, X represents sulphur.
In a third embodiment, X represents S(O).
In a fourth embodiment, X represents $S(O)_2$.
In a fifth embodiment, X represents $S(O)(N—R^d)$.
In a sixth embodiment, X represents $N(C(O)R^d)$.
In a seventh embodiment, X represents $N(COOR^d)$.
In an eighth embodiment, X represents $N(SO_2R^d)$.
In a ninth embodiment, X represents $N(R^d)$. In a particular aspect of this embodiment, X represents NH.

In a tenth embodiment, X represents an optionally substituted straight or branched $C_{1-4}$ alkylene chain. Typical values of X according to this embodiment include methylene (—$CH_2$—), (methyl)methylene, ethylene (—$CH_2CH_2$—), (ethyl)methylene, (dimethyl)-methylene, (methyl)ethylene, propylene (—$CH_2CH_2CH_2$—), (propyl)methylene and (dimethyl)ethylene, any of which chains may be optionally substituted by one or more substituents. In one aspect of this embodiment X represents an unsubstituted straight or branched $C_{1-4}$ alkylene chain. In a second aspect of this embodiment, X represents a monosubstituted straight or branched $C_{1-4}$ alkylene chain. In a third aspect of this embodiment, X represents a disubstituted straight or branched $C_{1-4}$ alkylene chain.

In an eleventh embodiment, X represents a carbonyl.
Particular values of X include methylene, oxygen and NH.

In a particular embodiment, X represents oxygen. In another particular embodiment, X represents methylene.

Generally, Y represents $C_{3-7}$ cycloalkyl, aryl or heteroaryl, any of which groups may be optionally substituted by one or more substituents.

Typically, Y represents aryl or heteroaryl, either of which groups may be optionally substituted by one or more substituents.

Illustratively, Y represents aryl, which group may be optionally substituted by one or more substituents.

In a first embodiment, Y represents optionally substituted $C_{3-7}$ cycloalkyl. In one aspect of that embodiment, Y represents unsubstituted $C_{3-7}$ cycloalkyl. In another aspect of that embodiment, Y represents monosubstituted $C_{3-7}$ cycloalkyl. In a further aspect of that embodiment, Y represents disubstituted $C_{3-7}$ cycloalkyl.

In a second embodiment, Y represents optionally substituted aryl. In one aspect of that embodiment, Y represents unsubstituted aryl. In another aspect of that embodiment, Y represents monosubstituted aryl. In a further aspect of that embodiment, Y represents disubstituted aryl.

In a third embodiment, Y represents optionally substituted $C_{3-7}$ heterocycloalkyl. In one aspect of that embodiment, Y represents unsubstituted $C_{3-7}$ heterocycloalkyl. In another aspect of that embodiment, Y represents monosubstituted $C_{3-7}$ heterocycloalkyl. In a further aspect of that embodiment, Y represents disubstituted $C_{3-7}$ heterocycloalkyl.

In a fourth embodiment, Y represents optionally substituted heteroaryl. In one aspect of that embodiment, Y represents unsubstituted heteroaryl. In another aspect of that embodiment, Y represents monosubstituted heteroaryl. In a further aspect of that embodiment, Y represents disubstituted heteroaryl.

Suitably, Y represents benzocyclobutenyl, phenyl, thienyl, thiazolyl, pyridinyl, pyrimidinyl or pyrazolyl any of which groups may be optionally substituted by one or more substituents.

Appropriately, Y represents phenyl, thienyl or thiazolyl, any of which groups may be optionally substituted by one or more substituents.

Appositely, Y represents phenyl, which may be optionally substituted by one or more substituents.

Examples of optional substituents which may be present on the moiety Y include one, two or three substituents independently selected from halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, $(C_{1-6})$alkylsulfonyloxy, amino, $C_{1-6}$ alkyl-amino, di($C_{1-6}$)alkylamino, arylamino, $C_{2-6}$ alkylcarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aminocarbonyl, $C_{1-6}$ alkylaminocarbonyl, di($C_{1-6}$)alkyl-aminocarbonyl, aminosulfonyl, $C_{1-6}$ alkylaminosulfonyl and di($C_{1-6}$)alkylaminosulfonyl.

Examples of particular substituents on the moiety Y include fluoro, chloro, bromo, cyano, nitro, methyl, isopropyl, trifluoromethyl, hydroxy, methoxy, difluoromethoxy, trifluoromethoxy, methylthio, methylsulfinyl, methylsulfonyl, methylsulfonyloxy, amino, methylamino, tert-butylamino, dimethylamino, phenylamino, acetylamino, methylsulfonylamino, formyl, acetyl, cyclopropylcarbonyl, azetidinylcarbonyl, pyrrolidinyl-carbonyl, piperidinylcarbonyl, piperazinylcarbonyl, morpholinylcarbonyl, carboxy, methoxycarbonyl, aminocarbonyl, methylaminocarbonyl, dimethylaminocarbonyl, aminosulfonyl, methylaminosulfonyl and dimethylaminosulfonyl.

Typical examples of particular substituents on the moiety Y include chloro, fluoro, cyano, methoxy, methylsulphonyl, trifluoromethoxy and difluoromethoxy.

Typical values of Y include benzocyclobutenyl, phenyl, (methysulphonyl)phenyl (including 4-methylsulphonyl-phenyl), benzonitrile (including 2-benzonitrile, 3-benzonitrile and 4-benzonitrile), fluorophenyl (including 2-fluorophenyl, 3-fluorophenyl and 4-fluorophenyl), chlorophenyl (including 2-chloro-phenyl, 3-chlorophenyl and 4-chlorophenyl), difluorophenyl (including 2,6-difluoro-phenyl), (chloro)(fluoro)phenyl (including 5-chloro-2-fluorophenyl and 2-chloro-5-fluorophenyl), dichlorophenyl (including 2,5-dichlorophenyl and 2,6-dichlorophenyl), methylphenyl (including 4-methylphenyl), dimethylphenyl (including 2,5-dimethylphenyl and 2,6-dimethylphenyl), (trifluoromethyl)phenyl [including 2-(trifluoromethyl)phenyl], (chloro)(trifluoromethyl)phenyl [including 5-chloro-2-(trifluoromethyl)phenyl], (methyl)-(trifluoromethyl)phenyl [including 2-methyl-5-(trifluoromethyl)phenyl], bis(trifluoro-methyl)phenyl [including 2,5-bis(trifluoromethyl)phenyl], methoxyphenyl (including 2-methoxyphenyl), (difluoromethoxy)phenyl [including 2-(difluoromethoxy)phenyl, 3-(difluoromethoxy)phenyl and 4-(difluoromethoxy)phenyl], (bis-(difluoromethoxy))phenyl [including 2,5-(bis-(difluoromethoxy))-phenyl and including 2,6-(bis-(difluoromethoxy))-phenyl], (difluoromethoxy)(fluoro)phenyl [including 2-(difluoromethoxy)-5-fluorophenyl, 2-(difluoromethoxy)-3-fluorophenyl, 2-(difluoromethoxy)-4-fluorophenyl, 2-(difluoromethoxy)-5-fluorophenyl, 2-(difluoromethoxy)-6-fluorophenyl and 5-(difluoromethoxy)-2-fluorophenyl], (difluoromethoxy)(difluoro)phenyl [(including 2-difluoromethoxy-3,5-difluoro-phenyl and difluoromethoxy-3,5-difluoro-phenyl)], (chloro)(difluoromethoxy)phenyl [including 2-chloro-5-(difluoromethoxy)phenyl, 5-chloro-2-(difluoromethoxy) phenyl, 5-chloro-3-(difluoromethoxy) phenyl, and 6-chloro-2-(difluoromethoxy) phenyl], (cyano) (difluoromethoxy) [including 6-cyano-2-(difluoromethoxy)-phenyl] (trifluoromethoxy) phenyl [including 2-(trifluoromethoxy)-phenyl], methylsulfonyloxyphenyl, (chloro)(trifluoromethoxy)phenyl, [including 3-chloro-6-trifluoromethoxy-phenyl)], (amino)(chloro)phenyl [including 5-amino-2-chloro-phenyl], methylthienyl [including 3-methylthien-2-yl), methylthiazolyl (including 2-methyl-1,3-thiazol-4-yl and 4-methyl-1,3-thiazol-4-yl)], (chloro)thiazolyl [including 4-chloro-1,3-thiazolyl], (chloro)(methyl)thiazolyl [including 5-chloro-2-methyl-1,3-thiazol-4-yl], dimethylthiazolyl [including 2,4-dimethyl-1,3-thiazol-5-yl], pyridinyl [including pyridin-3-yl and pyridin-4-yl], (methyl)(trifluoromethyl)thiazolyl [including 2-methyl-4-trifluoromethyl-1,3-thiazolyl], (dimethoxy)pyrimidinyl [including 4,6-dimethoxy-pyridin-5-yl] and (methoxy)pyrazinyl [including 5-methoxypyrazinyl].

Selected values of Y include phenyl, (methysulphonyl)phenyl, benzonitrile chlorophenyl, (chloro)(fluoro)phenyl, dichlorophenyl, dimethylphenyl, (trifluoromethyl)phenyl, (difluoromethoxy)phenyl, (bis-(difluoromethoxy))phenyl (difluoromethoxy)(fluoro)phenyl, (difluoromethoxy)(cyano)phenyl, (difluoromethoxy)(difluoro)phenyl, (chloro)(difluoromethoxy)phenyl, (chloro)(trifluoromethoxy)phenyl, (chloro)(methyl)thiazolyl, (chloro)thiazolyl, (methyl)(trifluoromethyl)thiazolyl, (dimethoxy)pyrimidinyl and (methoxy)pyrazinyl.

Particular values of Y include (difluoromethoxy)phenyl, (difluoromethoxy)(fluoro)phenyl, (chloro)(difluoromethoxy)phenyl and (difluoromethoxy)(cyano)phenyl.

Specific values of Y include 2-difluoromethoxy-phenyl, 2-difluoromethoxy-5-chloro-phenyl, 2-difluoromethoxy-5-chloro-phenyl, 2-difluoromethoxy-5-fluoro-phenyl, and 2-difluoromethoxy-5-cyano-phenyl.

In a particular embodiment, Y represents 2-(difluoromethoxy)phenyl.

In another particular embodiment, Y represents 2-(difluoromethoxy)-5-chloro-phenyl.

Generally, $R^1$ represents hydrogen, halogen, cyano, trifluoromethyl; $—S(O)_2(N—R^d)$, or $—CO_2R^d$; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl$(C_{1-6})$alkylaryl-, heteroaryl-$(C_{3-7})$heterocycloalkyl-, $(C_{3-7})$cycloalkyl-heteroaryl-, $(C_{3-7})$cycloalkyl$(C_{1-6})$alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl$(C_{1-6})$alkyl-heteroaryl-, $(C_{3-7})$heterocycloalkenyl-heteroaryl-, $(C_{4-9})$heterobicycloalkyl-heteroaryl-, heteroarylaryl-, or $(C_{4-9})$spiroheterocycloalkyl-heteroaryl-, any of which groups may be optionally substituted by one or more substituents.

Generally, $R^2$ and $R^3$ represent independently hydrogen, halogen, cyano, nitro, hydroxy, trifluoromethyl, trifluoromethoxy or $—OR^a$; or $C_{1-6}$ alkyl optionally substituted by one or more substituents.

Generally, $R^4$ represents hydrogen, hydroxy, halogen, trifluoromethyl, $—NR^bR^c$, $—NR^cC(O)R^d$, $—NH—S(O)_2R^e$, $—S(O)_2R^a$, $—S(O)(N—R^d)R^a$ or $—O—(CO)—R^d$; or $C_{1-6}$ alkoxy, $C_{1-6}$ alkyl, $C_{2-6}$ alkynyl, heteroaryl, any of which groups may be optionally substituted by one or more substituents.

Generally, $R^{5a}$ and $R^{5b}$ represent independently hydrogen, hydroxy, halogen, cyano, trifluoromethyl, $—NR^bR^c$, $—NR^cC(O)R^d$, $—(CO)NR^cR^d$, $—NH—S(O)_2R^e$, $—S—R^a$, $—(SO)—R^a$, $—S(O)_2R^a$, $—S(O)(N—R^d)R^a$, $—S(O)_2(N—R^d)$, $—OR^a$, $—C(O)_2R^d$, or $—O(CO)—R^d—$; or $C_{1-6}$ alkyl, $C_{2-6}$ alkenyl, $C_{2-6}$ alkynyl, aryl, or heteroaryl, any of which groups may be optionally substituted by one or more substituents.

Suitably, $R^{5a}$ represents hydrogen, hydroxy, halogen, cyano, trifluoromethyl, $—NR^bR^c$, $—NR^cC(O)R^d$, $—(CO)NR^cR^d$, $—NH—S(O)_2R^e$, $—S—R^a$, $—(SO)—R^a$, $—S(O)_2R^a$, $—S(O)(N—R^d)R^a$, $—S(O)_2(N—R^d)$, $—OR^a$, $—C(O)_2R^d$, or $—O(CO)—R^d—$; or $C_{1-6}$ alkyl, $C_{2-6}$ alkenyl, $C_{2-6}$ alkynyl, aryl, heteroaryl, any of which groups may be optionally substituted by one or more substituents; and $R^{5b}$ represents hydrogen, hydroxy, halogen, cyano, or trifluoromethyl; or $C_{1-6}$ alkyl, which group may be optionally substituted by one or more substituents.

Alternatively, $R^{5a}$ and $R^{5b}$ when taken together with the carbon to which they are attached represent a carbonyl, thiocarbonyl, or $—C{=}N—OH$.

Examples of optional substituents which may be present on $R^1$, $R^2$, $R^3$, $R^4$, $R^{5a}$ and $R^{5b}$ include one, two or three substituents independently selected from halogen, halo-$(C_{1-6})$alkyl, cyano, cyano$(C_{1-6})$alkyl, nitro, nitro$(C_{1-6})$alkyl, $C_{1-6}$ alkyl, $(C_{3-7})$cycloalkyl, difluoromethyl, trifluoromethyl, difluoroethyl, trifluoroethyl, $C_{2-6}$ alkenyl, hydroxy, hydroxy$(C_{1-6})$alkyl, $C_{1-6}$ alkoxy, difluoromethoxy, trifluoromethoxy, trifluoroethoxy, carboxy$(C_{3-7})$cycloalkyl-oxy, $C_{1-3}$ alkylenedioxy, $C_{1-6}$ alkoxy$(C_{1-6})$alkyl, $C_{1-6}$ alkylthio, $C_{1-6}$ alkylsulphinyl, $C_{1-6}$ alkylsulphonyl, aryl-sulphonyl, $(C_{1-6})$alkylsulphonyl$(C_{1-6})$alkyl, oxo, amino, amino$(C_{1-6})$alkyl, $C_{1-6}$ alkyl-amino, di$(C_{1-6})$alkylamino, hydroxy$(C_{1-6})$alkylamino, $C_{1-6}$ alkoxyamino, $(C_{1-6})$alkoxy-$(C_{1-6})$alkylamino, $[(C_{1-6})$alkoxy](hydroxy)$(C_{1-6})$alkylamino, $[(C_{1-6})$alkylthio](hydroxy)-$(C_{1-6})$alkylamino, $N—[(C_{1-6})$alkyl]-N-[hydroxy$(C_{1-6})$alkyl]amino, di$(C_{1-6})$alkylamino-$(C_{1-6})$alkylamino, N-[di$(C_{1-6})$alkylamino$(C_{1-6})$alkyl]-N-[hydroxy$(C_{1-6})$alkyl]

amino, hydroxy($C_{1-6}$)alkyl($C_{3-7}$)cycloalkylamino, (hydroxy)[($C_{3-7}$)cycloalkyl($C_{1-6}$)alkyl]amino, ($C_{3-7}$)heterocycloalkyl($C_{1-6}$)alkylamino, oxo($C_{3-7}$)heterocycloalkyl($C_{1-6}$)alkylamino, ($C_{1-6}$)alkylheteroarylamino, heteroaryl($C_{1-6}$)alkylamino, ($C_{1-6}$)alkylheteroaryl($C_{1-6}$)alkyl-amino, $C_{2-6}$ alkylcarbonylamino, N—[($C_{1-6}$)alkyl]-N—[($C_{2-6}$)alkylcarbonyl]amino, ($C_{2-6}$)alkyl-carbonylamino($C_{1-6}$)alkyl, $C_{3-6}$ alkenylcarbonylamino, bis[($C_{3-6}$)alkenylcarbonyl]amino, N—[($C_{1-6}$)alkyl]-N—[($C_{3-7}$)cycloalkylcarbonyl]amino, $C_{2-6}$ alkoxycarbonylamino, $C_{2-6}$ alkoxycarbonyl($C_{1-6}$)alkylamino, $C_{1-6}$ alkylaminocarbonylamino, $C_{1-6}$ alkylsulphonyl-amino, N—[($C_{1-6}$)alkyl]-N—[($C_{1-6}$)alkylsulphonyl]amino, bis[($C_{1-6}$)alkylsulphonyl]amino, N—[($C_{1-6}$)alkyl]-N-[carboxy($C_{1-6}$)alkyl]amino, carboxy($C_{3-7}$)cycloalkylamino, carboxy-($C_{3-7}$)cycloalkyl($C_{1-6}$)alkylamino, formyl, $C_{2-6}$ alkylcarbonyl, ($C_{3-7}$)cycloalkylcarbonyl, phenylcarbonyl, ($C_{2-6}$)alkylcarbonyloxy($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl($C_{1-6}$)alkoxycarbonyl, $C_{2-6}$ alkoxycarbonylmethylidenyl, a carboxylic acid isostere or prodrug moiety Ω, —($C_{1-6}$)alkyl-Ω, aminocarbonyl, $C_{1-6}$ alkylaminocarbonyl, hydroxy($C_{1-6}$)alkylamino-carbonyl, di($C_{1-6}$)alkylaminocarbonyl, aminocarbonyl($C_{1-6}$)alkyl, aminosulphonyl, di($C_{1-6}$)alkylaminosulphonyl, ($C_{1-6}$)alkylsulphoximinyl and [($C_{1-6}$)alkyl][N—($C_{1-6}$)alkyl]-sulphoximinyl.

By the expression "carboxylic acid isostere or prodrug moiety" is meant any functional group, structurally distinct from a carboxylic acid moiety, that will be recognised by a biological system as being similar to, and thus capable of mimicking, a carboxylic acid moiety, or will be readily convertible by a biological system in vivo into a carboxylic acid moiety. A synopsis of some common carboxylic acid isosteres is presented by N. A. Meanwell in *J. Med. Chem.*, 2011, 54, 2529-2591 (cf. in particular FIGS. 25 and 26). An alternative carboxylic acid isostere is described by N Pemberton et al. in *ACS Med. Chem. Lett.*, 2012, 3, 574-578. Typical examples of suitable carboxylic acid isostere or prodrug moieties represented by Ω include the functional groups of formula (i) to (xliii):

(i)
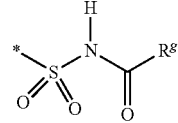

(ii)
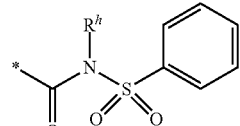

(iii)
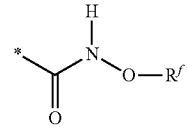

(iv)
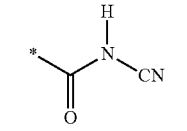

(v)
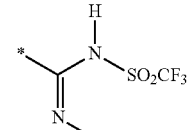

(vi)
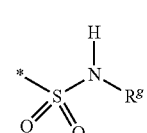

(vii)
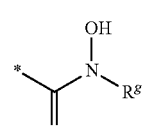

(viii)
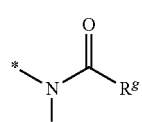

(ix)
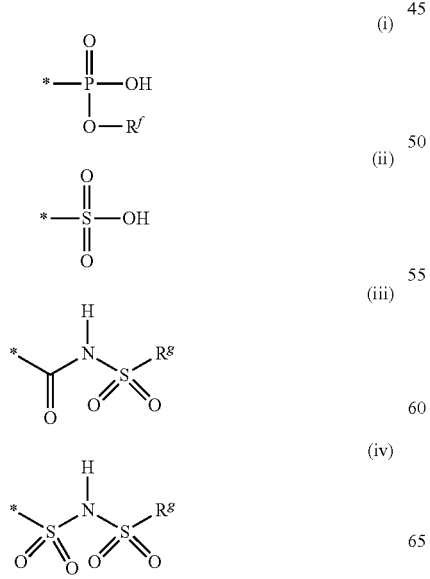

(x)
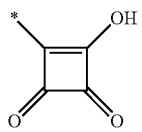

(xi)
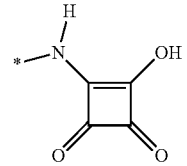

(xii)

(xiii)

(xiv)

-continued (xxxvi)

(xxxvii)

(xxxviii)

(xxxix)

(xl)

(xli)

(xlii)

(xliii)

wherein
the asterisk (*) represents the site of attachment to the remainder of the molecule;
n is zero, 1 or 2;
Q represents oxygen or sulphur;
$R^f$ represents hydrogen, $C_{1-6}$ alkyl or —$CH_2CH(OH)CH_2OH$;
$R^g$ represents $C_{1-6}$ alkyl, trifluoromethyl, —$CH_2CH_2F$, —$CH_2CHF_2$, —$CH_2CF_3$ or —$CF_2CF_3$;
$R^h$ represents hydrogen, cyano or —$CO_2R^d$, in which $R^d$ is as defined above; and
$R^j$ represents hydrogen or halogen.
In one embodiment, n is zero. In another embodiment, n is 1. In a further embodiment, n is 2.

In one embodiment, Q represents oxygen. In another embodiment, Q represents sulphur.

In one embodiment, $R^f$ represents hydrogen. In another embodiment, $R^f$ represents $C_{1-6}$ alkyl, especially methyl. In a further embodiment, $R^f$ is —$CH_2CH(OH)CH_2OH$.

In one embodiment, $R^g$ represents $C_{1-6}$ alkyl, especially methyl. In another embodiment, $R^g$ represents trifluoromethyl, —$CH_2CH_2F$, —$CH_2CHF_2$, —$CH_2CF_3$ or —$CF_2CF_3$. In a first aspect of that embodiment, $R^g$ represents trifluoromethyl. In a second aspect of that embodiment, $R^g$ represents —$CH_2CH_2F$. In a third aspect of that embodiment, $R^g$ represents —$CH_2CHF_2$. In a fourth aspect of that embodiment, $R^g$ represents —$CH_2CF_3$. In a fifth aspect of that embodiment, $R^g$ represents —$CF_2CF_3$.

In one embodiment, $R^h$ is hydrogen. In another embodiment, $R^h$ represents cyano. In a further embodiment, $R^h$ represents —$CO_2R^d$, especially methoxycarbonyl.

In one embodiment, R represents hydrogen. In another embodiment, R represents halogen, especially chloro.

In a selected embodiment, Ω represents tetrazolyl, especially a C-linked tetrazolyl moiety of formula (xxiv) or (xxv) as depicted above, in particular a group of formula (xxiv) as depicted above.

In another embodiment, Ω represents $C_{1-6}$ alkylsulphonylaminocarbonyl, i.e. a moiety of formula (iii) as depicted above wherein $R^g$ represents $C_{1-6}$ alkyl.

In another embodiment, Ω represents $C_{1-6}$ alkylaminosulphonyl, i.e. a moiety of formula (x) as depicted above wherein $R^g$ represents $C_{1-6}$ alkyl.

In a further embodiment, Ω represents ($C_{1-6}$)alkylcarbonylaminosulphonyl, i.e. a moiety of formula (v) as depicted above wherein $R^g$ represents $C_{1-6}$ alkyl.

Typical examples of optional substituents on $R^1$, $R^2$, $R^3$, $R^4$ $R^{5a}$ and $R^{5b}$ include hydroxy, hydroxy($C_{1-6}$)alkyl and $C_{1-6}$ alkoxy.

Examples of particular substituents on $R^1$, $R^2$, $R^3$, $R^4$, $R^{5a}$ and $R^{5b}$ include fluoro, chloro, bromo, fluoromethyl, fluoroisopropyl, cyano, cyanoethyl, cyanoisopropyl, nitro, nitromethyl, methyl, ethyl, isopropyl, isobutyl, tert-butyl, cyclobutyl, cyclopropyl, difluoromethyl, trifluoromethyl, difluoroethyl, trifluoro-ethyl, ethenyl, hydroxy, hydroxymethyl, hydroxyisopropyl, methoxy, isopropoxy, difluoromethoxy, trifluoromethoxy, trifluoroethoxy, carboxycyclobutyloxy, methylene-dioxy, ethylenedioxy, methoxymethyl, methoxyethyl, methylthio, methylsulphinyl, methylsulphonyl, methylsulphonylethyl, oxo, amino, aminomethyl, aminoisopropyl, methylamino, ethylamino, dimethylamino, hydroxyethylamino, hydroxypropylamino, (hydroxy)(methyl)propylamino, methoxyamino, methoxyethylamino, (hydroxy)-(methoxy)(methyl)propylamino, (hydroxy)(methylthio)butylamino, N-(hydroxyethyl)-N-(methyl)amino, dimethylaminoethylamino, (dimethylamino)(methyl)propylamino, N-(dimethylaminoethyl)-N-(hydroxyethyl)amino, hydroxymethylcyclopentylamino, hydroxycyclobutylmethylamino, (cyclopropyl)(hydroxy)propylamino, morpholinylethyl-amino, oxopyrrolidinylmethylamino, ethyloxadiazolylamino, methylthiadiazolylamino, thiazolylmethylamino, thiazolylethylamino, pyrimidinylmethylamino, methylpyrazolyl-methylamino, acetylamino, N-acetyl-N-methylamino, N-isopropylcarbonyl-N-methyl-amino, acetylaminomethyl, ethenylcarbonylamino, bis(ethenylcarbonyl)amino, N-cyclopropylcarbonyl-N-methylamino, methoxycarbonylamino, ethoxycarbonylamino, tert-butoxycarbonylamino, methoxycarbonylethylamino, ethylaminocarbonylamino, butylaminocarbonylamino, methylsulphonylamino, N-methyl-N-(methylsulphonyl)amino, bis(methylsulphonyl)amino, N-(carboxymethyl)-N-methylamino, N-(carboxyethyl)-N-methylamino, carboxycyclopentylamino, carboxycyclopropylmethylamino, formyl, acetyl, isopropylcarbonyl, cyclobutylcarbonyl, phenylcarbonyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxycarbonylmethyl, ethoxycarbonylethyl, morpholinylethoxycarbonyl, ethoxycarbonylmethylidenyl, methylsulphonylamino-carbonyl, acetylaminosulphonyl, methoxyaminocarbonyl, tetrazolyl, tetrazolylmethyl, hydroxyoxadiazolyl, aminocarbonyl, methylaminocarbonyl, hydroxyethylaminocarbonyl, dimethylaminocarbonyl, aminocarbonylmethyl, aminosulphonyl, methylaminosulphonyl, dimethylaminosulphonyl, phenylsulphonyl, methylsulphoximinyl and (methyl)(N-methyl)sulphoximinyl.

Illustrative examples of particular substituents on $R^1$, $R^2$, $R^3$, $R^4$, $R^{5a}$ and $R^{5b}$ include oxo, hydroxy, hydroxyisopropyl and methoxy.

Typically, $R^1$ represents halogen or cyano; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl$(C_{3-7})$heterocycloalkyl-, $(C_{3-7})$cycloalkyl-heteroaryl-, $(C_{3-7})$cycloalkyl-$(C_{1-6})$alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl$(C_{1-6})$alkyl-heteroaryl-, $(C_{3-7})$heterocycloalkenyl-heteroaryl-, $(C_{4-9})$heterobicycloalkyl-heteroaryl-, $(C_{4-9})$spiroheterocycloalkyl-heteroaryl-, or heteroaryl-aryl, any of which groups may be optionally substituted by one or more substituents.

Suitably, $R^1$ represents halogen, $(C_{3-7})$heterocycloalkenyl, aryl, heteroaryl, $(C_{3-7})$cycloalkyl-heteroaryl-, $(C_{3-7})$heterocycloalkyl-heteroaryl-, or heteroraryl-aryl, either of which groups may be optionally substituted by one or more substituents.

Illustratively, $R^1$ represents halogen; or heteroaryl or $(C_{3-7})$heterocycloalkyl-heteroaryl-, either of which groups may be optionally substituted by one or more substituents.

In a first embodiment, $R^1$ represents hydrogen.

In a second embodiment, $R^1$ represents halogen. In one aspect of that embodiment, $R^1$ represents bromo. In a second aspect, $R^1$ represents chloro.

In a third embodiment, $R^1$ represents cyano.

In a fourth embodiment, $R^1$ represents —$CO_2R^d$.

In a fifth embodiment, $R^1$ represents optionally substituted $C_{1-6}$ alkyl. In one aspect of that embodiment, $R^1$ represents optionally substituted methyl. In another aspect of that embodiment, $R^1$ represents optionally substituted ethyl.

In a sixth embodiment, $R^1$ represents optionally substituted $C_{2-6}$ alkynyl. In one aspect of that embodiment, $R^1$ represents optionally substituted butynyl.

In a seventh embodiment, $R^1$ represents optionally substituted aryl. In one aspect of that embodiment, $R^1$ represents optionally substituted phenyl.

In an eighth embodiment, $R^1$ represents optionally substituted $C_{3-7}$ heterocycloalkyl. In one aspect of this embodiment, $R^1$ represents optionally substituted 2,3-dihydro-1H-isoindole. In another aspect of this embodiment, $R^1$ represents optionally substituted azetidinyl. In another aspect of this embodiment, $R^1$ represents optionally substituted pyrrolidinyl.

In a ninth embodiment, $R^1$ represents optionally substituted $C_{3-7}$ heterocycloalkenyl.

In a tenth embodiment, $R^1$ represents optionally substituted heteroaryl. In selected aspects of that embodiment, $R^1$ represents benzofuryl, thienyl, indolyl, isoindolyl, pyrazolyl, indazolyl, isoxazolyl, thiazolyl, imidazolyl, pyridinyl, quinolinyl, pyridazinyl, pyrimidinyl or pyrazinyl, any of which groups may be optionally substituted by one or more substituents.

In an eleventh embodiment, $R^1$ represents optionally substituted $(C_{3-7})$-heterocycloalkyl$(C_{1-6})$alkyl-aryl-. In a first aspect of that embodiment, $R^1$ represents optionally substituted pyrrolidinylmethylphenyl-. In a second aspect of that embodiment, $R^1$ represents optionally substituted piperazinylmethylphenyl-. In third aspect of that embodiment, $R^1$ represents optionally substituted morpholinyl-pyrimidinyl.

In a twelfth embodiment, $R^1$ represents optionally substituted heteroaryl$(C_{3-7})$-heterocycloalkyl-. In one aspect of that embodiment, $R^1$ represents optionally substituted pyridinylpiperazinyl-.

In a thirteenth embodiment, $R^1$ represents optionally substituted $(C_{3-7})$cycloalkyl-heteroaryl-. In a first aspect of that embodiment, $R^1$ represents optionally substituted cyclohexylpyrazolyl-. In a second aspect of that embodiment, $R^1$ represents optionally substituted cyclohexylpyridinyl-. In a third aspect of that embodiment, $R^1$ represents optionally substituted cyclopropylpyrimidinyl-. In a fourth aspect of that embodiment, $R^1$ represents optionally substituted cyclobutylpyrimidinyl-. In a fifth aspect of that embodiment, $R^1$ represents optionally substituted cyclopentylpyrimidinyl-. In a sixth aspect of that embodiment, $R^1$ represents optionally substituted cyclohexylpyrimidinyl-. In a seventh aspect of that embodiment, $R^1$ represents optionally substituted cyclohexyl-pyrazinyl-. In an eighth aspect of that embodiment, $R^1$ represents optionally substituted cyclopropylpyridinyl. In ninth aspect of that embodiment, $R^1$ represents optionally substituted cyclopropylpyrazolyl.

In a fourteenth embodiment, $R^1$ represents optionally substituted $(C_{4-7})$-cycloalkenyl-heteroaryl-.

In a fifteenth embodiment, $R^1$ represents optionally substituted $(C_{3-7})$-heterocycloalkyl-heteroaryl-. In a first aspect of that embodiment, $R^1$ represents optionally substituted pyrrolidinylpyridinyl-. In a second aspect of that embodiment, $R^1$ represents optionally substituted tetrahydropyranylpyridinyl-. In a third aspect of that embodiment, $R^1$ represents optionally substituted piperidinylpyridinyl-. In a fourth aspect of that embodiment, $R^1$ represents optionally substituted piperazinylpyridinyl-. In a fifth aspect of that embodiment, $R^1$ represents optionally substituted morpholinylpyridinyl-. In a sixth aspect of that embodiment, $R^1$ represents optionally substituted thiomorpholinyl-pyridinyl-. In a seventh aspect of that embodiment, $R^1$ represents optionally substituted diazepanylpyridinyl-. In an eighth aspect of that embodiment, $R^1$ represents optionally substituted oxetanylpyrimidinyl-. In a ninth aspect of that embodiment, $R^1$ represents optionally substituted azetidinylpyrimidinyl-. In a tenth aspect of that embodiment, $R^1$ represents optionally substituted tetrahydrofuranylpyrimidinyl-. In an eleventh aspect of that embodiment, $R^1$ represents optionally substituted pyrrolidinylpyrimidinyl-. In a twelfth aspect of that embodiment, $R^1$ represents optionally substituted tetrahydropyranyl-pyrimidinyl-. In a thirteenth aspect of that embodiment, $R^1$ represents optionally substituted piperidinylpyrimidinyl-. In a fourteenth aspect of that embodiment, $R^1$ represents optionally substituted piperazinylpyrimidinyl-. In a fifteenth aspect of that embodiment, $R^1$ represents optionally substituted morpholinylpyrimidinyl-. In a sixteenth aspect of that embodiment, $R^1$ represents optionally substituted thiomorpholinyl-pyrimidinyl-. In a seventeenth aspect of that embodiment, $R^1$ represents optionally substituted azepanylpyrimidinyl-. In an eighteenth aspect of that embodiment, $R^1$ represents optionally substituted oxazepanylpyrimidinyl-. In a nineteenth aspect of that embodiment, $R^1$ represents optionally substituted diazepanylpyrimidinyl-. In a twentieth aspect of that embodiment, $R^1$ represents optionally substituted thiadiazepanyl-pyrimidinyl-. In a twenty-first aspect of that embodiment, $R^1$ represents optionally substituted oxetanylpyrazinyl-. In a twenty-second aspect of that embodiment, $R^1$ represents optionally substituted piperidinylpyrazinyl-. In a twenty-third aspect of that embodiment, $R^1$ represents optionally substituted tetrahydropyranylpyridinyl. In a twenty-fourth aspect of this embodiment, $R^1$ represents tetrahydro-thiopyranylpyrimidinyl. In a twenty-fifth aspect of this embodiment, $R^1$ represents tetrahydro-thiophenyl-pyrazolyl. In a twenty-sixth aspect of this embodiment, $R^1$ represents (imino)(oxo)thiazinanyl-pyrimidinyl. In a twenty-seventh aspect of this embodiment, $R^1$ represents (oxo)thiazinanyl-pyrimidinyl. In a twenty-eighth aspect of this embodiment, $R^1$ represents (dioxo)thiazinanyl-pyrimidinyl.

In a sixteenth embodiment, $R^1$ represents optionally substituted $(C_{3-7})$-heterocycloalkyl$(C_{1-6})$alkyl-heteroaryl-. In a first aspect of that embodiment, $R^1$ represents optionally substituted morpholinylmethylthienyl-. In a second aspect of that embodiment, $R^1$ represents optionally substituted morpholinylethylpyrazolyl-.

In a seventeenth embodiment, $R^1$ represents optionally substituted $(C_{3-7})$-heterocycloalkenyl-heteroaryl-.

In an eighteenth embodiment, $R^1$ represents optionally substituted $(C_{4-9})$-heterobicycloalkyl-heteroaryl-.

In a nineteenth embodiment, $R^1$ represents optionally substituted $(C_{4-9})$-spiroheterocycloalkyl-heteroaryl-.

In a twentieth embodiment, $R^1$ represents optionally substituted $(C_{3-7})$cycloalkyl-$(C_{1-6})$alkyl-heteroaryl-. In one aspect of that embodiment, $R^1$ represents optionally substituted cyclohexylmethylpyrimidinyl-.

In a twenty-first embodiment, $R^1$ represents optionally substituted $(C_{4-9})$-bicycloalkyl-heteroaryl-.

In a twenty-second embodiment, $R^1$ represents optionally substituted $(C_{4-9})$-bicycloalkenyl-heteroaryl-.

In a twenty-third embodiment, $R^1$ represents optionally substituted heteroaryl-aryl.

In one aspect of this embodiment, $R^1$ represents triazolyl-phenyl.

Appositely, $R^1$ represents hydrogen, chloro, bromo, cyano or —$CO_2R^d$; or ethyl, butynyl, phenyl, triazolyl-phenyl, azetidinyl, pyrrolidinyl, piperidinyl, piperazinyl, morpholinyl, 1,2,3,6-tetrahydropyridinyl, 3,6-dihydropyridinyl, benzofuryl, thienyl, indolyl, pyrazolyl, indazolyl, isoxazolyl, thiazolyl, imidazolyl, pyridinyl, quinolinyl, pyridazinyl, pyrimidinyl, pyrazinyl, pyrrolidinylmethylphenyl, piperazinylmethylphenyl, pyridinylpiperazinyl, cyclohexylpyrazolyl, cyclohexylpyridinyl, cyclopropylpyrimidinyl, cyclobutylpyrimidinyl, cyclopentylpyrimidinyl, cyclohexylpyrimidinyl, cyclohexylpyrazinyl, cyclohexylmethylpyrimidinyl, cyclohexenylpyridinyl, cyclopropylpyridinyl, cyclopropylpyrazolyl, cyclohexenylpyrimidinyl, bicyclo[3.1.0] hexanylpyridinyl, bicyclo[3.1.0]hexanyl-pyrimidinyl, bicyclo[3.1.0]hexenyl-pyrimidinyl bicyclo[4.1.0]heptanylpyrimidinyl, bicyclo[2.2.2]octanylpyrimidinyl, pyrrolidinylpyridinyl, tetrahydropyranylpyridinyl, tetrahydrothiopyranylpyridinyl, piperidinylpyridinyl, piperazinylpyridinyl, morpholinylpyridinyl, thiomorpholinylpyridinyl, diazepanylpyridinyl, oxetanylpyridinyl, azetidinylpyrimidinyl, tetrahydrofuranylpyrimidinyl, pyrrolidinyl-pyrimidinyl, tetrahydropyranylpyrimidinyl, piperidinylpyrimidinyl, piperazinyl-pyrimidinyl, piperazinyl)hexahydro-[1,2,5]thiadiazolo[2,3-a]pyrazinylpyrimidinyl, morpholinyl-pyrimidinyl, thiomorpholinylpyrimidinyl, azepanylpyrimidinyl, oxazepanylpyrimidinyl, diazepanylpyrimidinyl, thiadiazepanylpyrimidinyl, oxetanylpyrazinyl, piperidinyl-pyrazinyl, morpholinylmethylthienyl, morpholinylethylpyrazolyl, 1,1-(dioxidotetrahydrothiophenyl)pyrazolyl, 3-azabicyclo [3.1.0]-hexanylpyridinyl, 3-azabicyclo[3.1.0]hexanylpyridazinyl, 3-azabicyclo[3.1.0]hexanyl-pyrimidinyl, 2-oxa-5-azabicyclo[2.2.1]heptanylpyrimidinyl, 3-azabicyclo[3.1.1]heptanyl-pyrimidinyl, 3-azabicyclo[4.1.0]heptanylpyridinyl, 3-azabicyclo[4.1.0]heptanyl-pyrimidinyl, 2-oxabicyclo[2.2.2]octanylpyrimidinyl, 3-azabicyclo[3.2.1] octanyl-pyrimidinyl, 8-azabicyclo[3.2.1]octanylpyrimidinyl, 3-oxa-8-azabicyclo[3.2.1]octanyl-pyrimidinyl, 3,6-diazabicyclo[3.2.2]nonanylpyrimidinyl, 3-oxa-7-azabicyclo [3.3.1]-nonanylpyrimidinyl, 3,7-dioxa-9-azabicyclo[3.3.1]-nonanylpyrimidinyl, 5-azaspiro[2.3]hexanylpyrimidinyl, 5-azaspiro[2.4]heptanyl-pyrimidinyl, 2-azaspiro[3.3]heptanylpyrimidinyl, 2-oxa-6-azaspiro[3.3]heptanyl-pyrimidinyl, 2-oxa-6-azaspiro[3.4]octanylpyrimidinyl, 2-oxa-6-azaspiro [3.5]nonanyl-pyrimidinyl, 2-oxa-7-azaspiro[3.5]nonanylpyrimidinyl, 2,4,8-triazaspiro[4.5]decanyl-pyrimidinyl, 3,6-epiminofuro [3.2-b]furanyl-pyrimidinyl, (imino)(oxo) thiazinanyl-pyrimidinyl, (oxo)thiazinanyl-pyrimidinyl, (dioxo)thiazinanyl-pyrimidinyl, or cyclobutylpyrimidinyl, any of which groups may be optionally substituted by one or more substituents.

Illustratively, $R^1$ represents bromo; or pyridinyl or (morpholino)pyrimidinyl, any of which groups may be optionally substituted by one or more substituents.

Typical examples of optional substituents on $R^1$ include one, two or three substituents independently selected from halogen, halo$(C_{1-6})$alkyl, cyano, cyano$(C_{1-6})$alkyl, nitro$(C_{1-6})$alkyl, $C_{1-6}$ alkyl, trifluoromethyl, trifluoroethyl, $C_{2-6}$ alkenyl, hydroxy, hydroxy$(C_{1-6})$alkyl, $C_{1-6}$ alkoxy, trifluoroethoxy, carboxy$(C_{3-7})$cycloalkyloxy, $C_{1-6}$ alkylthio, $C_{1-6}$ alkylsulphonyl, aryl-sulphonyl, $(C_{1-6})$alkylsulphonyl $(C_{1-6})$alkyl, oxo, amino, amino-$(C_{1-6})$alkyl, $C_{1-6}$ alkylamino, di$(C_{1-6})$alkylamino, $(C_{1-6})$alkoxy$(C_{1-6})$alkylamino, N—[$(C_{1-6})$alkyl]-N-[hydroxy$(C_{1-6})$alkyl]amino, $(C_{2-6})$alkylcarbonylamino$(C_{1-6})$alkyl, $C_{1-6}$ alkylsulphonylamino, N—[$(C_{1-6})$alkyl]-N—[$(C_{1-6})$alkylsulphonyl]amino, bis[$(C_{1-6})$alkyl-sulphonyl]amino, N—[$(C_{1-6})$alkyl]-N-[carboxy$(C_{1-6})$alkyl]amino, carboxy$(C_{3-7})$cycloalkyl-amino, carboxy$(C_{3-7})$cycloalkyl$(C_{1-6})$alkylamino, formyl, $C_{2-6}$ alkylcarbonyl, $(C_{2-6})$alkyl-carbonyloxy$(C_{1-6})$alkyl, carboxy, carboxy$(C_{1-6})$alkyl, $C_{2-6}$ alkoxycarbonyl, $C_{2-6}$ alkoxycarbonyl$(C_{1-6})$alkyl, morpholinyl$(C_{1-6})$alkoxycarbonyl, $C_{2-6}$ alkoxycarbonyl-methylidenyl, aminocarbonyl, di$(C_{1-6})$alkylaminocarbonyl, aminosulphonyl, $(C_{1-6})$alkylsulphoximinyl and [$(C_{1-6})$alkyl][N—$(C_{1-6})$alkyl]sulphoximinyl.

Suitable examples of optional substituents on $R^1$ include one, two or three substituents independently selected from halogen, hydroxy, trifluoromethyl, $C_{1-6}$ alkyl, halo $(C_{1-6})$ alkyl, $C_{1-6}$ alkoxy, $C_{2-6}$ alkylcarbonyl, $C_{2-6}$ alkylcarbonylamino$(C_{1-6})$alkyl, oxycarbonyl, $C_{2-6}$ alkyloxycarbonyl, (hydroxy)$C_{1-6}$ alkyl, $(C_{3-7})$cycloalkyl, $C_{1-6}$ alkylsulphonyl, arylsulphonyl, $(C_{1-6})$alkylsulphonyl$(C_{1-6})$alkyl, di$(C_{1-6})$alkylaminocarbonyl, oxo, carboxy and $(C_{1-6})$alkylsulphoximinyl.

Illustrative examples of optional substituents on $R^1$ include hydroxy, oxo and $C_{1-6}$ alkoxy.

Typical examples of particular substituents on $R^1$ include one, two or three substituents independently selected from fluoro, chloro, chloromethyl, fluoromethyl, fluoroisopropyl, cyano, cyanoethyl, nitromethyl, methyl, ethyl, isopropyl, isopropylmethyl, cyclobutyl, cyclopropyl, trifluoromethyl, trifluoroethyl, ethenyl, hydroxy, hydroxymethyl, hydroxyisopropyl, methoxy, isopropoxy, trifluoro-ethoxy, carboxycyclobutyloxy, methylthio, phenylsulphonyl, methylsulphonyl, methylsulphonylmethyl, methylsulphonylethyl, oxo, amino, aminomethyl, aminoisopropyl, methylamino, dimethylamino, methoxyethylamino, N-(hydroxyethyl)-N-(methyl)amino, acetylaminomethyl, methylsulphonylamino, N-methyl-N-(methylsulphonyl)amino, bis(methylsulphonyl)amino, N-(carboxyethyl)-N-(methyl)amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxy-carbonylmethyl, ethoxycarbonylethyl, morpholinylethoxycarbonyl, ethoxycarbonyl-methylidenyl, methylsulphonylaminocarbonyl, acetylaminosulphonyl, methoxyaminocarbonyl, tetrazolyl, tetrazolylmethyl, hydroxyoxadiazolyl, aminocarbonyl, amino-sulphonyl, methylsulphoximinyl and (methyl)(N-methyl)sulphoximinyl.

Selected examples of substituents on $R^1$ include one, two or three substituents independently selected from hydroxy, methyl, chloromethyl, hydroxymethyl, hydroxyisopropyl, methoxy, cyclopropyl, cyclobutyl, phenylsulphonyl, methylsulphonyl, methylsulphonylmethyl, methylsulphonylethyl, acetylaminomethyl, carboxy, methoxycarbonyl, tert-butoxycarbonyl, ethoxycarbonyl, methylsulphoximinyl, cyanoisopropyl and fluoroisopropyl.

Illustrative examples of substituents on $R^1$ include one, two or three substituents independently selected from hydroxy, hydroxyisopropyl, methoxy, and oxo.

In a particular embodiment, $R^1$ is substituted by hydroxy $(C_{1-6})$alkyl. In one aspect of that embodiment, $R^1$ is substituted by hydroxyisopropyl, especially 2-hydroxyprop-2-yl.

In a second particular embodiment, $R^1$ is substituted by $C_{1-6}$ alkoxy. In one aspect of this embodiment, $R^1$ is substituted by methoxy.

In a third particular embodiment $R^1$ is substituted by hydroxy.

Typical values of $R^1$ include hydrogen, bromo, chloro, cyano, —$CO_2R^d$, methoxycarbonyl-ethyl, ethoxycarbonylethyl, hydroxybutynyl, chlorophenyl, hydroxyphenyl, methyl-sulphonylphenyl, (methylsulphonyl)methylphenyl, (methylsulphonyl)ethylphenyl, aminomethylphenyl, aminoisopropylphenyl, acetylaminomethylphenyl, acetylphenyl, methoxycarbonylphenyl, aminocarbonylphenyl, aminosulphonylphenyl, acetylaminosulphonylphenyl, (di-(trifluoromethyl))(hydroxy)phenyl, cyanoisopropylphenyl, methoxyazetidinyl, methoxypyrrolidinyl, (methoxycarbonyl)(methyl)pyrrolidinyl, (methoxymethyl)pyrrolidinyl, chloropyridinyl, (chloromethyl)pyridinyl, oxopiperidinyl, (carboxy)piperidinyl, ethoxycarbonylpiperidinyl, methylsulphonylpiperazinyl, morpholinyl, methylsulphonyl-1,2,3,6-tetrahydropyridinyl, acetyl-1,2,3,6-tetrahydropyridinyl, tert-butoxycarbonyl-1,2,3,6-tetrahydropyridinyl, methoxycarbonylmethyl-1,2,3,6-tetrahydropyridinyl, benzofuryl, thienyl, indolyl, pyrazolyl, methylpyrazolyl, methylsulphonylpyrazolyl, methylsulphonylethylpyrazolyl, dimethylpyrazolyl, (methyl) [N-methyl-N-(methylsulfonyl)amino]pyrazolyl, methylindazolyl, dimethylisoxazolyl, hydroxyisopropylthiazolyl, methylimidazolyl, dimethylimidazolyl, pyridinyl, tetrahydropyranylpyridinyl, fluoropyridinyl, cyanopyridinyl, methylpyridinyl, (cyano)(methyl)pyridinyl, dimethylpyridinyl, cyclopropylpyridinyl, trifluoromethylpyridinyl, ethenylpyridinyl, hydroxyisopropylpyridinyl, hydroxymethylpyridinyl, methoxypyridinyl, (methoxy)(methyl)pyridinyl, isopropoxypyridinyl, trifluoroethoxypyridinyl, (methyl)-(trifluoroethoxy)pyridinyl, methylsulphonylpyridinyl, methylsulphonylmethylpyridinyl, oxopyridinyl, (methyl)(oxo)-pyridinyl, (dimethyl)(oxo)pyridinyl, aminopyridinyl, methylaminopyridinyl, dimethyl-aminopyridinyl, methoxyethylaminopyridinyl, N-(hydroxyethyl)-N-(methyl)amino-pyridinyl, methylsulphonylaminopyridinyl, [bis(methylsulphonyl)amino]pyridinyl, carboxypyridinyl, quinolinyl, hydroxypyridazinyl, pyrimidinyl, isopropylpyrimidinyl, fluoroisopropyl-pyrimidinyl, hydroxyisopropylpyrimidinyl, methoxypyrimidinyl, carboxycyclobutyloxy-pyrimidinyl, methylthiopyrimidinyl, methylsulphonylpyrimidinyl, oxopyrimidinyl, aminopyrimidinyl, dimethylaminopyrimidinyl, methoxyethylaminopyrimidinyl, N-(carboxyethyl)-N-(methyl)aminopyrimidinyl, carboxycyclopentylaminopyrimidinyl, carboxycyclopropylmethylaminopyrimidinyl, acetoxyisopropylpyrimidinyl, ethoxycarbonylethylpyrimidinyl, hydroxypyrazinyl, hydroxyisopropylpyrazinyl, pyrrolidinylmethylphenyl, piperazinylmethylphenyl, pyridinylpiperazinyl, carboxy-cyclohexylpyrazolyl, carboxycyclohexylpyridinyl, cyclopropylpyrimidinyl, fluoromethylcyclopropylpyrimidinyl, acetylaminomethylcyclopropylpyrimidinyl, hydroxymethylpyrimidinyl, hydroxycyclobutylpyrimidinyl, (methyl)cyclobutyldiol-pyrimidinyl, carboxy-cyclopentylpyrimidinyl, carboxycyclohexylpyrimidinyl, (carboxy)(methyl)cyclohexyl-pyrimidinyl, (carboxy)(hydroxy)cyclohexylpyrimidinyl, carboxymethylcyclohexyl-pyrimidinyl, ethoxycarbonylcyclohexylpyrimidinyl, (methoxycarbonyl)(methyl)-cyclohexylpyrimidinyl, (ethoxycarbonyl)(methyl)cyclohexylpyrimidinyl, carboxy-cyclohexylpyrazinyl, carboxycyclohexylmethylpyrimidinyl, carboxycyclohexenyl-pyridinyl, carboxycyclohexenylpyrimidinyl, ethoxycarbonylcyclohexenylpyrimidinyl, carboxybicyclo[3.1.0]hexanylpyridinyl, carboxybicyclo[3.1.0]hexenylpyridinyl carboxybicyclo[3.1.0]hexanylpyrimidinyl, ethoxycarbonylbicyclo[3.1.0]hexanylpyrimidinyl, carboxybicyclo[4.1.0]heptanyl-pyrimidinyl, carboxybicyclo[2.2.2]octanylpyrimidinyl, pyrrolidinylpyridinyl, hydroxypyrrolidinylpyridinyl, hydroxytetrahydropyranylpyridinyl, piperidinylpyridinyl, acetylpiperidinylpyridinyl, (carboxy)(methyl)piperidinylpyridinyl, [(carboxy)(methyl)-piperidinyl](fluoro)pyridinyl, [(carboxy)(methyl)piperidinyl](chloro)pyridinyl, piperazinylpyridinyl, (methyl)(piperazinyl)pyridinyl, cyanoethylpiperazinylpyridinyl, trifluoroethylpiperazinylpyridinyl, methylsulphonylpiperazinylpyridinyl, methylsulphonylethylpiperazinylpyridinyl, oxopiperazinylpyridinyl, acetylpiperazinylpyridinyl, (tert-butoxycarbonylpiperazinyl)pyridinyl, (tert-butoxycarbonylpiperazinyl)(methyl)pyridinyl, methylpiperazinylpyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinylpyridinyl, (tert-butoxycarbonyl)-3,6-dihydropyridine, oxothiomorpholinylpyridinyl, dioxothiomorpholinylpyridinyl, oxodiazepanyl-pyridinyl, tetrahydropyranylpyrimidinyl, fluorooxetanylpyrimidinyl, hydroxyoxetanylpyrimidinyl, hydroxyazetidinyl-pyrimidinyl, (hydroxy)(methyl)azetidinylpyrimidinyl, (hydroxy)(trifluoromethyl)azetidinylpyrimidinyl, carboxyazetidinylpyrimidinyl, (tert-butoxycarbonyl)(hydroxy)azetidinylpyrimidinyl, tetrazolylazetidinylpyrimidinyl, hydroxytetrahydrofuranylpyrimidinyl, hydroxypyrrolidinylpyrimidinyl, carboxypyrrolidinylpyrimidinyl, (carboxy)(methyl)pyrrolidinylpyrimidinyl, carboxymethyl-pyrrolidinylpyrimidinyl, ethoxycarbonylpyrrolidinylpyrimidinyl, fluoro-tetrahydropyranylpyrimidinyl, hydroxytetrahydropyranylpyrimidinyl, (hydroxy)dioxidotetrahydrothiopyranyl)pyrimidinyl, piperidinylpyrimidinyl, difluoropiperidinyl-pyrimidinyl, (cyano)(methyl)piperidinylpyrimidinyl, (hydroxy)(nitromethyl)piperidinyl-pyrimidinyl, (hydroxy)(methyl)piperidinylpyrimidinyl, (hydroxy)(trifluoromethyl)-piperidinylpyrimidinyl, (hydroxymethyl)(methyl)piperidinylpyrimidinyl, methylsulphonylpiperidinylpyrimidinyl, oxopiperidinylpyrimidinyl, (formyl)(methyl)-piperidinylpyrimidinyl, carboxypiperidinylpyrimidinyl, (carboxy)(fluoro)piperidinyl-pyrimidinyl, (carboxy)(methyl)piperidinylpyrimidinyl, (carboxy)(ethyl)piperidinyl-pyrimidinyl, (carboxy)(trifluoromethyl)piperidinylpyrimidinyl, (carboxy)(hydroxy)-piperidinylpyrimidinyl, (carboxy)(hydroxymethyl)piperidinylpyrimidinyl, (carboxy)-(methoxy)piperidinylpyrimidinyl, (amino)(carboxy)piperidinylpyrimidinyl, carboxy-methylpiperidinylpyrimidinyl, methoxycarbonylpiperidinylpyrimidinyl, ethoxycarbonyl-piperidinylpyrimidinyl, (ethoxycarbonyl)(fluoro)piperidinylpyrimidinyl, (methoxy-carbonyl)(methyl)piperidinylpyrimidinyl, (ethyl)(methoxycarbonyl)piperidinyl-pyrimidinyl, (isopropyl)(methoxycarbonyl)piperidinylpyrimidinyl, (ethoxycarbonyl)-(methyl)piperidinylpyrimidinyl, (n-butoxycarbonyl)(methyl)piperidinylpyrimidinyl, (ethoxycarbonyl)(trifluoromethyl)piperidinylpyrimidinyl, (ethoxycarbonyl)-(hydroxymethyl)piperidinylpyrimidinyl, (methoxy)(methoxycarbonyl)piperidinyl-pyrimidinyl, (carboxy)(methoxycarbonyl)piperidinylpyrimidinyl, (methyl)-(morpholinylethoxycarbonyl)piperidinylpyrimidinyl, ethoxycarbonylmethylpiperidinyl-pyrimidinyl, methylsulphonylaminocarbonylpiperidinylpyrimidinyl, acetylpiperidinylpyrimidinyl, acetylamino-sulphonylpiperidinylpyrimidinyl, methoxyaminocarbonylpiperidinylpyrimidinyl, tetrazolylpiperidinylpyrimidinyl, hydroxyoxadiazolylpiperidinylpyrimidinyl, amino-sulphonylpiperidinylpyrimidinyl, piperazinylpyrimidinyl, methylsulphonylpiperazinyl-pyrimidinyl, oxopiperazinylpyrimidinyl, carboxypiperazinylpyrimidinyl, carboxyethyl-piperazinylpyrimidinyl, tert-butoxycarbonylpiperazinylpyrimidinyl, tetrazolylmethyl-piperazinylpyrimidinyl, trioxohexahydro-[1,2,5]thiadiazolo[2,3-a]pyrazinylpyrimidinyl, morpholinylpyrimidinyl, dimethylmorpholinylpyrimidinyl, hydroxymethylmorpholinyl-pyrimidinyl, carboxymorpholinylpyrimidinyl, (carboxy)(methyl)morpholinylpyrimidinyl, carboxymethylmorpholinylpyrimidinyl, thiomorpholinylpyrimidinyl, oxo-thiomorpholinylpyrimidinyl, dioxo-thiomorpholinylpyrimidinyl, carboxyazepanylpyrimidinyl, carboxyoxazepanyl-pyrimidinyl, oxodiazepanylpyrimidinyl, (oxodiazepanyl)(trifluoromethyl)pyrimidinyl, (oxodiazepanyl)(methoxy)pyrimidinyl, (methyl)(oxo)diazepanylpyrimidinyl, dioxo-thiadiazepanylpyrimidinyl, hydroxyoxetanylpyrazinyl, (carboxy)(methyl)piperidinyl-pyrazinyl, (ethoxycarbonyl)(methyl)piperidinylpyrazinyl, morpholinylmethylthienyl, morpholinylethylpyrazolyl, isopropylmethylpyrazolyl, carboxy-3-azabicyclo[3.1.0]hexanylpyridinyl, carboxy-3-azabicyclo[3.1.0]hexanylpyridazinyl, carboxy-3-azabicyclo[3.1.0]hexanylpyrimidinyl, (carboxy)(methyl)-3-azabicyclo[3.1.0]hexanylpyrimidinyl, methoxycarbonyl-3-azabicyclo[3.1.0]hexanylpyrimidinyl, ethoxycarbonyl-3-azabicyclo[3.1.0]hexanyl-pyrimidinyl, 2-oxa-5-azabicyclo[2.2.1]heptanylpyrimidinyl, carboxy-2-oxa-5-azabicyclo-[2.2.1]heptanylpyrimidinyl, carboxy-3-azabicyclo[3.1.1]heptanylpyrimidinyl, carboxy-3-azabicyclo[4.1.0]heptanylpyridinyl, carboxy-3-azabicyclo[4.1.0]heptanylpyrimidinyl, methoxycarbonyl-3-azabicyclo[4.1.0]heptanylpyrimidinyl, ethoxycarbonyl-3-azabicyclo-[4.1.0]heptanylpyrimidinyl, (hydroxy)(methyl)(oxo)-2-oxabicyclo[2.2.2]octanyl-pyrimidinyl, carboxy-3-azabicyclo[3.2.1]octanylpyrimidinyl, methoxycarbonyl-3-azabicyclo[3.2.1]octanylpyrimidinyl, oxo-8-azabicyclo[3.2.1]octanylpyrimidinyl, ethoxycarbonylmethylidenyl-8-azabicyclo[3.2.1]octanylpyrimidinyl, 3-oxa-8-azabicyclo-[3.2.1]octanylpyrimidinyl, 3-carboxy-8-azabicyclo-[3.2.1]-octanylpyrimidinyl, 3-(dimethylaminocarbonyl)-8-azabicyclo-[3.2.1]octanylpyrimidinyl,oxo-3,6-diazabicyclo[3.2.2]nonanylpyrimidinyl, 3,7-dioxa-9-azabicyclo[3.3.1]-nonanylpyrimidinyl, carboxy-3-oxa-7-azabicyclo[3.3.1]nonanylpyrimidinyl, carboxy-5-azaspiro[2.3]hexanylpyrimidinyl, (carboxy)(methyl)-5-azaspiro[2.3]hexanylpyrimidinyl, carboxy-5-azaspiro[2.4]heptanyl-pyrimidinyl, carboxy-2-azaspiro[3.3]heptanylpyrimidinyl, 2-oxa-6-azaspiro[3.3]heptanyl-pyrimidinyl, 2-oxa-6-azaspiro[3.4]octanylpyrimidinyl, 2-oxa-6-azaspiro[3.5]nonanyl-pyrimidinyl, 2-oxa-7-azaspiro[3.5]nonanylpyrimidinyl, (dioxo)(methyl)-2,4,8-triazaspiro[4.5]decanylpyrimidinyl, 3,6-epiminofuro [3.2-b]furanyl-pyrimidinyl, 5-(methyl-1H-1,2,4-triazol-3yl)phenyl, dihydroisoindolyl, (methylsulphonyl)dihydroisoindolyl (tetrahydrothiopenyl)pyrazolyl, methylsulphoximinylphenyl, (imino)(oxo)thiazinanyl-pyrimidinyl, (oxo)thiazinanyl-pyrimidinyl and (dioxo)thiazinanyl-pyrimidinyl.

Illustrative values of $R^1$ include bromo, (methoxy)pyridinyl, morpholinyl-pyrimidinyl and 2-oxo-(1H)-pyridinyl. Illustrative values of $R^1$ additionally include hydroxyisopropylpyridinyl, in particular, 2-hydroxyprop-2-yl-pyridinyl.

Typically, $R^2$ represents hydrogen, halogen or $C_{1-6}$ alkyl.

In a first embodiment, $R^2$ represents hydrogen. In a second embodiment, $R^2$ represents halogen. In one aspect of that embodiment, $R^2$ represents fluoro.

In a third embodiment, $R^2$ represents $C_{1-6}$ alkyl. In another particular aspect of that embodiment, $R^2$ represents methyl.

In a particular embodiment, $R^2$ represents hydrogen.

Typically, $R^3$ represents hydrogen, halogen or $C_{1-6}$ alkyl.

In a first embodiment, $R^3$ represents hydrogen. In a second embodiment, $R^3$ represents halogen. In one aspect of that embodiment, $R^3$ represents fluoro.

In a third embodiment, $R^3$ represents $C_{1-6}$ alkyl. In another particular aspect of that embodiment, $R^3$ represents methyl.

In a particular embodiment, $R^3$ represents hydrogen.

Generally, $R^4$ represents hydrogen, hydroxy, halogen, trifluoromethyl, $-NR^bR^c$, $-NR^cC(O)R^d$, $-NHS(O)_2R^e$, $-S(O)_2R^a$, $-S(O)(N-R^d)R^a$ or $-O-(CO)-R^d$; or $C_{1-6}$ alkoxy, $C_{1-6}$ alkyl, $C_{2-6}$ alkynyl, heteroaryl, any of which groups may be optionally substituted by one or more substituents.

Typically, $R^4$ represents hydrogen, hydroxy, halogen, or trifluoromethyl.

In a particular embodiment, $R^4$ represents hydrogen.

In an alternative embodiment, $R^4$ and Y together with the carbon to which they are attached form a $C_{3-7}$ cycloalkyl.

In another alternative embodiment, $R^4$ and Y together with the carbon to which they are attached form a $C_{3-7}$ heterocycloalkyl. In one particular aspect according to this embodiment, $R^4$ and Y together with the carbon to which they are attached form a dihydrobenzofuran. In a second particular aspect according to this embodiment, $R^4$ and Y together with the carbon to which they are attached form a 3H-benzofuranone. In a third particular aspect according to this embodiment, $R^4$ and Y together with the carbon to which they are attached form a dihydroisoindole. In a fourth particular aspect according to this embodiment, $R^4$ and Y together with the carbon to which they are attached form a dihydroisoindolone.

Typically, $R^{5a}$ represents hydrogen, hydroxy, halogen, trifluoromethyl, —$NR^bR^c$, $S(O)_2R^a$, —$OR^a$, or —O—(CO)—$R^d$; or $C_{1-6}$ alkyl which group may be optionally substituted.

Suitable examples of optional substituents on $R^{5a}$ include one, two or three substituents independently selected from halogen, hydroxy, trifluoromethyl, $C_{1-6}$ alkyl, $C_{1-6}$ alkoxy, $C_{2-6}$ alkylcarbonyl, $C_{2-6}$ alkyloxycarbonyl, (hydroxy)$C_{1-6}$ alkyl, $(C_{3-7})$cycloalkyl, $C_{1-6}$ alkylsulphonyl, $(C_{1-6})$alkylsulphonyl$(C_{1-6})$alkyl, di$(C_{1-6})$alkylaminocarbonyl, oxo, and carboxy.

Typical examples of particular substituents on $R^{5a}$ include one, two or three substituents independently selected from fluoro, chloro, fluoromethyl, fluoroisopropyl, cyano, cyanoethyl, nitromethyl, methyl, ethyl, isopropyl, isopropylmethyl, trifluoromethyl, trifluoroethyl, ethenyl, hydroxy, hydroxymethyl, hydroxyisopropyl, methoxy, isopropoxy, trifluoro-ethoxy, carboxycyclobutyloxy, methylthio, methylsulphonyl, methylsulphonylmethyl, methylsulphonylethyl, oxo, amino, aminomethyl, aminoisopropyl, methylamino, dimethylamino, methoxyethylamino, N-(hydroxyethyl)-N-(methyl)amino, acetylaminomethyl, methylsulphonylamino, N-methyl-N-(methylsulphonyl)amino, bis(methylsulphonyl)amino, N-(carboxyethyl)-N-(methyl)amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxy-carbonylmethyl, ethoxycarbonylethyl, morpholinylethoxycarbonyl, ethoxycarbonyl-methylidenyl, methylsulphonylaminocarbonyl, acetylaminosulphonyl, methoxyaminocarbonyl, tetrazolyl, tetrazolylmethyl, hydroxyoxadiazolyl, aminocarbonyl, amino-sulphonyl, methylsulphoximinyl and (methyl)(N-methyl)sulphoximinyl.

In a first embodiment, $R^{5a}$ represents hydrogen. In a second embodiment, $R^{5a}$ represents hydroxy. In a third embodiment, $R^{5a}$ represents halogen. In one aspect of this embodiment, $R^{5a}$ represents fluoro. In a fourth embodiment, $R^{5a}$ represents trifluoromethyl. In a fifth embodiment, $R^{5a}$ represents —$NR^bR^c$. In one aspect of that embodiment, $R^{5a}$ represents —$NH_2$. In a sixth embodiment, $R^{5a}$ represents —$NR^cC(O)R^d$. In a seventh embodiment, $R^{5a}$ represents —C(O)—$NR^cR^d$. In an eighth embodiment, $R^{5a}$ represents —$NHS(O)_2R^e$. In a ninth embodiment, $R^{5a}$ represents —S—$R^a$. In a tenth embodiment, $R^{5a}$ represents —S(O)—$R^a$. In an eleventh embodiment, $R^{5a}$ represents —$S(O)_2R^a$. In a particular aspect of this embodiment, $R^{5a}$ represents —$S(O)_2$—$CH_3$. In a twelfth embodiment, $R^{5a}$ represents —S(O)(N—$R^d$)$R^a$. In a thirteenth embodiment, $R^{5a}$ represents —$S(O)_2$(N—$R^d$). In a fourteenth embodiment, $R^{5a}$ represents —$OR^a$. In one aspect of this embodiment, $R^a$ is an optionally substituted $C_{1-6}$ alkyl. In second aspect of this embodiment $R^a$ is an optionally substituted aryl. In a third aspect of this embodiment, $R^a$ is an heteroaryl. In a fifteenth embodiment, $R^{5a}$ represents —O—(CO)—$R^d$. In a particular aspect of this embodiment, $R^{5a}$ represents —O—(CO)—$CH_3$. In a sixteenth embodiment, —C(O)—$OR^d$. In a seventeenth embodiment, $R^{5a}$ represents optionally substituted $C_{1-6}$ alkyl. In one aspect of that embodiment, $R^{5a}$ represents substituted $C_{1-6}$ alkyl. In a second aspect of this embodiment, $R^{5a}$ represents unsubstituted $C_{1-6}$ alkyl. In a particular aspect of this embodiment, $R^{5a}$ represents methyl. In an eighteenth embodiment, $R^{5a}$ represents an optionally substituted $C_{2-6}$ alkynyl. In a nineteenth embodiment, $R^{5a}$ represents an optionally substituted heteroaryl.

In a twentieth embodiment $R^{5a}$ represents an optionally substituted aryl. In a twenty-first embodiment, $R^{5a}$ represents an optionally substituted $C_{2-6}$ alkenyl.

In a twenty-second embodiment, $R^{5a}$ represents cyano.

In a selected embodiment, $R^{5a}$ represents hydrogen, hydroxy or —$OR^a$.

In a particular embodiment, $R^{5a}$ represents hydrogen.

Typically, $R^{5b}$ represents hydrogen, hydroxy, halogen, trifluoromethyl, —$NR^bR^c$, —$S(O)_2R^a$, —$OR^a$, or —O—(CO)—$R^d$; or $C_{1-6}$ alkyl which group may be optionally substituted.

Suitably, $R^{5b}$ represents hydrogen, hydroxy, halogen, cyano, or trifluoromethyl; or $C_{1-6}$ alkyl, which group may be optionally substituted by one or more substituents.

Suitable examples of optional substituents on $R^{5b}$ include one, two or three substituents independently selected from halogen, hydroxy, trifluoromethyl, $C_{1-6}$ alkyl, $C_{1-6}$ alkoxy, $C_{2-6}$ alkylcarbonyl, $C_{2-6}$ alkyloxycarbonyl, (hydroxy)$C_{1-6}$ alkyl, $(C_{3-7})$cycloalkyl, $C_{1-6}$ alkylsulphonyl, $(C_{1-6})$alkylsulphonyl$(C_{1-6})$alkyl, di$(C_{1-6})$alkylaminocarbonyl, oxo, and carboxy.

Typical examples of particular substituents on $R^{5b}$ include one, two or three substituents independently selected from fluoro, chloro, fluoromethyl, fluoroisopropyl, cyano, cyanoethyl, nitromethyl, methyl, ethyl, isopropyl, isopropylmethyl, trifluoromethyl, trifluoroethyl, ethenyl, hydroxy, hydroxymethyl, hydroxyisopropyl, methoxy, isopropoxy, trifluoro-ethoxy, carboxycyclobutyloxy, methylthio, methylsulphonyl, methylsulphonylmethyl, methylsulphonylethyl, oxo, amino, aminomethyl, aminoisopropyl, methylamino, dimethylamino, methoxyethylamino, N-(hydroxyethyl)-N-(methyl)amino, acetylaminomethyl, methylsulphonylamino, N-methyl-N-(methylsulphonyl)amino, bis(methylsulphonyl)amino, N-(carboxyethyl)-N-(methyl)amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxy-carbonylmethyl, ethoxycarbonylethyl, morpholinylethoxycarbonyl, ethoxycarbonyl-methylidenyl, methylsulphonylaminocarbonyl, acetylaminosulphonyl, methoxyaminocarbonyl, tetrazolyl, tetrazolylmethyl, hydroxyoxadiazolyl, aminocarbonyl, amino-sulphonyl, methylsulphoximinyl and (methyl)(N-methyl)sulphoximinyl.

In a first embodiment, $R^{5b}$ represents hydrogen. In a second embodiment, $R^{5b}$ represents hydroxy. In a third embodiment, $R^{5b}$ represents halogen. In one aspect of this embodiment, $R^{5b}$ represents fluoro. In a fourth embodiment, $R^{5b}$ represents trifluoromethyl. In a fifth embodiment, $R^{5b}$ represents —$NR^bR^c$. In one aspect of that embodiment, $R^{5b}$ represents —$NH_2$. In a sixth embodiment, $R^{5b}$ represents —$NR^cC(O)R^d$. In a seventh embodiment, $R^{5b}$ represents —C(O)—$NR^cR^d$. In an eighth embodiment, $R^{5b}$ represents —$NHS(O)_2R^e$. In a ninth embodiment, $R^{5a}$ represents —S—$R^a$. In a tenth embodiment, $R^{5b}$ represents —S(O)—$R^a$. In an eleventh embodiment, $R^{5b}$ represents —$S(O)_2R^a$. In a particular aspect of this embodiment, $R^{5b}$ represents —$S(O)_2$—$CH_3$. In a twelfth embodiment, $R^{5b}$ represents —S(O)(N—$R^d$)$R^a$. In a thirteenth embodiment, $R^{5b}$ represents —$S(O)_2$(N—$R^d$). In a fourteenth embodiment, $R^{5b}$ represents —$OR^a$. In one aspect of this embodiment, $R^a$ is an optionally substituted $C_{1-6}$ alkyl. In second aspect of this embodiment $R^a$ is an optionally substituted aryl. In a third aspect of this embodiment, $R^a$ is an heteroaryl. In a fifteenth embodiment, $R^{5b}$ represents —O—(CO)—$R^d$. In a particular aspect of this embodiment, $R^{5a}$ represents —O—(CO)—CH$_3$. In a sixteenth embodiment, —C(O)—OR$^d$. In a seventeenth embodiment, $R^{5b}$ represents optionally substituted $C_{1-6}$ alkyl. In one aspect of that embodiment, $R^{5b}$ represents substituted $C_{1-6}$ alkyl. In a second aspect of this embodiment, $R^{5b}$ represents unsubstituted $C_{1-6}$ alkyl. In a particular aspect of this embodiment, $R^{5b}$ represents methyl. In an eighteenth embodiment, $R^{5b}$ represents an optionally substituted $C_{2-6}$ alkynyl. In a nineteenth embodiment, $R^{5b}$ represents an optionally substituted heteroaryl. In a twentieth embodiment $R^{5b}$ represents an optionally substituted aryl. In a twenty-first embodiment, $R^{5b}$ represents an optionally substituted $C_{2-6}$ alkenyl. In a twenty-second embodiment, $R^{5b}$ represents cyano.

In a particular embodiment, $R^{5b}$ represents hydrogen.

In an alternative embodiment, $R^{5a}$ and $R^{5b}$ when taken together with the carbon to which they are attached represent a carbonyl, thiocarbonyl or —C=N—OH.

In one aspect of that alternative embodiment, $R^{5a}$ and $R^{5b}$ when taken together with the carbon to which they are attached represent a carbonyl.

In a second aspect of that alternative embodiment, $R^{5a}$ and $R^{5b}$ when taken together with the carbon to which they are attached represent a thiocarbonyl.

In another aspect of that alternative embodiment, $R^{5a}$ and $R^{5b}$ when taken together with the carbon to which they are attached represent —C=N—OH.

Typical examples of suitable substituents on $R^a$, $R^b$, $R^c$, $R^d$ or $R^e$, or on the heterocyclic moiety —NR$^b$R$^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$) alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino, aminocarbonyl, $C_{1-6}$ alkylaminocarbonyl and di($C_{1-6}$)alkylaminocarbonyl.

Typical examples of specific substituents on $R^a$, $R^b$, $R^c$, $R^d$ or $R^e$, or on the heterocyclic moiety —NR$^b$R$^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, tert-butoxycarbonylamino, acetylaminomethyl, methylsulphonylamino, aminocarbonyl, methylaminocarbonyl and dimethylaminocarbonyl.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy and oxo. Additional examples of suitable substituents on $R^a$ include aminocarbonyl.

Selected examples of specific substituents on $R^a$ include methoxy and oxo. Additional selected examples of suitable substituents on $R^a$ include aminocarbonyl In one embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, especially methyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl. In another embodiment, $R^a$ represents optionally substituted aryl($C_{1-6}$)alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl. In a further embodiment, $R^a$ represents $C_{3-7}$ cycloalkyl. In another further embodiment, $R^a$ represents $C_{3-7}$ heterocycloalkyl, Specific values of $R^a$ include methyl, methoxyethyl, benzyl and dioxoisoindolyl-propyl.

In a particular aspect, $R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents.

Selected values of $R^b$ include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-($C_{1-6}$) alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylamino-ethyl, tert-butoxycarbonylaminoethyl, dihydroxypropyl, benzyl, pyrrolidinyl, tert-butoxycarbonylpyrrolidinyl and morpholinylpropyl.

In one embodiment, $R^b$ represents hydrogen. In another embodiment, $R^b$ represents $C_{1-6}$ alkyl, especially methyl.

Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected examples of suitable substituents on $R^c$ include $C_{2-6}$ alkylcarbonyl and $C_{2-6}$ alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl, Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl, homopiperazin-1-yl, (imino)(oxo)thiazinan-4-yl, (oxo)thiazinan-4-yl or (dioxo)thiazinan-4-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonyl-amino, $C_{2-6}$ alkylcarbonylamino($C_{1-6}$)alkyl, $C_{2-6}$ alkoxycarbonylamino, $C_{1-6}$ alkyl-sulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxy-carbonylamino, methylsulphonylamino and aminocarbonyl.

Specific values of the heterocyclic moiety —$NR^bR^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, aminoazetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxo-oxazolidin-3-yl, hydroxyisoxazolidin-2-yl, thiazolidin-3-yl, oxothiazolidin-3-yl, dioxoisothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl, oxohomopiperazin-1-yl, (imino)(oxo)thiazinan-4-yl, (oxo)thiazinan-4-yl or (dioxo)thiazinan-4-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di($C_{1-6}$)alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl.

In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl.

In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl.

In a further embodiment, $R^d$ represents optionally substituted $C_{3-7}$ heterocycloalkyl, e.g. thiazolidinyl or oxo-thiazolidinyl.

Selected examples of specific values for $R^d$ include hydrogen, methyl, acetoxy-methyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Particular examples of selected values for $R^d$ include hydrogen and methyl.

Selected values of $R^{5a}$ include hydrogen, hydroxy, fluoro, trifluoromethyl, —$N(CH_3)_2$, —$NH(CO)CH_3$, —$SO_2$—$CH_3$, —O—(CO)—$CH_3$, methyl, methoxy and (aminocarbonyl)methyloxy.

Selected values of $R^{5b}$ include hydrogen, hydroxy, fluoro, trifluoromethyl, —$N(CH_3)_2$, —$NH(CO)CH_3$, —$SO_2$—$CH_3$, —O—(CO)—$CH_3$, methyl and methoxy.

Illustrative values of $R^{5a}$ include hydrogen, hydroxy and (aminocarbonyl)methyloxy.

Particular values of $R^{5b}$ include hydrogen.

In a particular embodiment, $R^{5a}$ is as defined above and $R^{5b}$ represents hydrogen. In a particular aspect of this embodiment, $R^{5a}$ is hydroxy.

In another particular embodiment $R^{5a}$ is as defined above and $R^{5b}$ represents $C_{1-4}$ alkyl, preferably methyl. In a particular aspect of this embodiment, $R^{5a}$ is hydroxy.

In a further particular embodiment, $R^{5a}$ and $R^{5b}$ independently represent hydrogen.

In yet a further embodiment, $R^{5a}$ represents (aminocarbonyl)methyloxy and $R^{5b}$ represents hydrogen.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

One sub-class of compounds of formula (I) according to the invention is represented by the compounds of formula (IIA) and N-oxides thereof, and pharmaceutically acceptable salts and solvates thereof, and glucuronide derivatives thereof, and co-crystals thereof:

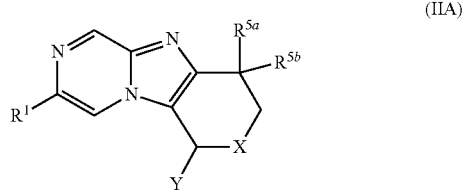

(IIA)

wherein
$R^1$, $R^{5a}$, $R^{5b}$, X and Y are as defined above.

A particular sub-group of the compounds of formula (IIA) is represented by the compounds of formula (IIA-A) and N-oxides thereof, and pharmaceutically acceptable salts and solvates thereof, and glucuronide derivatives thereof, and co-crystals thereof:

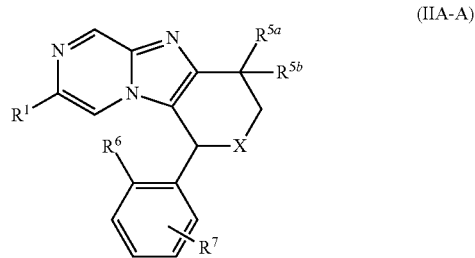

(IIA-A)

wherein
$R^6$ and $R^7$ independently represent hydrogen, halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, arylamino, $C_{2-6}$ alkylcarbonylamino, $C_{1-6}$ alkylsulfonylamino, formyl, $C_{2-6}$ alkylcarbonyl, $C_{3-6}$cycloalkylcarbonyl, $C_{3-6}$heterocycloalkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl; and X, $R^1$, $R^{5a}$ and $R^{5b}$ are as defined above.

Typically, $R^6$ and $R^7$ may independently represent hydrogen, fluoro, chloro, 5 bromo, cyano, nitro, methyl, isopropyl, trifluoromethyl, hydroxy, methoxy, difluoro-methoxy, trifluoromethoxy, methylthio, methylsulfinyl, methylsulfonyl, amino, methyl-amino, tert-butylamino, dimethylamino, phenylamino, acetylamino, methylsulfonylamino, formyl, acetyl, cyclopropylcarbonyl, azetidinylcarbonyl, pyrrolidinylcarbonyl, piperidinyl-carbonyl, piperazinylcarbonyl, morpholinylcarbonyl, carboxy, methoxycarbonyl, amino-10 carbonyl, methylaminocarbonyl, dimethylaminocarbonyl, aminosulfonyl, methylamino-sulfonyl and dimethylaminosulfonyl.

Typical values of $R^6$ include hydrogen, halogen, $C_{1-6}$ alkyl, trifluoromethyl, $C_{1-6}$ alkoxy, difluoromethoxy and trifluoromethoxy.

In a first embodiment, $R^6$ represents hydrogen. In a second embodiment, $R^6$ represents halogen. In a first aspect of that embodiment, $R^6$ represents fluoro. In a second aspect of that embodiment, $R^6$ represents chloro. In a third embodiment, $R^6$ represents $C_{1-6}$ alkyl. In one aspect of that embodiment, $R^6$ represents methyl. In a fourth embodiment, $R^6$ represents trifluoromethyl. In a fifth embodiment, $R^6$ represents $C_{1-6}$ alkoxy. In one aspect of that embodiment, $R^6$ represents methoxy. In a sixth embodiment, $R^6$ represents difluoromethoxy. In a seventh embodiment, $R^6$ represents trifluoromethoxy.

Selected values of $R^6$ include hydrogen, fluoro, chloro, methyl, trifluoromethyl, methoxy, difluoromethoxy and trifluoromethoxy.

Illustratively, $R^6$ represents difluoromethoxy.

Typical values of $R^7$ include hydrogen, halogen, cyano, $C_{1-6}$ alkyl, trifluoro-methyl, difluoromethoxy and amino.

In a first embodiment, $R^7$ represents hydrogen. In a second embodiment, $R^7$ represents halogen. In a first aspect of that embodiment, $R^7$ represents fluoro. In a second aspect of that embodiment, $R^7$ represents chloro. In a third embodiment, $R^7$ represents cyano. In a fourth embodiment, $R^7$ represents $C_{1-6}$ alkyl. In one aspect of that embodiment, $R^7$ represents methyl. In a fifth embodiment, $R^7$ represents trifluoro-methyl. In a sixth embodiment, $R^7$ represents difluoromethoxy. In a seventh embodiment, $R^7$ represents amino.

Selected values of $R^7$ include hydrogen, fluoro, chloro, cyano, methyl, trifluoro-methyl, difluoromethoxy and amino.

Illustratively, $R^7$ represents hydrogen.

In a particular embodiment, $R^7$ is attached at the para-position of the phenyl ring relative to the integer $R^6$.

In another embodiment, $R^6$ and $R^7$ are attached to the phenyl ring at positions 2 and 6.

In yet another embodiment, $R^6$ and $R^7$ are attached to the phenyl ring at positions 2 and 5.

A particular sub-group of the compounds of formula (IIA-A) above is represented by compounds of formula (IIA-AB), and N-oxides thereof, and pharmaceutically acceptable salts and solvates thereof, and glucuronide derivatives thereof, and co-crystals thereof:

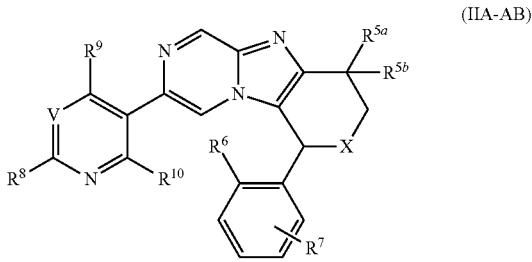

(IIA-AB)

wherein
V represents C—$R^{11}$ or N;
$R^8$ represents hydrogen, halogen, halo($C_{1-6}$)alkyl, cyano, cyano($C_{1-6}$)alkyl, nitro($C_{1-6}$)alkyl, $C_{1-6}$ alkyl, trifluoromethyl, trifluoroethyl, $C_{2-6}$ alkenyl, hydroxy, hydroxy($C_{1-6}$) alkyl, $C_{1-6}$ alkoxy, trifluoroethoxy, carboxy($C_{3-7}$)cycloalkyloxy, $C_{1-6}$ alkylthio, $C_{1-6}$ alkylsulphonyl, aryl-sulphonyl, ($C_{1-6}$)alkylsulphonyl($C_{1-6}$)alkyl, oxo, amino, amino-($C_{1-6}$)

alkyl, $C_{1-6}$ alkylamino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl] amino, ($C_{2-6}$)alkylcarbonylamino($C_{1-6}$)alkyl, $C_{1-6}$ alkylsulphonylamino, N—[($C_{1-6}$)alkyl]-N—[($C_{1-6}$)alkylsulphonyl]amino, bis[($C_{1-6}$)alkyl-sulphonyl]amino, N—[($C_{1-6}$)alkyl]-N-[carboxy($C_{1-6}$)alkyl]amino, carboxy($C_{3-7}$)cycloalkyl-amino, carboxy($C_{3-7}$)cycloalkyl($C_{1-6}$)alkylamino, formyl, $C_{2-6}$ alkylcarbonyl, ($C_{2-6}$)alkyl-carbonyloxy($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl($C_{1-6}$)alkoxycarbonyl, $C_{2-6}$ alkoxycarbonyl-methylidenyl, aminocarbonyl, di($C_{1-6}$)alkylaminocarbonyl, aminosulphonyl, ($C_{1-6}$) alkylsulphoximinyl or [($C_{1-6}$)alkyl][N—($C_{1-6}$)alkyl] sulphoximinyl; ($C_{3-7}$)cycloalkyl, ($C_{3-7}$)cycloalkyl($C_{1-6}$) alkyl, ($C_{4-7}$)cycloalkenyl, ($C_{4-9}$)bicycloalkyl, ($C_{4-9}$) bicycloalkylene, ($C_{3-7}$)heterocycloalkyl, ($C_{3-7}$) heterocycloalkyl($C_{1-6}$)alkyl, ($C_{3-7}$)heterocycloalkenyl, ($C_{4-9}$)heterobicycloalkyl or ($C_{4-9}$)spiroheterocycloalkyl, or heteroaryl, any of which groups may be optionally substituted by one or more substituents;

$R^9$ and $R^{10}$ independently represent hydrogen, halogen, cyano, trifluoromethyl, hydroxy, —$NR^bR^c$, or —$OR^a$; or $C_{1-6}$ alkyl or $C_{1-6}$ alkylsulphonyl;

$R^{11}$ represents hydrogen, halogen or $C_{1-6}$ alkyl; and

X, $R^a$, $R^b$, $R^c$ $R^{5a}$, $R^{5b}$, $R^6$ and $R^7$ are as defined above.

In one embodiment, V represents C—$R^{11}$. In another embodiment, V represents N.

Typically, $R^8$ represents hydrogen, halogen, halo($C_{1-6}$) alkyl, cyano, $C_{1-6}$ alkyl, trifluoromethyl, $C_{2-6}$ alkenyl, hydroxy, hydroxy($C_{1-6}$)alkyl, $C_{1-6}$ alkoxy, trifluoroethoxy, carboxy($C_{3-7}$)cycloalkyloxy, $C_{1-6}$ alkylthio, $C_{1-6}$ alkylsulphonyl, arylsulphonyl, ($C_{1-6}$)alkylsulphonyl($C_{1-6}$)alkyl, amino, amino($C_{1-6}$)alkyl, $C_{1-6}$ alkylamino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl]-amino, N—[($C_{1-6}$)alkyl]-N-[carboxy($C_{1-6}$)alkyl]amino, carboxy($C_{3-7}$)cycloalkylamino, carboxy($C_{3-7}$)cycloalkyl($C_{1-6}$)alkylamino, $C_{1-6}$ alkylsulphonylamino, ($C_{2-6}$)alkylcarbonyl-oxy($C_{1-6}$)alkyl, carboxy, morpholinyl($C_{1-6}$)alkoxycarbonyl, $C_{2-6}$ alkoxycarbonyl($C_{1-6}$)alkyl, $C_{2-6}$ alkoxycarbonylmethylidenyl, di($C_{1-6}$)alkylaminocarbonyl, or ($C_{1-6}$)alkylsulphoximinyl; or $R^9$ represents ($C_{3-7}$)cycloalkyl, ($C_{3-7}$)cycloalkyl-($C_{1-6}$) alkyl, ($C_{4-7}$)cycloalkenyl, ($C_{4-9}$)bicycloalkyl, ($C_{3-7}$)heterocycloalkyl, ($C_{4-9}$)heterobicycloalkyl ($C_{4-9}$)spiroheterocycloalkyl, ($C_{4-9}$)bicycloalkylene or heteroaryl, any of which groups may be optionally substituted by one or more substituents.

Typically, $R^8$ represents ($C_{1-6}$)alkyl, halo($C_{1-6}$)alkyl, (hydroxy)$C_{1-6}$ alkyl, amino($C_{1-6}$)alkyl, $C_{1-6}$ alkoxy, arylsulphonyl, $C_{1-6}$ alkylsulphonyl, ($C_{1-6}$)alkylsulphonyl($C_{1-6}$)alkyl, $C_{2-6}$ alkylcarbonylamino($C_{1-6}$)alkyl, ($C_{1-6}$)alkylsulphoximinyl, carboxy, oxo, or $C_{2-6}$ alkyloxycarbonyl; or $R^8$ represents ($C_{3-7}$)cycloalkyl, ($C_{3-7}$)heterocycloalkyl, or heteroaryl, any of which groups may be optionally substituted by one or more substituents.

In a first embodiment, $R^8$ represents (hydroxy)$C_{1-6}$ alkyl. In one aspect of that embodiment, $R^8$ represents (hydroxy) isopropyl.

In a second embodiment, $R^8$ represents hydroxy.

In a third embodiment, $R^8$ represents $C_{1-6}$ alkoxy. In one aspect of that embodiment $R^8$ represents methoxy.

In a fourth embodiment, $R^8$ represents ($C_{3-7}$)heterocycloalkyl. In one aspect of that embodiment, $R^8$ represents morpholinyl.

In a fifth embodiment, $R^8$ represents (amino)$C_{1-6}$ alkyl. In one aspect of that embodiment, $R^8$ represents (amino)isopropyl Suitably, $R^8$ represents hydroxy, $C_{1-6}$ alkoxy, ($C_{3-7}$)heterocycloalkyl. (hydroxy) $C_{1-6}$alkyl and (amino) $C_{1-6}$alkyl.

Illustratively, $R^8$ represents hydroxy, $C_{1-6}$ alkoxy or ($C_{3-7}$)heterocycloalkyl. Illustratively, $R^8$ represents additionally (hydroxy)$C_{1-6}$alkyl.

Selected values of $R^8$ include hydrogen, isopropyl, isopropylmethyl, hydroxy, hydroxymethyl, hydroxyisopropyl, aminoisopropyl, chloromethyl, methoxy, carboxy-cyclobutyloxy, methylthio, methylsulphonyl, methylsulphonylmethyl, methylamino, N-[carboxyethyl]-N-methyl-amino, carboxycyclopentylamino, carboxycyclopropylmethyl-amino, methylsulfoximinyl, ethoxycarbonyl-ethyl, cyclopropyl, cyclobutyl, cyclopentyl, cyclohexyl, cyclohexylmethyl, cyclohexenyl, bicyclo[3.1.0]hexanyl, bicyclo[3.1.0] hexenyl bicyclo[4.1.0]heptanyl, bicyclo[2.2.2]-octanyl, oxetanyl, azetidinyl, tetrahydrofuranyl, pyrrolidinyl, tetrahydropyranyl, tetrahydro-thiopyranylpyrimidinyl, piperidinyl, piperazinyl, hexahydro-[1,2,5]thiadiazolo[2,3-a]pyrazinyl, morpholinyl, thiomorpholinyl, azepanyl, oxazepanyl, diazepanyl, thiadiazepanyl, 3-azabicyclo[3.1.0]-hexanyl, 2-oxa-5-azabicyclo[2.2.1]heptanyl, 3-azabicyclo[3.1.1]heptanyl, 3-azabicyclo-[4.1.0]heptanyl, 2-oxabicyclo[2.2.2]octanyl, 3-azabicyclo[3.2.1]octanyl, 8-azabicyclo-[3.2.1]octanyl, 3-oxa-8-azabicyclo[3.2.1]octanyl, 3,6-diazabicyclo [3.2.2]nonanyl, 3-oxa-7-azabicyclo[3.3.1]nonanyl, 5-azaspiro[2.3]hexanyl, 5-azaspiro[2.4]heptanyl, 2-azaspiro-[3.3]heptanyl, 3,7-dioxa-9-azabicyclo[3.3.1]-nonanyl, epiminofuro [3.2-b]furanyl, (imino)(oxo)thiazinanyl, (oxo)thiazinanyl, (dioxo)thiazinanyl or triazolyl, any of which groups may be optionally substituted by one or more substituents.

Examples of optional substituents which may be present on $R^8$ include one, two or three substituents independently selected from halogen, halo($C_{1-6}$)alkyl, cyano, cyano-($C_{1-6}$) alkyl, nitro, nitro($C_{1-6}$)alkyl, $C_{1-6}$ alkyl, trifluoromethyl, trifluoroethyl, $C_{2-6}$ alkenyl, hydroxy, hydroxy($C_{1-6}$)alkyl, $C_{1-6}$ alkoxy, difluoromethoxy, trifluoromethoxy, trifluoroethoxy, $C_{1-6}$ alkylthio, $C_{1-6}$ alkylsulphonyl, ($C_{1-6}$)alkylsulphonyl($C_{1-6}$)alkyl, oxo, amino, $C_{1-6}$ alkylamino, di($C_{1-6}$) alkylamino, $C_{2-6}$ alkylcarbonylamino, ($C_{2-6}$) alkylcarbonylamino-($C_{1-6}$)alkyl, $C_{2-6}$ alkoxycarbonylamino, $C_{1-6}$ alkylsulphonylamino, formyl, $C_{1-6}$ alkylcarbonyl, carboxy, carboxy($C_{1-6}$)alkyl, $C_{2-6}$ alkoxycarbonyl, morpholinyl-($C_{1-6}$)alkoxycarbonyl, $C_{2-6}$ alkoxycarbonyl($C_{1-6}$)alkyl, $C_{2-6}$ alkoxycarbonylmethylidenyl, a carboxylic acid isostere or prodrug moiety Ω as defined herein, —($C_{1-6}$)alkyl-Ω, amino-carbonyl, $C_{1-6}$ alkylaminocarbonyl, di($C_{1-6}$)alkylaminocarbonyl, aminosulphonyl, di($C_{1-6}$)alkylaminosulphonyl, ($C_{1-6}$)alkylsulphoximinyl and [($C_{1-6}$)alkyl][N—($C_{1-6}$) alkyl]-sulphoximinyl.

Selected examples of optional substituents on $R^8$ include one, two or three substituents independently selected from halogen, cyano, trifluoromethyl, hydroxy, $C_{1-6}$ alkyl, $C_{1-6}$ alkoxy, $C_{1-6}$ alkylsulphonyl, ($C_{1-6}$)alkylsulphoximinyl, $C_{1-6}$ alkylcarbonyl, $C_{1-6}$ alkoxycarbonyl, oxo and carboxy.

Suitable examples of particular substituents on $R^8$ include one, two or three substituents independently selected from fluoro, fluoromethyl, chloro, bromo, cyano, cyanomethyl, cyanoethyl, nitro, nitromethyl, methyl, ethyl, isopropyl, cyclopropyl, trifluoromethyl, trifluoroethyl, ethenyl, hydroxy, hydroxymethyl, methoxy, ethoxy, difluoromethoxy, trifluoromethoxy, trifluoroethoxy, methylthio, methylsulphonyl, methylsulphonylmethyl, methylsulphonylethyl, oxo, amino, methylamino, dimethylamino, acetylamino, acetyl-aminomethyl, methoxycarbonylamino, ethoxycarbonylamino, tert-butoxycarbonylamino, methylsulphonylamino, formyl, acetyl, carboxy, carboxymethyl, carboxyethyl, methoxycarbonyl, ethoxycarbonyl, n-butoxycarbonyl, tert-butoxycarbonyl, morpholinyl-ethoxycarbonyl, methoxycarbonylmethyl, ethoxycarbonylmethyl, ethoxycarbonylethyl, ethoxycarbonylmethylidenyl, acetylaminosulphonyl, methoxyaminocarbonyl, tetrazolyl, tetrazolylmethyl, hydroxyoxadiazolyl, aminocarbonyl, methylaminocarbonyl, dimethyl-aminocarbonyl, methylsulphonylaminocarbonyl, aminosulphonyl, methylaminosulphonyl, dimethylaminosulphonyl, methylsulphoximinyl and (methyl)(N-methyl)sulphoximinyl.

Selected examples of particular substituents on $R^8$ include one, two or three substituents independently selected from hydroxyl, methyl, trifluoromethyl, tert-butoxycarbonyl, ethoxycarbonyl, methoxycarbonyl, methylsulphonyl, methylsulphonylmethyl, methylsulphonylethyl, methylsulphoximinyl, oxo and carboxy.

Typically, $R^8$ represents hydrogen, fluoro, fluoroisopropyl, cyano, methyl, chloromethyl, isopropyl, trifluoromethyl, ethenyl, hydroxy, hydroxymethyl, hydroxyisopropyl, methoxy, isopropoxy, trifluoro-ethoxy, carboxycyclobutyloxy, methylthio, methylsulphonyl, methylsulphonylmethyl, methylsulphonylethyl, amino, methylamino, dimethylamino, methoxyethylamino, N-(hydroxyethyl)-N-(methyl) amino, N-[carboxy-ethyl]-N-methylamino, carboxycyclopentylamino, carboxycyclopropylmethylamino, methylsulphonylamino, acetoxyisopropyl, carboxy, ethoxycarbonylethyl, cyclopropyl, fluoromethyl-cyclopropyl, acetylaminomethylcyclopropyl, hydroxycyclobutyl, carboxycyclopentyl, carboxycyclohexyl, (carboxy)(methyl)cyclohexyl, (carboxy)(hydroxy)cyclohexyl, carboxymethylcyclohexyl, ethoxycarbonylcyclohexyl, (methoxycarbonyl)(methyl)-cyclohexyl, (ethoxycarbonyl)(methyl)cyclohexyl, carboxycyclohexylmethyl, carboxy-cyclohexenyl, ethoxycarbonylcyclohexenyl, carboxybicyclo[3.1.0]hexanyl, ethoxycarbonylbicyclo[3.1.0]hexanyl, carboxybicyclo[4.1.0]heptanyl, carboxybicyclo-[2.2.2]octanyl, fluorooxetanyl, hydroxyoxetanyl, hydroxyazetidinyl, (hydroxy)(methyl)-azetidinyl, carboxyazetidinyl, (tert-butoxycarbonyl)(hydroxy)azetidinyl, tetrazolyl-azetidinyl, hydroxytetrahydrofuranyl, pyrrolidinyl, hydroxypyrrolidinyl, carboxy-pyrrolidinyl, (carboxy)(methyl)pyrrolidinyl, carboxymethylpyrrolidinyl, ethoxycarbonyl-pyrrolidinyl, fluorotetrahydropyranyl, tetrahydropyranyl, hydroxytetrahydropyranyl, piperidinyl, difluoro-piperidinyl, (cyano)(methyl)piperidinyl, (hydroxy)(nitromethyl)piperidinyl, (hydroxy)-(methyl)piperidinyl, (hydroxy)(trifluoromethyl)piperidinyl, (hydroxymethyl)(methyl)-piperidinyl, methylsulphonylpiperidinyl, oxopiperidinyl, (formyl)(methyl)piperidinyl, acetylpiperidinyl, carboxypiperidinyl, (carboxy)(fluoro)piperidinyl, (carboxy)(methyl)-piperidinyl, (carboxy)(ethyl)piperidinyl, (carboxy)(trifluoromethyl)piperidinyl, (carboxy)-(hydroxy)piperidinyl, (carboxy)(hydroxymethyl)piperidinyl, (carboxy)(methoxy)-piperidinyl, (amino)(carboxy)piperidinyl, carboxymethylpiperidinyl, methoxycarbonyl-piperidinyl, (methoxycarbonyl)(methyl) piperidinyl, (ethyl)(methoxycarbonyl)piperidinyl, (isopropyl)(methoxycarbonyl)piperidinyl, (methoxy)(methoxycarbonyl)piperidinyl, (carboxy)(methoxycarbonyl)piperidinyl, ethoxycarbonylpiperidinyl, (ethoxycarbonyl)-(fluoro)piperidinyl, (ethoxycarbonyl)(methyl)piperidinyl, (ethoxycarbonyl)(trifluoro-methyl)piperidinyl, (ethoxycarbonyl)(hydroxymethyl)piperidinyl, (n-butoxycarbonyl)-(methyl)piperidinyl, (methyl)(morpholinylethoxycarbonyl)piperidinyl, ethoxycarbonyl-methylpiperidinyl, methylsulphonylaminocarbonylpiperidinyl, acetylaminosulphonyl-piperidinyl, methoxyaminocarbonylpiperidinyl, tetrazolylpiperidinyl, hydroxyoxadiazolyl-piperidinyl, aminosulphonylpiperidinyl, piperazinyl, methylpiperazinyl, cyanoethylpiperazinyl, trifluoroethyl-piperazinyl, methylsulphonylpiperazinyl, methylsulphonylethylpiperazinyl, oxopiperazinyl, acetylpiperazinyl, carboxypiperazinyl, tert-butoxycarbonylpiperazinyl, carboxymethylpiperazinyl, carboxyethylpiperazinyl, ethoxycarbonylmethylpiperazinyl, ethoxycarbonylethylpiperazinyl, (tert-butoxycarbonyl)piperazinyl, tetrazolylmethylpiperazinyl, trioxohexahydro-[1,2,5]thiadiazolo[2,3-a]pyrazinyl, morpholinyl, dimethylmorpholinyl, hydroxymethyl-morpholinyl, carboxymorpholinyl, (carboxy)(methyl)morpholinyl, carboxymethyl-morpholinyl, thiomorpholinyl, oxothiomorpholinyl, dioxothiomorpholinyl, carboxy-azepanyl, carboxyoxazepanyl, oxodiazepanyl, (methyl)(oxo)diazepanyl, dioxo-thiadiazepanyl, carboxy-3-azabicyclo[3.1.0]hexanyl, (carboxy)(methyl)-3-azabicyclo-[3.1.0]hexanyl, methoxycarbonyl-3-azabicyclo[3.1.0]hexanyl, ethoxycarbonyl-3-azabicyclo[3.1.0]hexanyl, 2-oxa-5-azabicyclo[2.2.1]heptanyl, carboxy-2-oxa-5-azabicyclo[2.2.1]heptanyl, carboxy-3-azabicyclo[3.1.1]heptanyl, carboxy-3-azabicyclo-[4.1.0]heptanyl, methoxycarbonyl-3-azabicyclo[4.1.0]heptanyl, ethoxycarbonyl-3-azabicyclo[4.1.0]heptanyl, (hydroxy)(methyl)(oxo)-2-oxabicyclo[2.2.2]octanyl, carboxy-3-azabicyclo[3.2.1]octanyl, methoxycarbonyl-3-azabicyclo[3.2.1]octanyl, oxo-8-azabicyclo[3.2.1]octanyl, ethoxycarbonylmethylidenyl-8-azabicyclo[3.2.1]octanyl, 3-oxa-8-azabicyclo[3.2.1]octanyl, oxo-3,6-diazabicyclo[3.2.2]nonanyl, carboxy-3-oxa-7-azabicyclo[3.3.1]nonanyl, 3,7-dioxa-9-azabicyclo[3.3.1]nonanyl, carboxy-5-azaspiro[2.3]hexanyl, (carboxy)(methyl)-5-azaspiro-[2.3]hexanyl, carboxy-5-azaspiro[2.4]heptanyl, carboxy-2-azaspiro[3.3]heptanyl, 2-oxa-6-azaspiro[3.3]heptanyl, 2-oxa-6-azaspiro[3.4]octanyl, 2-oxa-6-azaspiro[3.5]nonanyl, 2-oxa-7-azaspiro[3.5]nonanyl, (dioxo)(methyl)-2,4,8-triazaspiro[4.5]decanyl, 3,6-epiminofuro [3.2-b]furanly-pyrimidinyl, methylsulphoximinyl, (methyl)cyclobutyldiol, (imino)(oxo)thiazinanyl, (oxo)thiazinanyl. (dioxo)thiazinanyl or (methyl)triazolyl.

Suitably, $R^8$ represents hydroxy, methoxy, morpholinyl, hydroxyisopropyl and aminoisopropyl.

Illustratively, $R^8$ represents hydroxy, methoxy or morpholinyl. Illustratively, $R^8$ additionally represents hydroxyisopropyl.

In one embodiment $R^9$ represents hydrogen. In a second embodiment, $R^9$ represents halogen. In a third embodiment, $R^9$ represents cyano. In a fourth embodiment, $R^9$ represents trifluoromethyl. In a fifth embodiment, $R^9$ represents hydroxy. In a sixth embodiment, $R^9$ represents —$NR^bR^c$. In one aspect of this embodiment $R^9$ represents —$NH_2$. In a seventh embodiment, $R^9$ represents —$OR^a$. In one aspect of that embodiment, $R^9$ represents methoxy. In an eighth embodiment, $R^9$ represents $C_{1-6}$ alkyl. In one aspect of that embodiment, $R^9$ represents methyl. In a ninth embodiment, $R^9$ represents $C_{1-6}$ alkylsulphonyl. In one aspect of that embodiment, $R^9$ represents methylsulphonyl.

In one embodiment $R^{10}$ represents hydrogen. In a second embodiment, $R^{10}$ represents halogen. In a third embodiment, $R^{10}$ represents cyano. In a fourth embodiment, $R^{10}$ represents trifluoromethyl. In a fifth embodiment, $R^{10}$ represents hydroxy. In a sixth embodiment, $R^{10}$ represents —$NR^bR^c$. In one aspect of this embodiment $R^{10}$ represents —$NH_2$. In a seventh embodiment, $R^{10}$ represents —$OR^a$. In one aspect of that embodiment, $R^{10}$ represents methoxy. In an eighth embodiment, $R^{10}$ represents $C_{1-6}$ alkyl. In one aspect of that embodiment, $R^{10}$ represents methyl. In a ninth embodiment, $R^{10}$ represents $C_{1-6}$ alkylsulphonyl. In one aspect of that embodiment, $R^{10}$ represents methylsulphonyl.

In a particular embodiment, $R^9$ and $R^{10}$ represent independently hydrogen.

Generally, $R^{11}$ represents hydrogen or $C_{1-6}$ alkyl.

Particular values of $R^{11}$ include hydrogen and methyl.

In a particular embodiment $R^{11}$ is hydrogen.

Another sub-class of compounds of formula (I) according to the invention is represented by the compounds of formula (IIB) and N-oxides thereof, and pharmaceutically acceptable salts and solvates thereof, and glucuronide derivatives thereof, and co-crystals thereof:

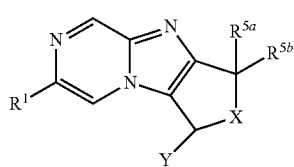

(IIB)

wherein $R^1$, $R^{5a}$, $R^{5b}$, X and Y are as defined above.

A particular sub-group of the compounds of formula (IIB) is represented by the compounds of formula (IIB-A) and N-oxides thereof, and pharmaceutically acceptable salts and solvates thereof, and glucuronide derivatives thereof, and co-crystals thereof:

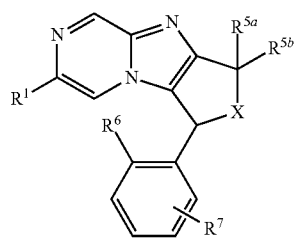

(IIB-A)

Wherein X, $R^1$, $R^{5a}$, $R^{5b}$, $R^6$ and $R^7$ are as defined above.

A particular sub-group of the compounds of formula (IIB-A) above is represented by compounds of formula (IIB-AB), and N-oxides thereof, and pharmaceutically acceptable salts and solvates thereof, and glucuronide derivatives thereof, and co-crystals thereof:

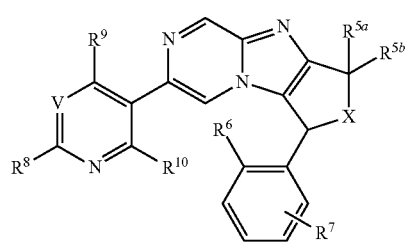

(IIB-AB)

Wherein X, $R^{5a}$, $R^{5b}$, $R^6$, $R^7$, $R^8$, $R^9$ and $R^{10}$ are as defined above.

Specific novel compounds in accordance with the present invention include each of the compounds whose preparation is described in the accompanying Examples, and pharmaceutically acceptable salts and solvates thereof, and co-crystals thereof.

Therefore, in a particular aspect, the present invention relates to compounds of formula (I) which are selected from the group consisting of 1-[2-(difluoromethoxy)phenyl]-8-(6-methoxypyridin-3-yl)-3,4-dihydro-1H-pyrano[4',3':4,5]imidazo[1,2-a]pyrazine;

1-[2-(difluoromethoxy)phenyl]-8-[2-(morpholin-4-yl)pyrimidin-5-yl]-3,4-dihydro-1H-pyrano[4',3':4,5]imidazo[1,2-a]pyrazine;

5-{1-[2-(difluoromethoxy)phenyl]-3,4-dihydro-1H-pyrano[4',3':4,5]imidazo[1,2-a]pyrazin-8-yl}pyridin-2(1H)-one;

(1S)-8-bromo-1-[2-(difluoromethoxy)phenyl]-3,4-dihydro-1H-pyrano[4',3':4,5]imidazo[1,2-a]pyrazine;

(1R)-8-bromo-1-[2-(difluoromethoxy)phenyl]-3,4-dihydro-1H-pyrano[4',3':4,5]imidazo[1,2-a]pyrazine;

(1S)-8-bromo-1-[2-(difluoromethoxy)phenyl]-3,4-dihydro-1H-pyrano[4',3':4,5]imidazo[1,2-a]pyrazine;

(1R)-8-bromo-1-[2-(difluoromethoxy)phenyl]-3,4-dihydro-1H-pyrano[4',3':4,5]imidazo[1,2-a]pyrazine;

(6R,8R)-8-[5-chloro-2-(difluoromethoxy)phenyl]-2-[6-(1-hydroxy-1-methyl-ethyl)-3-pyridyl]-7,8-dihydro-6H-cyclopenta[1,2]imidazo[3,4-b]pyrazin-6-ol;

(6S,8S)-8-[5-chloro-2-(difluoromethoxy)phenyl]-2-[6-(1-hydroxy-1-methyl-ethyl)-3-pyridyl]-7,8-dihydro-6H-cyclopenta[1,2]imidazo[3,4-b]pyrazin-6-ol;

2-[[(6R,8R)-8-[5-chloro-2-(difluoromethoxy)phenyl]-2-[6-(1-hydroxy-1-methyl-ethyl)-3-pyridyl]-7,8-dihydro-6H-cyclopenta[1,2]imidazo[3,4-b]pyrazin-6-yl]oxy]acetamide; and 2-[[(6S,8S)-8-[5-chloro-2-(difluoromethoxy)phenyl]-2-[6-(1-hydroxy-1-methyl-ethyl)-3-pyridyl]-7,8-dihydro-6H-cyclopenta[1,2]imidazo[3,4-b]pyrazin-6-yl]oxy]acetamide.

The compounds in accordance with the present invention are beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, polymyositis, scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anaemia of chronic disease (ACD), Still's disease (juvenile and/or adult onset), Behçet's disease and Sjögren's syndrome. Autoimmune endocrine disorders include thyroiditis. Organ-specific autoimmune disorders include Addison's disease, haemolytic or pernicious anaemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy) and organ transplant rejection (including kidney allograft rejection).

Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNFα function may also be of use in the treatment and/or prevention of myocardial infarction (see J. J. Wu et al., *JAMA,* 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy, macular oedema and retinopathy of prematurity), macular oedema (including diabetic macular oedema), age-related macular degeneration (ARMD), vascularisation (including corneal vascularisation and neovascularisation), retinal vein occlusion, and various forms of uveitis and keratitis.

Oncological disorders, which may be acute or chronic, include proliferative disorders, especially cancer, and cancer-associated complications (including skeletal complications, cachexia and anaemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle. Modulators of TNFα function may also be used to increase the safety of the potent anticancer effect of TNF (see F. V. Hauwermeiren et al., *J. Clin. Invest.,* 2013, 123, 2590-2603).

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule such as methotrexate or prednisolone.

It will be apparent to the person skilled in the art that there are various synthetic pathways that can lead to the compounds according to the invention. The following processes are aimed at illustrating some of these synthetic pathways but should not be construed in any way as a limitation on how the compounds according to the invention should be made.

Compounds of formula (I) above, wherein n represents an integer equal to 1, X represents —NH or oxygen, E represents respectively —$NH_2$ or —OH, $R^4$ is hydrogen and $R^1$, $R^2$, $R^3$, $R^{5a}$ and $R^{5b}$ are as defined above, may be prepared by a process which involves reacting an intermediate of formula (III), with a compound of formula Y—(CO)—H, wherein Y is as defined above, or its corresponding dialkyl acetal, e.g. dimethyl acetal.

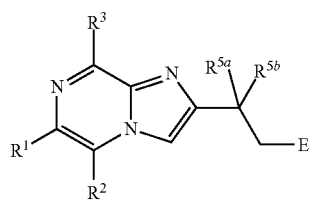

(III)

When $R^{5a}$ and $R^{5b}$ are hydrogen and E is —$NH_2$, the transformation is conveniently effected in the presence of an acid, e.g. para-toluenesulfonic acid, or in the presence of a salt, e.g. magnesium chloride, in a suitable solvent e.g. toluene or acetonitrile, at elevated temperature.

Alternatively, when the dimethyl acetal of Y—(CO)—H is used, the reaction may be conveniently effected in the presence of pyridinium-para-toluenesulphonate in a suitable solvent, e.g. acetonitrile, using Microwave according to the Oxa-Pictet-Spengler reaction.

The dimethylacetal of Y—(CO)—H may, for example, be conveniently prepared by reacting Y—(CO)—H with trimethylorthoformate in the presence of ammonium chloride in a suitable solvent, e.g. methanol.

Intermediates represented by formula (III) wherein E is —OH, may be prepared by a process which involves reduction of an intermediate represented by formula (IV), wherein $R^k$ represents a $C_{1-6}$ alkyl and $R^1$, $R^2$, $R^3$, $R^{5a}$ and $R^{5b}$ are as defined above.

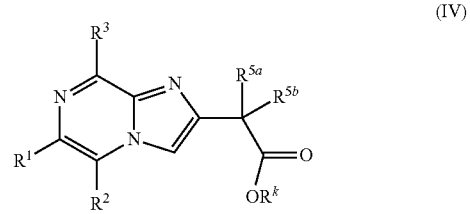

(IV)

The reaction is conveniently effected by treatment with a suitable reducing agent, e.g. diisobutylaluminium hydride, in a suitable solvent, e.g. THF.

Intermediates of formula (III) wherein E is —$NH_2$ are obtained by a process involving a two step reaction from intermediates of formula (III) wherein E is —OH.

The first step is performed by treating intermediate of formula (III) wherein E is —OH with phthalimide, triphenylphosphine, and diisopropylazadicarboxylate in a suitable solvent, e.g. THF. The compound thereby obtained, is further treated with hydrazine in a suitable solvent, e.g. methanol, at elevated temperature, to afford the desired intermediate of formula (III) wherein E is —$NH_2$.

Intermediates of formula (IV) as defined above may be prepared by a process involving reacting intermediates of formula (V), wherein $R^1$, $R^2$ and $R^3$ are as defined above with intermediates of formula (VI), wherein $R^{5a}$, $R^{5b}$ and $R^k$ are as defined above and $L^1$ represents a suitable leaving group, e.g. a halogen atom.

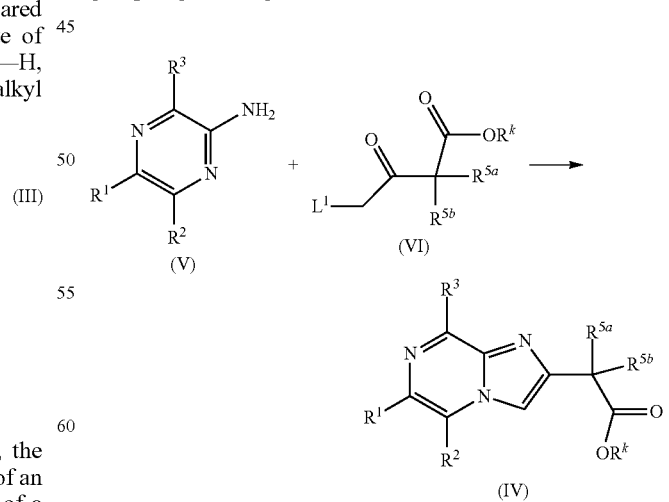

The reaction is conveniently effected at an elevated temperature in a suitable solvent, e.g. a $C_{1-4}$ alkanol such as ethanol, or an ether such as 1,4-dioxane or dimethoxyethane.

Intermediates of formula (IV) wherein $R^1$ is hydrogen may be transformed into the corresponding intermediate wherein $R^1$ is a bromine or a chlorine, by treatment with N-Chloro or N-Bromo succinimide in a suitable solvent, e.g. acetonitrile.

Compounds of formula (I) above, wherein n represents an integer equal to 1, X represents methylene and $R^4$ represents hydroxy may be prepared by a process which includes reacting an intermediate of formula (VII) with a compound of formula Y—Mg—$X^1$, wherein $X^1$ is a halogen, for example chloro, applying Grignard conditions known to the person skilled in the art.

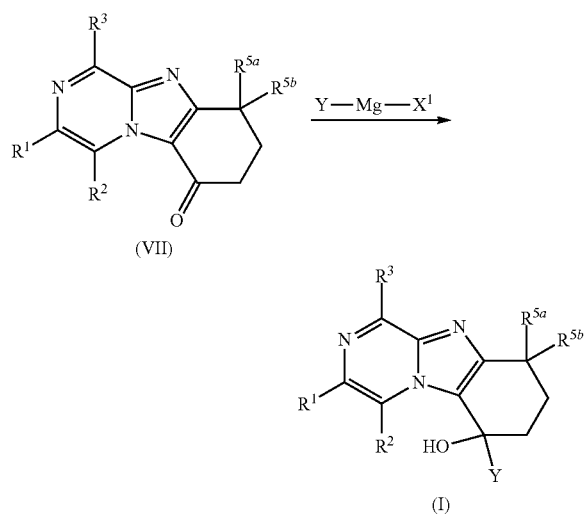

Compounds of formula (I) wherein $R^4$ represents hydroxy may subsequently be transformed into compound of formula (I) wherein $R^4$ represents hydrogen by deoxygenation according to a method analogous to the one described by Barton, D. H. R. et al. in *J. Chem. Soc., Perkin Trans.* 1(1975), 16: 1574-1585, or any other method known to the person skilled in the art.

Compounds of formula (VII) may be prepared by a process which includes reacting intermediate compound of formula (V) with an intermediate compound of formula (VIII), wherein $L^2$ is a leaving group, for example halogen, preferably bromine.

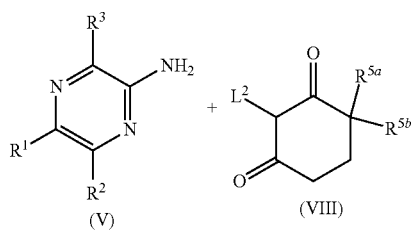

The reaction is conveniently effected in a polar solvent, such as ethanol, at elevated temperature.

Compounds of formula (I) above, wherein n represents an integer equal to 0, X represents methylene, $R^4$ represents hydrogen, $R^{5a}$ represents hydroxy and $R^{5b}$ represents hydrogen may be prepared from intermediates of formula (IX),

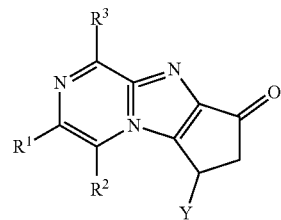

wherein $R^1$, $R^2$, $R^3$ and Y are as defined above; by reduction of the carbonyl moiety according to methods known to the person skilled in the art.

Intermediates of formula (IX) may be prepared by a process which includes intramolecular cyclization of an intermediate of formula (X),

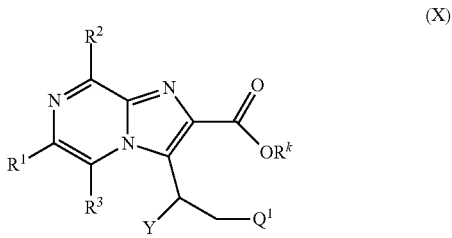

wherein $Q^1$ is an electron withdrawing group, preferably an ester moiety, $R^k$, $R^1$, $R^2$, $R^3$ and Y are as defined above.

The reaction is conveniently effected in the presence of a base, in a suitable solvent at elevated temperature.

Intermediates of formula (X) may be prepared by a multi-step process involving reaction of an intermediate of formula (XI),

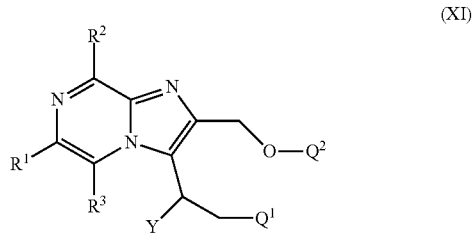

wherein $Q^1$ represents —COOH, $Q^2$ represents a protecting group and $R^1$, $R^2$, $R^3$ and Y are as defined above.

In a first step, intermediate of formula (XI) is deprotected and the resulting alcohol moiety is further oxidized into the corresponding carboxylic acid moiety.

Resulting intermediate of formula (XI) wherein $Q^1$ is as defined above and —$CH_2$—$OQ^2$ represents —COOH is esterified into corresponding intermediate of formula (X) according to methods known to the person skilled in the art.

Intermediates of formula (XI), as described above, may be prepared according to a process which comprises reacting an intermediate of formula (XII),

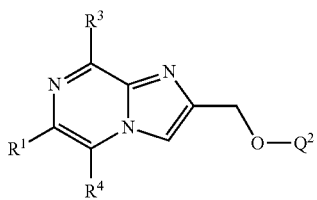

(XII)

wherein $R^1$, $R^3$, $R^4$, and $Q^2$ are as defined above; with an intermediate of formula Y—CO—H, in the presence of Meldrum's acid, according to a method analogous to the one described in international patent application WO 2009/156091 or by M. Kerr et al. in *J. Org. Chem* 2013, 78, 10534.

The reaction is conveniently effected in a suitable solvent e.g. acetonitrile, in the presence of a Lewis acid, e.g. scandium triflate, or in the presence of an organocatalyst, e.g. proline, and magnesium sulphate, at elevated temperature, e.g. 80° C.

Intermediate of formula (XII) may be prepared by a process comprising reduction of intermediate of formula (XIII),

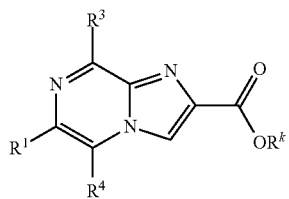

(XIII)

wherein $R^1$, $R^3$, $R^4$ and $R^k$ are as defined above, followed by suitable protection of the resulting alcohol, according to methods known to the person skilled in the art.

Intermediate of formula (XIII) may be prepared by a process comprising reacting an intermediate of formula (V) with an intermediate of formula (XIV),

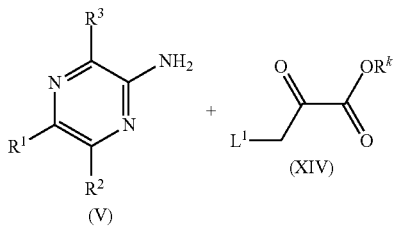

(XIV)

(V)

wherein $L^1$, $R^1$, $R^2$, $R^3$ and $R^k$ are as defined above.

The reaction is conveniently effected according to a method analogous to the one described for the reaction of intermediate of formula (V) with intermediate of formula (VI).

References to compound of formula (I) below will be understood as including all potential subclasses and subgroups mentioned above.

A compound of formula (I) which contains a carbonyl group, in particular a compound of formula (I) wherein $R^{5a}$ and $R^{5b}$ with the carbon atom to which they are attached form a carbonyl, may be transformed into the corresponding compound wherein $R^{5a}$ is a hydroxy group and $R^{5b}$ is a hydrogen using for example lithium-tri-sec-butyl-borohydride or sodium borohydride in a suitable solvent e.g. THF.

A compound of formula (I) which contains a carbonyl group, in particular a compound of formula (I) wherein $R^{5a}$ and $R^{5b}$ with the carbon atom to which they are attached form a carbonyl, may be transformed into the corresponding compound wherein $R^{5a}$ is a trifluoromethyl and $R^{5b}$ is a hydroxy by treatment with trifluoromethylsilane at room temperature in a suitable solvent e.g. dimethoxyethane.

A compound of formula (I) which contains a carbonyl group, in particular a compound of formula (I) wherein $R^{5a}$ and $R^{5b}$ with the carbon atom to which they are attached form a carbonyl, may be transformed into the corresponding compound wherein $R^{5a}$ is a ($C_{1-6}$ alkyl)sulphonylaryloxy trifluoromethyl and $R^{5b}$ is a hydrogen by treatment with ($C_{1-6}$ alkyl)sulphonylphenol, in the presence of diisopropyl-1,2-diazenedicarboxylate, in a suitable solvent, e.g THF.

A compound of formula (I) which contains a carbonyl group, in particular a compound of formula (I) wherein $R^{5a}$ and $R^{5b}$ with the carbon atom to which they are attached form a carbonyl may transformed into the corresponding compound wherein $R^{5a}$ and $R^{5b}$ together with the carbon to which they are attached form a —C=N—OH, by treatment, for example with hydroxylamine chloride in the presence of pyridine in the presence of a suitable solvent such as ethanol.

A compound of formula (I) which contains a hydroxy group, in particular a compound of formula (I) wherein $R^{5a}$ is a hydroxy group and $R^{5b}$ is a hydrogen, may be transformed into corresponding compound wherein $R^{5a}$ and $R^{5b}$ are hydrogen for example by treatment with iodotrimethylsilane in a suitable solvent, e.g. acetonitrile.

A compound of formula (I) which contains a hydroxy group, in particular a compound of formula (I) wherein $R^{5a}$ is a hydroxy group and $R^{5b}$ is a hydrogen, may be transformed in a two step reaction into corresponding compound wherein $R^{5a}$ is —$NH_2$ and $R^{5b}$ is hydrogen for example by (i) treatment with diphenylphosphorylazide and 1,8-diazabicyclo[5.4.0]undec-7-ene. This reaction is conveniently performed at 0° C. in THF; (ii) subsequent aza-Wittig reaction using $PPh_3$ in a suitable solvent, e.g. a mixture of water and toluene.

A compound of formula (I) which contains a hydroxy group, in particular a compound of formula (I) wherein $R^{5a}$ is a hydroxy group and $R^{5b}$ is a hydrogen, may be transformed into corresponding compound wherein $R^{5a}$ is —F and $R^{5b}$ is hydrogen by treatment with diethylaminosulfur trifluoride in a suitable solvent, e.g. THF.

A compound of formula (I) which contains a hydroxy group, in particular a compound of formula (I) wherein $R^{5a}$ is a hydroxy group and $R^{5b}$ is a hydrogen, may be transformed into the corresponding compound of formula (I) wherein $R^{5a}$ is a $C_{1-4}$ alkyl, e.g. methyl, and $R^{5b}$ is a hydrogen by treatment, for example, with an alkylmagnesium bromide in a suitable solvent, for example diethylether.

A compound of formula (I) which contains a hydroxy group, in particular a compound of formula (I) wherein $R^{5a}$ is a hydroxy group and $R^{5b}$ is a hydrogen may be transformed into the corresponding compound wherein $R^{5a}$ is a $C_{1-4}$ alkoxy, e.g. methoxy, and $R^{5b}$ is a hydrogen by treatment with a base e.g. sodium hydride, in a suitable solvent, e.g. THF, in the presence of a suitable alkylation agent, such as an alkylhalide, e.g. methyliodide.

A compound of formula (I) which contains a hydroxy group may be alkylated by treatment with the appropriate alkyl halide in the presence of a base, e.g. sodium hydride, or silver oxide.

A compound of formula (I) which contains hydroxy may be converted into the corresponding fluoro-substituted compound by treatment with diethylaminosulfur trifluoride (DAST) or bis(2-methoxyethyl)aminosulfur trifluoride (BAST).

A compound of formula (I) which contains hydroxy may be converted into the corresponding difluoro-substituted compound via a two-step procedure which comprises: (i) treatment with an oxidising agent, e.g. manganese dioxide; and (ii) treatment of the carbonyl-containing compound thereby obtained with DAST.

A compound of formula (I) which contains an hydroxy group, in particular a compound of formula (I) wherein $R^{5a}$ is a hydroxy group and $R^{5b}$ is a hydrogen, may be converted into the corresponding compound of formula (I) containing an (aminocarbonyl)methoxy group via a two-step procedure which comprises (i) treatment with bromoacetonitrile in a suitable solvent e.g. THF at low temperature, in the presence of sodium hydride and (ii) treatment of the nitrile-containing compound thereby obtained with a solution of hydrobromide acid in acetic acid.

A compound of formula (I) which contains an N—H moiety may be alkylated by treatment with the appropriate alkyl halide, typically at an elevated temperature in an organic solvent such as acetonitrile; or at ambient temperature in the presence of a base, e.g. an alkali metal carbonate such as potassium carbonate or cesium carbonate, in a suitable solvent, e.g. a dipolar aprotic solvent such as N,N-dimethylformamide. Alternatively, a compound of formula (I) which contains an N—H moiety may be alkylated by treatment with the appropriate alkyl tosylate in the presence of a base, e.g. an inorganic base such as sodium hydride, or an organic base such as 1,8-diazabicyclo[5.4.0]undec-7-ene (DBU).

A compound of formula (I) which contains an N—H moiety may be methylated by treatment with formaldehyde in the presence of a reducing agent, e.g. sodium triacetoxyborohydride.

A compound of formula (I) which contains an N—H moiety may be acylated by treatment with the appropriate acid chloride, e.g. acetyl chloride, or with the appropriate carboxylic acid anhydride, e.g. acetic anhydride, typically at ambient temperature in the presence of a base, e.g. an organic base such as triethylamine.

A compound of formula (I) which contains an N—H moiety may be converted into the corresponding compound wherein the nitrogen atom is substituted by $C_{1-6}$ alkylsulphonyl, e.g. methylsulphonyl, by treatment with the appropriate $C_{1-6}$ alkylsulphonyl chloride, e.g. methanesulphonyl chloride, or with the appropriate $C_{1-6}$ alkylsulphonic acid anhydride, e.g. methanesulphonic anhydride, typically at ambient temperature in the presence of a base, e.g. an organic base such as triethylamine or N,N-diisopropylethylamine.

A compound of formula (I) substituted by amino (—$NH_2$) may be converted into the corresponding compound substituted by $C_{1-6}$ alkylsulphonylamino, e.g. methylsulphonylamino, or bis[($C_{1-6}$)alkylsulphonyl]amino, e.g. bis(methylsulphonyl)amino, by treatment with the appropriate $C_{1-6}$ alkylsulphonyl halide, e.g. a $C_{1-6}$ alkylsulphonyl chloride such as methanesulphonyl chloride. Similarly, a compound of formula (I) substituted by hydroxy (—OH) may be converted into the corresponding compound substituted by $C_{1-6}$ alkyl-sulphonyloxy, e.g. methylsulphonyloxy, by treatment with the appropriate $C_{1-6}$ alkyl-sulphonyl halide, e.g. a $C_{1-6}$ alkylsulphonyl chloride such as methanesulphonyl chloride.

A compound of formula (I) containing the moiety —S— may be converted into the corresponding compound containing the moiety —S(O)— by treatment with 3-chloroperoxy-benzoic acid. Likewise, a compound of formula (I) containing the moiety —S(O)— may be converted into the corresponding compound containing the moiety —$S(O)_2$— by treatment with 3-chloroperoxybenzoic acid. Alternatively, a compound of formula (I) containing the moiety —S— may be converted into the corresponding compound containing the moiety —$S(O)_2$— by treatment with Oxone® (potassium peroxymonosulfate).

A compound of formula (I) containing an aromatic nitrogen atom may be converted into the corresponding N-oxide derivative by treatment with 3-chloroperoxy-benzoic acid.

A compound of formula (I) which contains a carbonyl may be converted into the corresponding alcohol by treatment with a suitable borohydride, e.g. lithium-tri-sec-butylborohydride or sodium borohydride, in a suitable solvent e.g. THF.

A bromophenyl derivative of formula (I) may be converted into the corresponding optionally substituted 2-oxopyrrolidin-1-ylphenyl or 2-oxooxazolidin-3-ylphenyl derivative by treatment with pyrrolidin-2-one or oxazolidin-2-one, or an appropriately substituted analogue thereof. The reaction is conveniently effected at an elevated temperature in the presence of copper(I) iodide, trans-N,N'-dimethylcyclohexane-1,2-diamine and an inorganic base such as potassium carbonate.

A compound of formula (I) wherein $R^1$ represents halogen, e.g. bromo, may be converted into the corresponding compound wherein $R^1$ represents an optionally substituted aryl or heteroaryl moiety by treatment with the appropriately substituted aryl or heteroaryl boronic acid or a cyclic ester thereof formed with an organic diol, e.g. pinacol, 1,3-propanediol or neopentyl glycol. The reaction is typically effected in the presence of a transition metal catalyst, e.g. [1,1'-bis(diphenylphosphino)ferrocene]dichloropalladium (II), tetrakis(triphenylphosphine)palladium(0), bis[3-(diphenylphosphanyl)cyclopenta-2,4-dien-1-yl]iron-dichloropalladium-dichloromethane complex, and a base, e.g. an inorganic base such as sodium carbonate or potassium carbonate, or potassium phosphate. This reaction may conveniently be performed in a 1,4-dioxane with or without the use of micro wave technology. Alternatively, the above reaction can be effected in the presence of tris(dibenzylideneacetone)dipalladium(0)-chloroform and dicyclohexyl-[2-(2,4,6-triisopropylphenyl)phenyl]phosphane, in a polar solvent, e.g., n-butanol, at high temperature.

A compound of formula (I) wherein $R^1$ represents halogen, e.g. bromo, may be converted into the corresponding compound wherein $R^1$ represents an optionally substituted aryl, heteroaryl or heterocycloalkenyl moiety via a two-step procedure which comprises: (i) reaction with bis(pinacolato)diboron or bis(neopentyl glycolato)diboron; and (ii) reaction of the compound thereby obtained with an appropriately functionalised halo- or tosyloxy-substituted aryl, heteroaryl or heterocycloalkenyl derivative. Step (i) is conveniently effected in the presence of a transition metal catalyst such as [1,1'-bis-(diphenylphosphino)ferrocene]dichloropalladium (II), or bis[3-(diphenylphosphanyl)-cyclopenta-2,4-dien-1-yl]iron-dichloropalladium-dichloromethane complex. Step (ii) is conveniently effected in the presence of a transition metal catalyst such as tetrakis-(triphenylphosphine)palladium(0), or bis[3-(diphenylphosphanyl)cyclopenta-2,4-dien-1-yl]iron-dichloropalladium-dichloromethane complex, and a base, e.g. an inorganic base such as sodium carbonate or potassium carbonate.

A compound of formula (I) wherein $R^1$ represents halogen, e.g. bromo, may be converted into the corresponding compound wherein $R^1$ represents an optionally substituted $C_{2-6}$ alkynyl moiety by treatment with an appropriately substituted alkyne derivative, e.g. 2-hydroxybut-3-yne. The reaction is conveniently accomplished with the assistance of a transition metal catalyst, e.g. tetrakis(triphenylphosphine)palladium(0), typically in the presence of copper(I) iodide and a base, e.g. an organic base such as triethylamine.

A compound of formula (I) wherein $R^1$ represents halogen, e.g. bromo, may be converted into the corresponding compound wherein $R^1$ represents an optionally substituted imidazol-1-yl moiety by treatment with the appropriately substituted imidazole derivative, typically in the presence of copper(II) acetate and an organic base such as N,N,N',N'-tetramethylethylenediamine (TMEDA).

A compound of formula (I) wherein $R^1$ represents halogen, e.g. bromo, may be converted into the corresponding compound wherein $R^1$ represents 2-(methoxycarbonyl)-ethyl via a two-step procedure which comprises: (i) reaction with methyl acrylate; and (ii) catalytic hydrogenation of the alkenyl derivative thereby obtained, typically by treatment with a hydrogenation catalyst, e.g. palladium on charcoal, under an atmosphere of hydrogen gas. Step (i) is typically effected in the presence of a transition metal catalyst, e.g. palladium(II) acetate or bis(dibenzylideneacetone)palladium(0), and a reagent such as tri(ortho-tolyl)phosphine.

In general, a compound of formula (I) containing a —C═C— functionality may be converted into the corresponding compound containing a —CH—CH— functionality by catalytic hydrogenation, typically by treatment with a hydrogenation catalyst, e.g. palladium on charcoal, under an atmosphere of hydrogen gas, optionally in the presence of a base, e.g. an alkali metal hydroxide such as sodium hydroxide.

A compound of formula (I) wherein $R^1$ represents 6-methoxypyridin-3-yl may be converted into the corresponding compound wherein $R^1$ represents 2-oxo-(1H)-pyridinyl by treatment with pyridine hydrochloride; or by heating with a mineral acid such as hydrochloric acid. By utilising similar methodology, a compound of formula (I) wherein $R^1$ represents 6-methoxy-4-methylpyridin-3-yl may be converted into the corresponding compound wherein $R^1$ represents 4-methyl-2-oxo-1,2-dihydropyridin-5-yl; and a compound of formula (I) wherein $R^1$ represents 6-methoxy-5-methylpyridin-3-yl may be converted into the corresponding compound wherein $R^1$ represents 3-methyl-2-oxo-1,2-dihydropyridin-5-yl.

A compound of formula (I) wherein $R^1$ represents 2-oxo-1,2-dihydropyridin-5-yl may be converted into the corresponding compound wherein $R^1$ represents 2-oxopiperidin-5-yl by catalytic hydrogenation, typically by treatment with gaseous hydrogen in the presence of a hydrogenation catalyst such as platinum(IV) oxide.

A compound of formula (I) containing an ester moiety, e.g. a $C_{2-6}$ alkoxycarbonyl group such as methoxycarbonyl or ethoxycarbonyl, may be converted into the corresponding compound containing a carboxy (—$CO_2$H) moiety by treatment with an acid, e.g. a mineral acid such as hydrochloric acid.

A compound of formula (I) containing an N-(tert-butoxycarbonyl) moiety may be converted into the corresponding compound containing an N—H moiety by treatment with an acid, e.g. a mineral acid such as hydrochloric acid, or an organic acid such as trifluoroacetic acid.

A compound of formula (I) containing an ester moiety, e.g. a $C_{2-6}$ alkoxycarbonyl group such as methoxycarbonyl or ethoxycarbonyl, may alternatively be converted into the corresponding compound containing a carboxy (—$CO_2$H) moiety by treatment with a base, e.g. an alkali metal hydroxide selected from lithium hydroxide, sodium hydroxide and potassium hydroxide; or an organic base such as sodium methoxide or sodium ethoxide.

A compound of formula (I) containing a carboxy (—$CO_2$H) moiety may be converted into the corresponding compound containing an amide moiety by treatment with the appropriate amine in the presence of a condensing agent such as 1-ethyl-3-(3-dimethyl-aminopropyl)carbodiimide.

A compound of formula (I) containing a carbonyl (C═O) moiety may be converted into the corresponding compound containing a —C(CH$_3$)(OH)— moiety by treatment with methylmagnesium bromide. Similarly, a compound of formula (I) containing a carbonyl (C═O) moiety may be converted into the corresponding compound containing a —C(CF$_3$)(OH)— moiety by treatment with (trifluoromethyl)trimethylsilane and cesium fluoride. A compound of formula (I) containing a carbonyl (C═O) moiety may be converted into the corresponding compound containing a —C(CH$_2$NO$_2$)(OH)— moiety by treatment with nitromethane.

A compound of formula (I) containing a hydroxymethyl moiety may be converted into the corresponding compound containing a formyl (—CHO) moiety by treatment with an oxidising agent such as Dess-Martin periodinane. A compound of formula (I) containing a hydroxymethyl moiety may be converted into the corresponding compound containing a carboxy moiety by treatment with an oxidising agent such as tetrapropylammonium perruthenate.

A compound of formula (I) wherein $R^1$ represents a substituent containing at least one nitrogen atom, which substituent is linked to the remainder of the molecule via a nitrogen atom, may be prepared by reacting a compound of formula (I) wherein $R^1$ represents halogen, e.g. bromo, with the appropriate compound of formula $R^1$—H [e.g. 1-(pyridin-3-yl)piperazine or morpholine]. The reaction is conveniently effected with the assistance of a transition metal catalyst, e.g. tris(dibenzylideneacetone)dipalladium(0), in the presence of an amination ligand such as 2-dicyclohexylphosphino-2',4',6'-triisopropyl-biphenyl (XPhos) or 2,2'-bis(diphenylphosphino)-1,1'-binaphthalene (BINAP) or Xantphos and a base, e.g. an inorganic base such as sodium tert-butoxide or cesium fluoride. Alternatively, the reaction may be effected using palladium diacetate, in the presence of a reagent such as [2',6'-bis(propan-2-yloxy)biphenyl-2-yl](dicyclohexyl)phosphane and a base, e.g. an inorganic base such as cesium carbonate.

A compound of formula (I) containing an oxo moiety can be converted into the corresponding compound containing an ethoxycarbonylmethylidene moiety by treatment with triethyl phosphonoacetate in the presence of a base such as sodium hydride.

A compound of formula (I) containing a C—OH moiety may be converted into the corresponding compound containing a C—F moiety by treatment with difluoro(morpholino)sulfonium tetrafluoroborate, in a suitable solvent, e.g. dichloromethane, at low temperature.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, $3^{rd}$ edition, 1999. The protecting groups may be removed at any convenient subsequent stage utilising methods known from the art.

Compounds in accordance with the present invention potently neutralise the activity of TNFα in a commercially available HEK-293 derived reporter cell line known as HEK-Blue™ CD40L. This is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a concentration-dependent manner by TNFα. When tested in the HEK-293 bioassay, also referred to herein as the reporter gene assay, compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 25 nM or less (the skilled person will appreciate that a lower $IC_{50}$ figure denotes a more active compound).

Certain compounds in accordance with the present invention potently inhibit the binding of a fluorescence conjugate to TNFα when tested in the fluorescence polarisation assay described herein. Indeed, when tested in that assay, compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 25 nM or less (as before, the skilled person will appreciate that a lower $IC_{50}$ figure denotes a more active compound).

The following Examples illustrate the preparation of compounds according to the invention.

The compounds of the Examples have been tested in one or both of the assays described below.

Fluorescence Polarisation Assay

Preparation of Compound (A)

1-(2,5-Dimethylbenzyl)-6-[4-(piperazin-1-ylmethyl)phenyl]-2-(pyridin-4-yl-methyl)-1H-benzimidazole—hereinafter referred to as "Compound (A)"—can be prepared by the procedure described in Example 499 of WO 2013/186229 (published 19 Dec. 2013); or by a procedure analogous thereto.

Preparation of Fluorescence Conjugate

Compound (A) (27.02 mg, 0.0538 mmol) was dissolved in DMSO (2 mL). 5 (–6) Carboxy-fluorescein succinimyl ester (24.16 mg, 0.0510 mmol) (Invitrogen catalogue number: C1311) was dissolved in DMSO (1 mL) to give a bright yellow solution. The two solutions were mixed at room temperature, the mixture turning red in colour. The mixture was stirred at room temperature. Shortly after mixing a 20 μL aliquot was removed and diluted in a 80:20 mixture of AcOH:H$_2$O for LC-MS analysis on the 1200RR-6140 LC-MS system. The chromatogram showed two closely eluting peaks at retention times of 1.42 and 1.50 minutes, both with mass $(M+H)^+$=860.8 amu, corresponding to the two products formed with the 5- and 6-substituted carboxyfluorescein group. A further peak at retention time 2.21 minutes had a mass of $(M+H)^+$=502.8 amu, corresponding to Compound (A). No peak was observed for unreacted 5(–6) carboxyfluorescein succinimyl ester. The peak areas were 22.0%, 39.6% and 31.4% for the three signals, indicating a 61.6% conversion to the two isomers of the desired fluorescence conjugate at that time-point. Further 20 μL aliquots were extracted after several hours and then after overnight stirring, diluted as before and subjected to LC-MS analysis. The percentage conversion was determined as 79.8% and 88.6% respectively at these time-points. The mixture was purified on a UV-directed preparative HPLC system. The pooled purified fractions were freeze-dried to remove excess solvent. After freeze-drying, an orange solid (23.3 mg) was recovered, equivalent to 0.027 mmol of fluorescence conjugate, corresponding to an overall yield of 53% for the reaction and preparative HPLC purification.

Inhibition of Binding of Fluorescence Conjugate to TNFα

Compounds were tested at 10 concentrations starting from 25 μM in a final assay concentration of 5% DMSO, by pre-incubation with TNFα for 60 minutes at ambient temperature in 20 mM Tris, 150 mM NaCl, 0.05% Tween 20, before addition of the fluorescence conjugate and a further incubation for 20 hours at ambient temperature. The final concentrations of TNFα and the fluorescence conjugate were 10 nM and 10 nM respectively in a total assay volume of 25 μL. Plates were read on a plate reader capable of detecting fluorescence polarisation (e.g. an Analyst HT plate reader; or an Envision plate reader). An $IC_{50}$ value was calculated using XLfit™ (4 parameter logistic model) in ActivityBase.

When tested in the fluorescence polarisation assay, the compounds of the accompanying Examples were all found to exhibit $IC_{50}$ values of 50 μM or better.

Reporter Gene Assay

Inhibition of TNFα-Induced NF-κB Activation

Stimulation of HEK-293 cells by TNF leads to activation of the NF-κB pathway. The reporter cell line used to determine TNF activity was purchased from InvivoGen. HEK-Blue™ CD40L is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a dose-dependent manner by TNF, with an EC50 of 0.5 ng/mL for human TNF. Compounds were diluted from 10 mM DMSO stocks (final assay concentration 0.3% DMSO) to generate a 10-point 3-fold serial dilution curve (e.g., 30,000 nM to 2 nM final concentration). Diluted compound was preincubated with TNF for 60 minutes prior to addition to a 384-well microtitre plate and incubated for 18 h. The final TNF concentration in the assay plate was 0.5 ng/mL. SEAP activity was determined in the supernatant using a colorimetric substrate, e.g. QUANTI-Blue™ or HEK-Blue™ Detection media (Invivo-Gen). Percentage inhibitions for compound dilutions were calculated between a DMSO control and maximum inhibition (by excess control compound) and an $IC_{50}$ value calculated using XLfit™ (4 parameter logistic model) in ActivityBase.

When tested in the reporter gene assay, certain compounds of the accompanying Examples were found to exhibit $IC_{50}$ values of 50 μM or better.

EXAMPLES

Nomenclature

Compounds were named with the aid of ACD/Name Batch (Network) ver. 12.0 or Accelyrs Draw 4.0

Abbreviations

| | |
|---|---|
| DCM: | Dichloromethane |
| DMF: | N,N-Dimethylformamide |
| DMSO: | Dimethylsulfoxide |
| $Et_2O$: | Diethyl ether |
| THF: | Tetrahydrofuran |
| r.t.: | Room temperature |
| br.: | Broad |
| M: | Mass |
| Brine: | Saturated aqueous sodium chloride solution |
| HPLC: | High Performance Liquid Chromatography |
| LCMS: | Liquid Chromatography Mass Spectrometry |
| ES+: | Electrospray Positive Ionisation |
| TEA: | Triethylamine |
| DIPEA: | N,N-di-iso-propylethylamine |
| DIAD: | Diisopropyl (E)-1,2-diazenedicarboxylate |
| CDI: | Carbonyl diimidazole |
| DIBAL-H: | Diisobutylaluminum hydride |
| bs.: | Broad singlet |
| $Boc_2O$: | Di-tert butyl dicarbonate |
| DME | dimethoxy ethane |
| TLC | thin layer chromatography |
| sat. | Saturated |
| Hex | hexane |
| aq. | aqueous |
| EtOAc: | Ethyl acetate |
| MeOH: | Methanol |
| $SiO_2$: | Silica |
| h: | Hour |
| AcOH: | Acetic acid |
| RT: | retention time |
| MeCN: | Acetonitrile |
| EtOH: | Ethanol |

The methanolic ammonia solution is made by mixing 100 mL of an aq. solution of 37% w/w of $NH_4OH$ in 900 mL of MeOH.

Analytical Conditions

All NMRs were obtained either at 300 MHz or 400 MHz. All reactions involving air or moisture-sensitive reagents were performed under a nitrogen atmosphere using dried solvents and glassware.

All compound LCMS data were determined by using the method below.

Method 1:
Waters Acquity-SQD, Waters Acquity UPLC BEH C18, 2.1×50 mm, 1.7 μm column
Mobile phase A: 10 mM Ammonium Formate+0.1% Ammonia
Mobile phase B: 95% MeCN+5% $H_2O$+0.1% Ammonia
Gradient program (Flow Rate 1.0 mL/min, Column Temperature 40° C.):

| Time | A % | B % |
|---|---|---|
| 0.00 | 95 | 5 |
| 0.50 | 95 | 5 |
| 1.75 | 5 | 95 |
| 2.00 | 5 | 95 |
| 2.25 | 95 | 5 |

Method 2 (M2):
Waters Acquity-SQD, Waters Acquity UPLC BEH C18, 2.1×50 mm, 1.7 μm column
Mobile phase A: water+0.05% formic acid
Mobile phase B: MeCN+0.035% formic acid
Gradient program (Flow Rate 0.9 ml/min, Column Temperature 55° C.):

| Time | A % | B % |
|---|---|---|
| 0.00 | 95 | 5 |
| 2.00 | 5 | 95 |
| 2.60 | 5 | 95 |
| 2.70 | 95 | 5 |
| 3.00 | 95 | 5 |

Method 3
Column: Waters XSelect (C18, 30×2.1 mm, 3.5 μm)
Flow: 1 mL/min Column temp: 35° C.
Eluent A: 0.1% Formic acid in acetonitrile
Eluent B: 0.1% Formic acid in water
Lin. Gradient: t=0 min 5% A, t=1.6 min 98% A, t=3 min 98% A
Detection: DAD (220-320 nm)
Detection: PDA (200-400 nm)
Detection: MSD (ESI pos/neg) mass range: 100-800
It will be apparent to the one skilled in the art that different retention times (RT) may be obtained for LCMS data if different analytical conditions are used.

Intermediate 1

Ethyl 2-(6-bromoimidazo[1,2-a]pyrazin-2-yl)acetate

To a solution of 5-bromo-2-amino-pyrazine (2.59 g, 14.89 mmol) in EtOH (100 mL) was added ethyl 4-chloro-3-oxo-butanoate (2.62 g, 15.93 mmol). The reaction was heated to reflux for 18 h. The reaction was cooled to r.t. and water (200 mL) was added, the mixture was extracted with DCM (2×200 mL). The organic layer was separated, dried ($MgSO_4$) and concentrated in vacuum. The residue was purified by preparative HPLC yielding the title compound as a brown solid (0.65 g, 15%). LCMS ($ES^+$) 284.0/286.0 $(M+H)^+$.

Intermediate 2

2-(6-bromoimidazo[1,2-a]pyrazin-2-yl)ethanol

To a solution of Intermediate 1 (1.0 g, 3.52 mmol) in THF (30 mL) at −78° C. was added DIBAL-H (9.00 mL, 9.00 mmol) drop wise. The reaction was stirred for 4 h at −78° C. to −40° C. The reaction was treated with excess $Na_2SO_4 \cdot 10H_2O$ and diluted with DCM (200 mL) and iPrOH (100 mL). The solid was filtered off and the filtrate was concentrated in vacuum to afford the title compound as brown oil (0.68 g, 80%).

LCMS (ES+) 242.0/244.0 (M+H)+.

Intermediate 3

1-(difluoromethoxy)-2-(dimethoxymethyl)benzene

To a solution of 2-(difluoromethoxy)benzaldehyde (5.51 g, 29.05 mmol) in MeOH (20 mL) was added trimethylorthoformate (4.13 mL, 37.76 mmol) and $LiBF_4$ (0.08 g, 0.87 mmol). The reaction mixture was heated to reflux for 4 h, cooled and treated with $NaHCO_3$ sat. solution (50 mL), extracted with EtOAc (50 mL), dried over $MgSO_4$ and concentrated in vacuo to afford the title compound as a yellow oil (6.30 g, 100%).

$^1$H NMR (400 MHz, $CDCl_3$) δ 7.55 (dd, J 7.6, 1.5 Hz, 1H), 7.28 (m, 1H), 7.18 (m, 1H), 7.08 (d, J 8.1 Hz, 1H), 6.40 (t, J 74.6 Hz, 1H), 5.53 (s, 1H), 3.32 (s, 6H).

Intermediate 4

1-[2-(difluoromethoxy)phenyl]-8-bromo-3,4-dihydro-1H-pyrano[4',3':4,5]imidazo[1,2-a]pyrazine

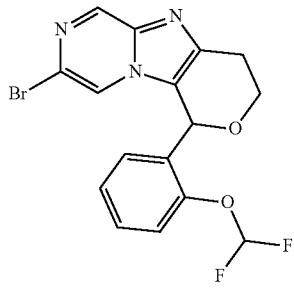 [SMILES: FC(F)Oc1ccccc1C1OCCc2nc3cnc(Br)cn3c21]

To a solution of Intermediate 2 (0.19 g, 0.78 mmol) in MeCN (3 mL), para-toluenesulfonic acid (0.01 g, 0.78 mmol) and Intermediate 3 (0.17 g, 0.78 mmol) were added, and the reaction mixture was heated to 100° C. for 18 h. The reaction mixture was cooled and treated with EtOAc (80 mL) and washed with water (3×10 mL). The organics were washed with brine (50 mL) and dried over $MgSO_4$ and concentrated in vacuo. The residue was purified by column chromatography ($SiO_2$, 0-3% MeOH/DCM ($NH_4OH$ 10%)), yielding the title compound as a brown solid (0.06 g, 19%).

$^1$H NMR (400 MHz, $CDCl_3$) δ 8.84 (s, 1H), 7.42 (m, 1H), 7.27 (m, 2H), 7.16 (t, J 7.3 Hz, 1H), 6.91 (d, J 7.6 Hz, 1H), 6.58 (dd, $J_1$ 75.3 Hz, $J_2$ 72.2 Hz, 1H), 6.25 (s, 1H), 4.20 (m, 1H), 3.96 (m, 1H), 3.21 (m, 1H), 3.03 (m, 1H). LCMS (ES+) 396.0/398.0 (M+H)+.

Intermediate 5

Ethyl 6-bromoimidazo[1,2-a]pyrazine-2-carboxylate

2-Amino-5-bromopyrazine (100 g, 575 mmol) was dissolved in anhydrous 1,4-dioxane (2 L) and ethylbromopyruvate (155 g, 636 mmol, 100 mL) was added to the mechanically stirred solution. The mixture was heated to 95° C. and stirred overnight.

Mixture was cooled to room temperature and triethylamine (69.8 g, 690 mmol, 96 mL) was added. The mixture was stirred for 1 hour at ambient temperature.

The mixture was filtered over kieselguhr and rinsed with DCM/EtOH (9:1). The filtrate was concentrated and co-evaporated with $Et_2O$. The resulting residue was triturated with water and filtered, the solids rinsed with water and $Et_2O$ to give a crude solid, which was purified by filtration through a large plug of silica (~1 kg). Eluent 95:5 DCM/EtOH to give after evaporation of the solvents the title compound as a beige solid (80 g). H NMR (400 MHz, DMSO-d6) δ 9.10-9.03 (m, 1H), 8.93 (d, J=1.4 Hz, 1H), 8.58 (d, J=0.6 Hz, 1H), 4.35 (q, J=7.1 Hz, 2H), 1.34 (t, J=7.1 Hz, 3H).

LCMS Method 3 RT 1.61 minutes, m/z 270, 272 (M+H)+.

Intermediate 6

(6-bromoimidazo[1,2-a]pyrazin-2-yl)methanol

A mechanically stirred suspension of Intermediate 5 (98.4 g, 364 mmol)

In anhydrous THF (1800 mL) was cooled to −70/−74° C. under a nitrogen atmosphere. DIBAL-H 1M in hexanes (800 mmol, 800 mL) was added dropwise under a nitrogen atmosphere over a period of ~2 hours. The reaction temperature was not allowed to exceed ~70° C. during the addition of DIBAL-H. After addition of the DIBAL-H was complete, the reaction mixture was kept below −70° C. for about 30 minutes, after which time the cooling bath was removed and the reaction mixture was allowed to slowly warm to room temperature over a period of several hours.

The reaction mixture was quenched by slow addition of Sodium sulfate decahydrate (392 g, 1218 mmol) while cooling with ice/water. The mixture was stirred slowly overnight maintaining the temperature<25° C. The mixture was filtered over a large glass sintered funnel and the residue was washed repeatedly with DCM/MeOH 1:1 and the combined filtrates were concentrated in vacuo and co-evaporated with toluene affording 78.2 g of a sand colored solid.

The solid was triurated with di-isopropyl ether to yield a solid which was isolated by filtration and washed with cold di-isopropylether. The filtrates were concentrated in vacuo and the residue again tritrated with di-isopropyl ether to yield a further batch of solid. The combined solids provided the title compound as a beige powder (66.8 g).

LCMS Method 3 RT 0.43 minutes, m/z 228, 230 (M+H)+.

Intermediate 7

5-chloro-2-(difluoromethoxy)benzaldehyde

To a solution of 5-chloro-2-hydroxybenzaldehyde (200 g, 1277 mmol) in 1,4-dioxane (800 mL) was added a solution of sodium hydroxide (307 g, 7664 mmol) in water (800 mL) and Sodium dithionite (22.24 g, 128 mmol). The reaction mixture was heated to 65° C. and chlorodifluoromethane (133 g, 1533 mmol) was purged through the reaction mixture under vigorous mechanical stirring over ~30-40 minutes. When the reaction was complete (as determined by the amount of chlorodifluoromethane used), it was cooled immediately with ice/water to ambient temperature. The aqueous and organic layers were separated and the aqueous layer extracted 3 times with diethylether. The combined organic layers were washed with brine, dried over Na$_2$SO$_4$, filtered and concentrated in vacuo yielding the title compound as an orange oil (136 g).

Intermediate 8

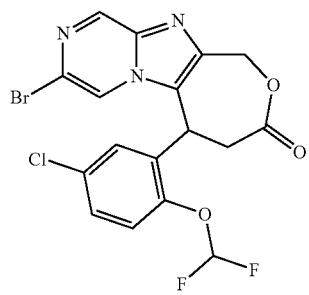 [SMILES: O=C1CC(c2cc(Cl)ccc2OC(F)F)c2c(nc3cnc(Br)cn23)CO1]

3-Bromo-6-[5-chloro-2-(difluoromethoxy)phenyl]-6,10-dihydrooxepino[3',4':4,5]imidazo[1,2-a]pyrazin-8(7H)-one A solution of Intermediate 6 (66.5 g, 292 mmol), Intermediate 7 (113 g, 437 mmol), Meldrums acid (63 g, 431 mmoL, 1.5 eq) and (S)-pyrrolidine-2-carboxylic acid (1.68 g, 14.58 mmol) in anhydrous acetonitrile (1000 mL) was heated to 90° C. and stirred for 4 days under a nitrogen atmosphere. The reaction mixture was concentrated in vacuo and the residue taken up in EtOAc. The mixture was filtered over a sintered glass funnel and the residue washed with EtOAc. The filtrate was washed twice with brine, dried over Na$_2$SO$_4$, filtered and concentrated in vacuo yielding the title compound as a dark oily solid and used as such in the next step.

LCMS Method 3 RT 2.06 minutes, m/z 460 (M+H)$^+$.

Intermediate 9

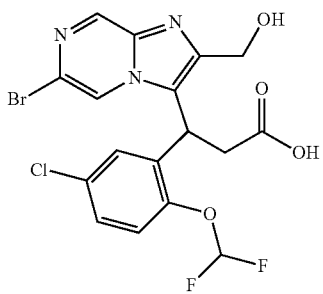 [SMILES: O=C(O)CC(c1cc(Cl)ccc1OC(F)F)c1c(CO)nc2cnc(Br)cn12]

3-[6-bromo-2-(hydroxymethyl)imidazo[1,2-a]pyrazin-3-yl]-3-[5-chloro-2-(difluoromethoxy)phenyl]propanoic acid Intermediate 8 (225 g, 338 mmol) was stirred in 2M aqueous sodium hydroxide solution (2000 mL) for 60 minutes until all the material was dissolved. The solution was decanted and acidified to pH=6 with concentrated aqueous HCl (434 g, 4400 mmol, 361 ml, 37%). The solution was neutralized by adding solid NaHCO$_3$ (until gas evolution ceased) and extracted twice with EtOAc (1 L). The aqueous layer was acidified again to pH=6 and further extracted with 2×1000 mL of EtOAc, the organics dried over Na$_2$SO$_4$, filtered and concentrated in vacuo, co-evaporated with DCM to give the title compound as a yellow/brown solid (169 g). The solid was triturated with di-isopropylether to give the title compound as a yellow solid (125 g, 77%).

LCMS Method 3 RT 1.99 minutes, m/z 478 (M+H)$^+$.

Intermediate 10

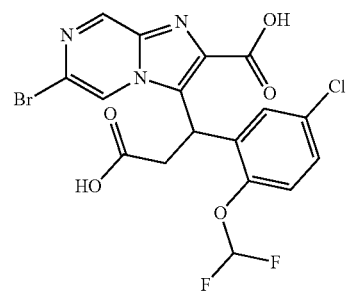 [SMILES: O=C(O)CC(c1cc(Cl)ccc1OC(F)F)c1c(C(=O)O)nc2cnc(Br)cn12]

6-bromo-3-[1-[5-chloro-2-(difluoromethoxy)phenyl]-3-hydroxy-3-oxo-propyl]imidazo[1,2-a]pyrazine-2-carboxylic acid Intermediate 9 (125 g, 262 mmol) was suspended in acetonitrile (1 L) and water (9.45 g, 524 mmol, 9.45 ml). The mixture was cooled to 0° C. followed by addition of periodic acid (239 g, 1049 mmol) and chromium trioxide (0.524 g, 5.24 mmol) in 1 portion. The mixture was stirred at 0° C. for 15 minutes then allowed to warm to room temperature. The mixture was warmed to 45° C. and stirred for 2.5 hours the mixture was filtered over a plug of celite and the filtrate was concentrated in vacuo. The residue was partitioned between water (1 L) and Et$_2$O (750 mL). The layers were separated and the aqueous phase extracted with Et$_2$O (750 ml). The combined organic layers were washed with brine, dried over (Na$_2$SO$_4$), filtered and evaporated to dryness to give 124 g of a brown solid. The solid was triturated with EtOAc to give the title compound as a white solid (72 g).

LCMS Method 3 RT 1.90 minutes, m/z 492 (M+H)$^+$.

Intermediate 11

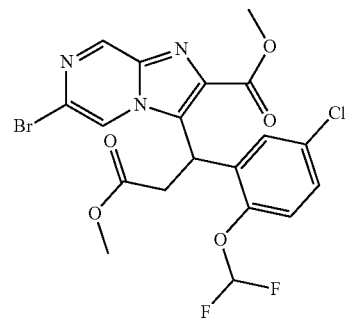 [SMILES: COC(=O)CC(c1cc(Cl)ccc1OC(F)F)c1c(C(=O)OC)nc2cnc(Br)cn12]

Methyl 6-bromo-3-[1-[5-chloro-2-(difluoromethoxy)phenyl]-3-methoxy-3-oxo-propyl]imidazo[1,2-a]pyrazine-2-carboxylate Iodomethane (41.7 g, 293 mmol, 18.35 mL) was added to a stirred mixture of Intermediate 10 (72 g, 147 mmol) and potassium carbonate (60.8 g, 440 mmol) in N,N-dimethylformamide (500 mL). After 2.5 hours additional potassium carbonate (15.21 g, 110 mmol) and iodomethane (10.41 g, 73.4 mmol, 4.59 mL) were added. The reaction mixture was poured into water (2.5 L) and a white suspension formed. The mixture was stirred for 30 minutes then filtered. The filtercake was rinsed with water and dried to give the title compound (70.6 g) as white solid.

LCMS Method 3 RT 2.10 minutes, m/z 520 (M+H)+

Intermediate 12

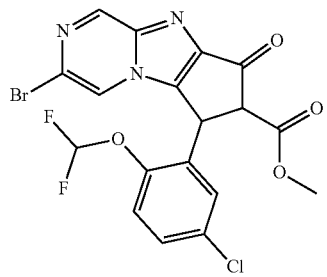 [SMILES: COC(=O)C1C(=O)c2nc3cnc(Br)cn3c2C1c1cc(Cl)ccc1OC(F)F]

Methyl 3-bromo-6-[5-chloro-2-(difluoromethoxy)phenyl]-8-oxo-7,8-dihydro-6H-cyclopenta[4,5]imidazo[1,2-a]pyrazine-7-carboxylate Intermediate 11 (17 g, 32.8 mmol) was suspended in toluene (250 mL) and cooled to 0° C. Sodium tert butoxide (7.87 g, 82 mmol) was added in 1 portion. Mixture turned dark green and stirring was continued at 0° C. After 90 minutes saturated aqueous NH4Cl solution (400 mL) was added and the mixture was vigorously stirred. The mixture was extracted with EtOAc (×3) and the combined organics were washed with brine, dried (Na2SO4), filtered and evaporated to dryness to give a crude solid. The solid was triturated with a 1:1 mixture of Et2O and iPr2O to give a red solid. Additional material can be isolated from the mother liquors by column chromatography on silica (40% EtOAc in heptane), to provide the title compound as red/brown solid (5.5 g).

LCMS Method 3 RT 2.06 minutes, m/z 488 (M+H)+.

Intermediate 13

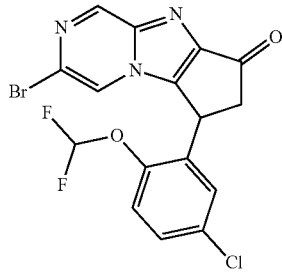 [SMILES: O=C1CC(c2cc(Cl)ccc2OC(F)F)c2c1nc1cnc(Br)cn21]

3-Bromo-6-[5-chloro-2-(difluoromethoxy)phenyl]-6,7-dihydro-8H-cyclopenta[4,5]imidazo[1,2-a]pyrazin-8-one Intermediate 12 (1 g, 2.06 mmol) was dissolved in DMSO (20 mL) followed by addition of sodium chloride (0.132 g, 2.26 mmol) and water (0.06 mL). The mixture was stirred at 100° C. until LCMS showed the reaction to be complete. The reaction mixture was cooled to room temperature and poured into water (400 mL). The mixture was extracted with EtOAc (×3) and the combined organic layers were washed with brine, dried over Na2SO4, filtered and the volatiles removed in vacuo to give the title compound as an off white solid.

LCMS Method 3 RT 2.02 minutes, m/z 428 (M+H)+.

Intermediates 14 & 15

(6R,8R)-2-bromo-8-[5-chloro-2-(difluoromethoxy)phenyl]-7,8-dihydro-6H-cyclopenta[1,2]imidazo[3,4-b]pyrazin-6-ol and (6S,8S)-2-bromo-8-[5-chloro-2-(difluoromethoxy)phenyl]-7,8-dihydro-6H-cyclopenta[1,2]imidazo[3,4-b]pyrazin-6-ol

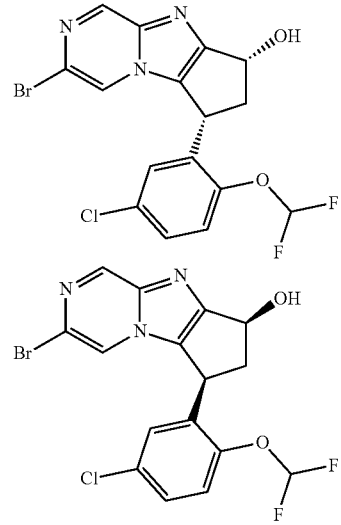

Intermediate 13 (410 mg, 0.96 mmol) was dissolved in THF (15 ml) under argon. After cooling to −78° C. L-Selectride was added dropwise (956 µl, 1 M in THF) with stirring. After 30 min additional L-Selectride was added (23 µl). 2.5 h later methanol was added (2.5 ml) followed by 1 N sodium hydroxide solution (2.5 ml). After warming to room temperature the aqueous phase was extracted with EtOAc (3×). The combined organic layers were dried over sodium sulphate, filtered and concentrated in vacuo. The residue was purified by column chromatography (SiO2 24 g, DCM/EtOH 100/0 to 90/10 in 65 min), yielding the title compounds as a racemic mixture (209 mg, 51%).

$^1$H NMR (400 MHz, DMSO-$d_6$) δ 8.93 (d, 1H), 8.31 (d, 1H), 7.42 (dd, 1H), 7.33 (t, 1H), 7.30 (d, 1H), 6.95 (d, 1H), 5.72 (d, 1H), 5.14 (ddd, 1H), 4.75 (dd, 1H), 3.38-3.49 (m, 1H), 2.10 (dt, 1H). LCMS-M2 (ES+) 1.68 min, 430.0/432.0 (M+H)+.

Intermediates 16 & 17

2-[[(6R,8R)-2-bromo-8-[5-chloro-2-(difluoromethoxy)phenyl]-7,8-dihydro-6H-cyclopenta[1,2]imidazo[3,4-b]pyrazin-6-yl]oxy]acetonitrile and 2-[[(6S,8S)-2-bromo-8-[5-chloro-2-(difluoromethoxy)phenyl]-7,8-dihydro-6H-cyclopenta[1,2]imidazo[3,4-b]pyrazin-6-yl]oxy]acetonitrile

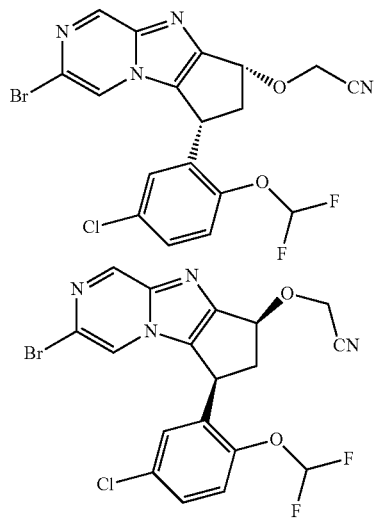

To a solution of Intermediates 14 & 15 (105 mg, 240 μmol) in THF (5 ml) sodium hydride (22 mg, 60%) was added with stirring at 0° C. After 1 h bromoacetonitrile (70 μl, 980 μmol) was added dropwise. The ice bath was removed and the reaction mixture stood over night. To complete the reaction the mixture was cooled to 0° C. again and treated with further sodium hydride (22 mg, 60%). Then the ice bath was removed and after 2 h water was added. The mixture was extracted with EtOAc (3×) and the combined organics were dried over sodium sulphate, filtered and concentrated in vacuo. The residue was purified by column chromatography (SiO$_2$ 4 g, DCM/EtOH 100/0 to 90/10 in 65 min) and the isolated product was lyophylised from water/MeCN, yielding the title compounds as a racemic mixture (71 mg, 62%).

$^1$H NMR (400 MHz, DMSO-d$_6$) δ 9.01 (d, 1H), 8.46 (d, 1H), 7.43 (dd, 1H), 7.31 (t, 1H), 7.30 (d, 1H), 6.84 (d, 1H), 5.75 (s, 1H), 5.15 (dd, 1H), 4.82 (dd, 1H), 4.63-4.75 (m, 2H), 3.48-3.58 (m, 1H), 2.26 (dt, 1H). LCMS-M2 (ES+) 1.83 min, 469.0/471.0 (M+H)$^+$.

Intermediates 18 & 19

2-[[(6R,8R)-2-bromo-8-[5-chloro-2-(difluoromethoxy)phenyl]-7,8-dihydro-6H-cyclopenta[1,2]imidazo[3,4-b]pyrazin-6-yl]oxy]acetamide and 2-[[(6S,8S)-2-bromo-8-[5-chloro-2-(difluoromethoxy)phenyl]-7,8-dihydro-6H-cyclopenta[1,2]imidazo[3,4-b]pyrazin-6-yl]oxy]acetamide

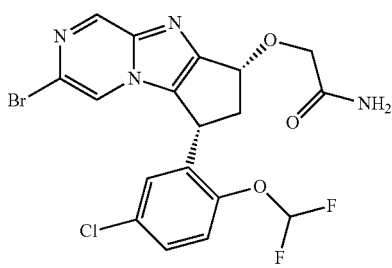

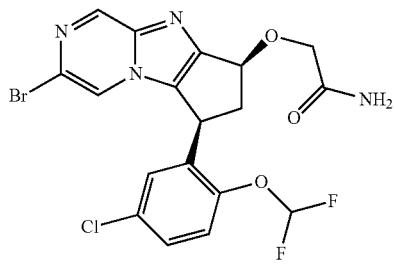

To a solution of Intermediates 16 & 17 (81 mg, 170 μmol) a solution of HBr in acetic acid (1.5 ml, wt=45%) was added with stirring. After 1 h saturated sodium bicarbonate solution was added to neutralise the reaction mixture. After extraction with DCM the combined organics were dried over sodium sulphate, filtered and concentrated in vacuo. The residue was purified by column chromatography (SiO$_2$ 4 g, DCM/EtOH 100/0 to 90/10 in 65 min), yielding the title compounds as a racemic mixture (46 mg, 55%).

$^1$H NMR (400 MHz, DMSO-d$_6$) δ 8.98 (d, 1H), 8.39 (d, 1H), 7.42 (dd, 1H), 7.32 (t, 1H), 7.30 (d, 1H), 7.27 (br s, 1H), 7.09 (br s, 1H), 6.94 (d, 1H), 5.05 (dd, 1H), 4.79 (dd, 1H), 4.09-4.18 (m, 2H), 3.42-3.53 (m, 1H), 2.34 (dt, 1H). LCMS-M2 (ES+) 1.65 min, 487.0/489.0 (M+H)$^+$.

Example 1

1-[2-(difluoromethoxy)phenyl]-8-(6-methoxypyridin-3-yl)-3,4-dihydro-1H-pyrano[4',3':4,5]imidazo[1,2-a]pyrazine

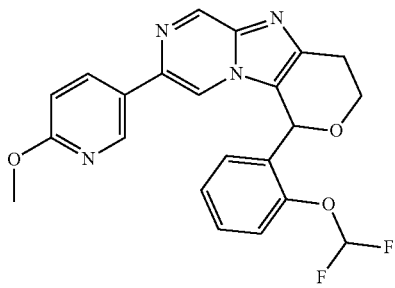 [SMILES: COc1ccc(-c2cn3c4c(nc3cn2)CCOC4c2ccccc2OC(F)F)cn1]

To a solution of Intermediate 4 (0.22 g, 0.63 mmol), in 1,4-dioxane/water (4.5/0.5 mL), K$_3$PO$_4$ (0.27 g, 1.25 mmol), (6-methoxy-3-pyridyl)boronic acid (0.14 g, 0.94 mmol) and Pd$_2$(dba)$_3$ (0.0057 g, 0.0063 mmol, 0.01 eq.) were added and the reaction was heated to 85° C. for 5 h. The reaction mixture was cooled and treated with water (10 mL), extracted with EtOAc (20 mL), the organics were washed with brine (20 mL), dried over MgSO$_4$, and concentrated in vacuo. The residue was purified by column chromatography (SiO$_2$, 0-3% MeOH/DCM (NH$_4$OH 10%)), yielding the title compound as an orange solid (75 mg, 28%). LCMS (ES$^+$) RT 1.45 min, 425.0 (M+H)$^+$.

Example 2

1-[2-(difluoromethoxy)phenyl]-8-[2-(morpholin-4-yl)pyrimidin-5-yl]-3,4-dihydro-1H-pyrano[4',3':4,5]imidazo[1,2-a]pyrazine

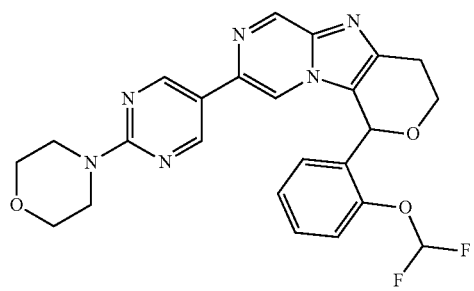 [SMILES: FC(F)Oc1ccccc1C1OCCc2nc3cnc(-c4cnc(N5CCOCC5)nc4)cn3c21]

The title compound was prepared from Intermediate 4 and 2-morpholinopyrimidin-5-ylboronic acid following a method analogous to the one described for Example 1.

LCMS (ES+) RT 1.41 min, 481.0 (M+H)+.

Example 3

5-{1-[2-(difluoromethoxy)phenyl]-3,4-dihydro-1H-pyrano[4',3':4,5]imidazo[1,2-a]pyrazin-8-yl}pyridin-2(1H)-one

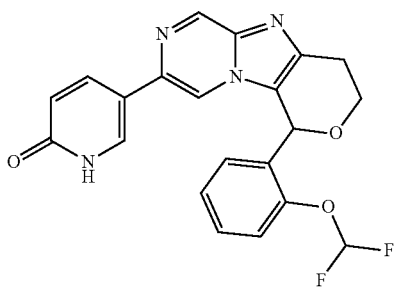 [SMILES: O=c1ccc(-c2cn3c4c(nc3cn2)CCOC4c2ccccc2OC(F)F)c[nH]1]

To a solution of Example 1 (0.07 g, 0.17 mmol) in 1,4-dioxane (3 mL) was added HBr (0.15 mL, 0.6 mmol, 48% aq. sol.). The reaction mixture was heated under microwave irradiation at 125° C. for 0.3 h. The reaction mixture was then taken up in EtOAc, washed with an aq. sat. solution of NaHCO$_3$. The organic phase was dried over anhydrous MgSO$_4$ and concentrated in vacuo. The residue was purified by preparative HPLC.

$^1$H NMR (400 MHz, CDCl$_3$) δ: 9.03 (d, 1H, J 0.6 Hz), 7.94 (dd, J 1.5, 0.7 Hz, 1H), 7.59 (m, 1H), 7.47 (m, 1H), 7.36 (m, 2H), 7.22 (m, 2H), 7.05 (m, 1H), 6.62 (m, 2H), 6.39 (d, J 0.5 Hz, 1H), 4.29 (m, 1H), 4.05 (m, 1H), 3.26 (m, 1H), 3.08 (m, 1H).

LCMS (ES+) RT 1.21 min, 411.0 (M+H)+.

Examples 4 & 5

Enantiomer 1: (1S or R)-8-bromo-1-[2-(difluoromethoxy)phenyl]-3,4-dihydro-1H-pyrano[4',3':4,5]imidazo[1,2-a]pyrazine; enantiomer 2: (1R or S)-8-bromo-1-[2-(difluoromethoxy)phenyl]-3,4-dihydro-1H-pyrano[4',3':4,5]imidazo[1,2-a]pyrazine

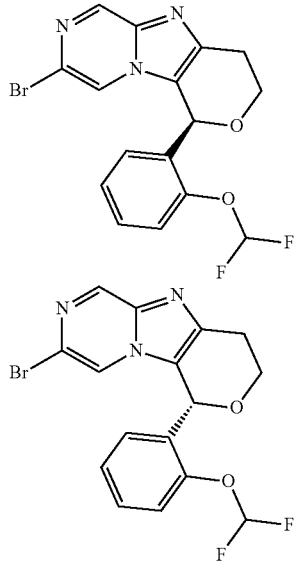

The title compounds were isolated by purification of 60 mg of Intermediate 4 under SFC conditions on WhelkO-01 (R,R) (50*227 mm*mm, flow 360 mL/min, 25° C., CO$_2$+ 20% i-PrOH, injection of 5 mL solution at a concentration of 20 g/L).

The first eluting enantiomer (RT 7.31 min) was collected and the fractions were evaporated to yield (enantiomer 1) ((1S or R)-8-bromo-1-[2-(difluoromethoxy)phenyl]-3,4-dihydro-1H-pyrano[4',3':4,5]imidazo[1,2-a]pyrazine (16 mg, 27%, Example 4).

LCMS (ES+) RT 1.40 min, 396.0/398.0 (M+H)+.

The second eluting enantiomer (RT 8.99 min) was collected and the fractions were evaporated to yield (enantiomer 2) (1R or S)-8-bromo-1-[2-(difluoromethoxy)phenyl]-3,4-dihydro-1H-pyrano[4',3':4,5]imidazo[1,2-a]pyrazine (13 mg, 22%, Example 5).

LCMS (ES+) RT 1.40 min, 396.0/398.0 (M+H)+.

Examples 6 & 7

Enantiomer 1: (1S or R)-8-bromo-1-[2-(difluoromethoxy)phenyl]-3,4-dihydro-1H-pyrano[4',3':4,5]imidazo[1,2-a]pyrazine; enantiomer 2: (1R or S)-8-bromo-1-[2-(difluoromethoxy)phenyl]-3,4-dihydro-1H-pyrano[4',3':4,5]imidazo[1,2-a]pyrazine

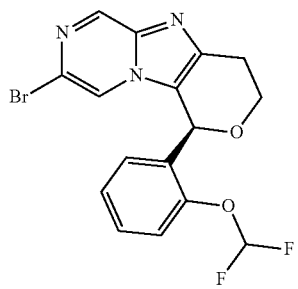

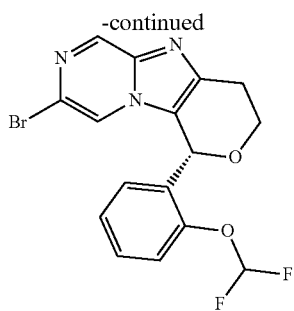

The title compounds were isolated by purification of 60 mg of Intermediate 4 under SFC conditions on WhelkO-01 (R,R) (50*227 mm*mm, flow 360 mL/min, 25° C., CO$_2$+ 20% i-PrOH, injection of 5 mL solution at a concentration of 20 g/L).

The first eluting enantiomer (RT 7.31 min) was collected and the fractions were evaporated to yield (enantiomer 1) ((1S or R)-8-bromo-1-[2-(difluoromethoxy)phenyl]-3,4-dihydro-1H-pyrano[4',3':4,5]imidazo[1,2-a]pyrazine (16 mg, 27%, Example 4).

LCMS (ES+) RT 1.40 min, 396.0/398.0 (M+H)$^+$.

The second eluting enantiomer (RT 8.99 min) was collected and the fractions were evaporated to yield (enantiomer 2) (1R or S)-8-bromo-1-[2-(difluoromethoxy)phenyl]-3,4-dihydro-1H-pyrano[4',3':4,5]imidazo[1,2-a]pyrazine (13 mg, 22%, Example 5).

LCMS (ES+) RT 1.40 min, 396.0/398.0 (M+H)$^+$.

Examples 8 & 9

Enantiomer 1: (6R,8R)-8-[5-chloro-2-(difluoromethoxy)phenyl]-2-[6-(1-hydroxy-1-methyl-ethyl)-3-pyridyl]-7,8-dihydro-6H-cyclopenta[1,2]imidazo[3,4-b]pyrazin-6-ol; enantiomer 2: (6S,8S)-8-[5-chloro-2-(difluoromethoxy)phenyl]-2-[6-(1-hydroxy-1-methyl-ethyl)-3-pyridyl]-7,8-dihydro-6H-cyclopenta[1,2]imidazo[3,4-b]pyrazin-6-ol

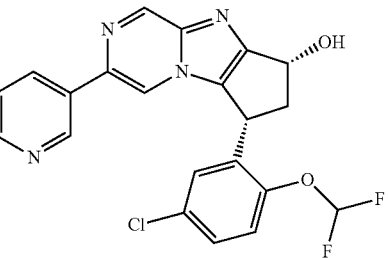

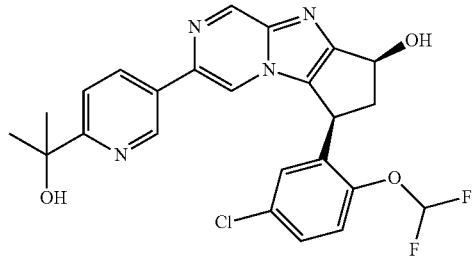

To a solution of Intermediates 14 & 15 (85 mg, 200 μmol) in DME/water (4/1 ml) Na$_2$CO$_3$ (84 mg, 790 μmol), 2-(5-(4,4,5,5-tetramethyl-1,3,2-dioxaborolan-2-yl)pyridin-2-yl)propan-2-ol (109 mg, 390 μmol) and 1,1'-bis(diphenylphosphino)ferrocene-palladium(II)dichloride dichloromethane complex (32 mg, 40 μmol) were added and the reaction mixture was heated to 100° C. for 15 min in a microwave oven. The reaction mixture was cooled, treated with water and extracted with EtOAc (3×). The combined organics were dried over MgSO$_4$, filtered and concentrated in vacuo. The residue was purified by column chromatography (SiO$_2$ 4 g, DCM/EtOH 100/0 to 90/10 in 65 min), yielding the title compounds as a racemic mixture (93 mg) that required further purification. After reverse phase column chromatography (column: Agilent Prep-C18 (21.5×250 mm) 10 μm, flow 40 ml/min; gradient: MeCN/water 10/90 (0 min), 90/10 (12.5 min), 90/10 (15 min) 55 mg of the racemate was obtained.

The title compounds were isolated by separation of the racemate on Chiralpak IC [(250*30 mm*mm), 5 μm, flow 30 ml/min, rt, Hep:EtOH:MeOH 5:1:1+0.02% TFA].

The first eluting enantiomer (RT 15.7 min) was collected and the combined fractions were evaporated and lyophilised from MeCN/water. The residue was treated with a mixture of water, saturated sodium bicarbonate solution and DCM. After extracting the aqueous solution with DCM (3×) the combined organics were dried over sodium sulphate, filtered and concentrated in vacuo. After a further reverse phase column chromatography [column: Agilent Prep-C18 (21.5×250 mm) 10 μm, flow 40 ml/min; gradient: MeCN/water 10/90 (0 min), 90/10 (12.5 min), 90/10 (15 min)] and lyophilisation from water/MeCN enantiomer 1, (6R,8R)-8-[5-chloro-2-(difluoromethoxy)phenyl]-2-[6-(1-hydroxy-1-methyl-ethyl)-3-pyridyl]-7,8-dihydro-6H-cyclopenta[1,2]imidazo[3,4-b]pyrazin-6-ol, was obtained (17 mg, 18%, Example 8).

$^1$H NMR (DMSO-d$_6$) δ: 9.19 (d, 1H), 8.99 (d, 1H), 8.57 (d, 1H), 8.26 (dd, 1H), 7.74 (d, 1H), 7.41 (dd, 1H), 7.40 (t, 1H), 7.32 (d, 1H), 6.97 (d, 1H), 5.70 (br d, 1H), 5.25 (s, 1H), 5.13-5.19 (m, 1H), 4.82 (dd, 1H), 3.43-3.53 (m, 1H), 2.14 (dt, 1H), 1.45 (s, 6H). LCMS-M2 (ES+) RT 1.50 min, 487.2 (M+H)$^+$.

The second eluting enantiomer (RT 22.7 min) was collected and treated as described for enantiomer 1 tp afford enantiomer 2, (6S,8S)-8-[5-chloro-2-(difluoromethoxy)phenyl]-2-[6-(1-hydroxy-1-methyl-ethyl)-3-pyridyl]-7,8-dihydro-6H-cyclopenta[1,2]imidazo[3,4-b]pyrazin-6-ol (19 mg, 20%, Example 9).

$^1$H NMR (DMSO-d$_6$) δ: 9.19 (d, 1H), 8.99 (d, 1H), 8.57 (d, 1H), 8.26 (dd, 1H), 7.74 (d, 1H), 7.41 (dd, 1H), 7.40 (t, 1H), 7.32 (d, 1H), 6.97 (d, 1H), 5.70 (d, 1H), 5.26 (s, 1H), 5.13-5.19 (m, 1H), 4.82 (dd, 1H), 3.43-3.52 (m, 1H), 2.15 (dt, 1H), 1.45 (s, 6H). LCMS-M2 (ES+) RT 1.50 min, 487.2 (M+H)$^+$.

Examples 10 & 11

Enantiomer 1: 2-[[(6R,8R)-8-[5-chloro-2-(difluoromethoxy)phenyl]-2-[6-(1-hydroxy-1-methyl-ethyl)-3-pyridyl]-7,8-dihydro-6H-cyclopenta[1,2]imidazo[3,4-b]pyrazin-6-yl]oxy]acetamide; enantiomer 2: 2-[[(6S,8S)-8-[5-chloro-2-(difluoromethoxy)phenyl]-2-[6-(1-hydroxy-1-methyl-ethyl)-3-pyridyl]-7,8-dihydro-6H-cyclopenta[1,2]imidazo[3,4-b]pyrazin-6-yl]oxy]acetamide

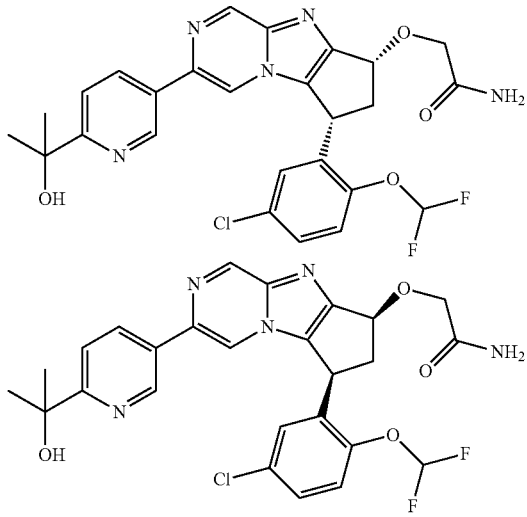

To a solution of Intermediates 18 & 19 (44 mg, 90 µmol) in DME/water (4/1 ml) Na$_2$CO$_3$ (39 mg, 360 µmol), 2-(5-(4,4,5,5-tetramethyl-1,3,2-dioxaborolan-2-yl)pyridin-2-yl)propan-2-ol (50 mg, 180 µmol) and 1,1'-bis(diphenylphosphino)ferrocene-palladium(II)dichloride dichloromethane complex (15 mg, 20 µmol) were added and the reaction mixture was heated to 100° C. for 15 min in a microwave oven. The reaction mixture was cooled, treated with water and extracted with EtOAc (3×). The combined organics were dried over MgSO$_4$, filtered and concentrated in vacuo. The residue was purified by column chromatography (SiO$_2$ 4 g, DCM/EtOH 100/0 to 85/15 in 65 min), yielding the title compounds as a racemic mixture (48 mg).

The title compounds were isolated by separation of the racemate on Chiralpak IF [(250*30 mm*mm), 5 µm, flow 30 ml/min, rt, heptane:EtOH:MeOH 2:1:1+0.1% diethylamine].

The first eluting enantiomer (RT 13.4 min) was collected and the combined fractions were evaporated and lyophilised from MeCN/water to yield enantiomer 1, (6R,8R)-8-[5-chloro-2-(difluoromethoxy)phenyl]-2-[6-(1-hydroxy-1-methyl-ethyl)-3-pyridyl]-7,8-dihydro-6H-cyclopenta[1,2]imidazo[3,4-b]pyrazin-6-ol (16 mg, 32%, Example 10).

$^1$H NMR (DMSO-d$_6$) δ: 9.24 (d, 1H), 9.01 (d, 1H), 8.65 (d, 1H), 8.28 (dd, 1H), 7.74 (d, 1H), 7.42 (dd, 1H), 7.38 (t, 1H), 7.32 (d, 1H), 7.28 (br s, 1H), 7.10 (br s, 1H), 6.94 (d, 1H), 5.26 (s, 1H), 5.07 (dd, 1H), 4.86 (dd, 1H), 4.16 (s, 2H), 3.48-3.58 (m, 1H), 2.38 (dt, 1H), 1.45 (s, 6H). LCMS-M2 (ES+) RT 1.48 min, 544.2 (M+H)$^+$.

The second eluting enantiomer (RT 16.4 min) was collected and the fractions were evaporated and lyophilised from MeCN/water to yield enantiomer 2, 2-[[(6S,8S)-8-[5-chloro-2-(difluoromethoxy)phenyl]-2-[6-(1-hydroxy-1-methyl-ethyl)-3-pyridyl]-7,8-dihydro-6H-cyclopenta[1,2]imidazo[3,4-b]pyrazin-6-yl]oxy]acetamide (16 mg, 33%, Example 11).

$^1$H NMR (DMSO-d$_6$) δ: 9.24 (d, 1H), 9.01 (d, 1H), 8.65 (d, 1H), 8.28 (dd, 1H), 7.74 (d, 1H), 7.42 (dd, 1H), 7.38 (t, 1H), 7.32 (d, 1H), 7.28 (br s, 1H), 7.10 (br s, 1H), 6.94 (d, 1H), 5.26 (s, 1H), 5.07 (dd, 1H), 4.86 (dd, 1H), 4.16 (s, 2H), 3.48-3.58 (m, 1H), 2.32-2.41 (dt, 1H), 1.45 (s, 6H). LCMS-M2 (ES+) RT 1.48 min, 544.2 (M+H)$^+$.

The invention claimed is:

1. A compound of formula (I) or an N-oxide thereof, or a pharmaceutically acceptable salt or solvate thereof, or a glucuronide derivative thereof, or a co-crystal thereof:

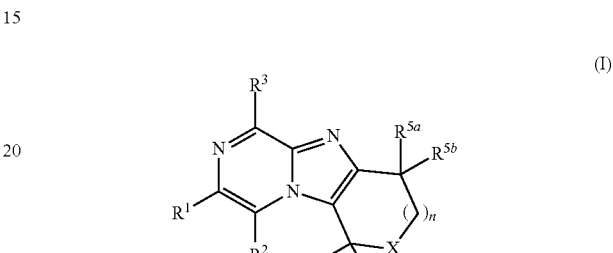

wherein n represents an integer equal to 0 or 1;

Y represents aryl or heteroaryl, any of which groups may be optionally substituted by one or more substituents selected from halogen, cyano, amino, $C_{1-6}$ alkyl, $C_{1-6}$ alkylsulphonyl, $C_{1-6}$ alkoxy, trifluoromethoxy and difluoromethoxy;

X represents oxygen, sulphur, S(O), or N(R$^d$), or a straight or branched $C_{1-4}$ alkylene chain;

R$^1$ represents halogen, heteroaryl or (C$_{3-7}$)heterocycloalkyl-heteroaryl any of which groups may be optionally substituted by one or more substituents selected from hydroxy, hydroxy(C$_{1-6}$ alkyl) and C$_{1-6}$alkoxy;

R$^2$ and R$^3$ independently represent hydrogen, halogen or C$_{1-6}$ alkyl;

R$^4$ represents hydrogen, hydroxy, halogen or trifluoromethyl;

R$^{5a}$ represents hydrogen, hydroxy or —OR$^a$;

R$^{5b}$ represents hydrogen; and

R$^a$ represents $C_{1-6}$ alkyl, aryl(C$_{1-6}$)alkyl or heteroaryl (C$_{1-6}$)alkyl, any of which groups may be optionally substituted by one or more substituents selected from $C_{1-6}$ alkoxy, oxo and aminocarbonyl; and R$^d$ represents hydrogen or $C_{1-6}$ alkyl.

2. The compound according to claim 1 represented by formula (IIA), or an N-oxide thereof, or a pharmaceutically acceptable salt or solvate thereof, or a glucuronide derivative thereof, or a co-crystal thereof,

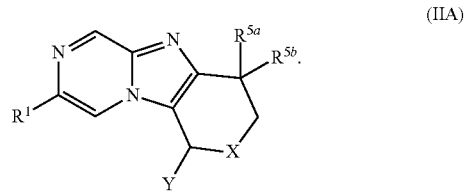

3. The compound according to claim 2 represented by formula (IIA-AB), or an N-oxide thereof, or a pharmaceutically acceptable salt or solvate thereof, or a glucuronide derivative thereof, or a co-crystal thereof,

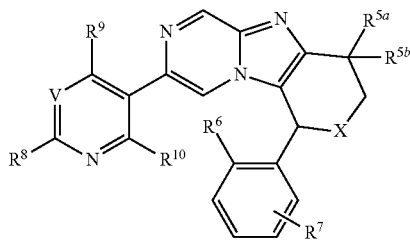

(IIA-AB)

wherein
V represents C—$R^{11}$ or N;
$R^6$ represents hydrogen, halogen, $C_{1-6}$ alkyl, trifluoromethyl, $C_{1-6}$ alkoxy, difluoromethoxy or trifluoromethoxy;
$R^7$ represents hydrogen, halogen, cyano, $C_{1-6}$ alkyl, trifluoromethyl, difluoromethoxy or amino;
$R^8$ represents hydroxy, hydroxy($C_{1-6}$)alkyl, $C_{1-6}$ alkoxy; and
$R^9$, $R^{10}$ and $R^{11}$ independently represent hydrogen.

4. The compound according to claim 2, wherein X represents oxygen.

5. The compound according to claim 1 represented by formula (IIB), or an N-oxide thereof, or a pharmaceutically acceptable salt or solvate thereof, or a glucuronide derivative thereof, or a co-crystal thereof,

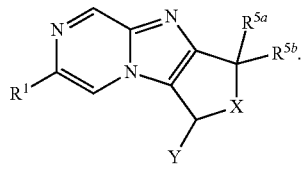

(IIB)

6. The compound according to claim 5 represented by formula (IIB-AB), or an N-oxide thereof, or a pharmaceutically acceptable salt or solvate thereof, or a glucuronide derivative thereof, or a co-crystal thereof,

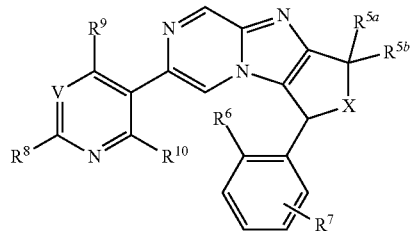

(IIB-AB)

wherein
V represents C—$R^{11}$ or N;
$R^6$ represents hydrogen, halogen, $C_{1-6}$ alkyl, trifluoromethyl, $C_{1-6}$ alkoxy, difluoromethoxy or trifluoromethoxy;
$R^7$ represents hydrogen, halogen, cyano, $C_{1-6}$ alkyl, trifluoromethyl, difluoromethoxy or amino;
$R^8$ represents hydroxy, $C_{1-6}$ alkoxy, $(C_{3-7})$heterocycloalkyl, or (hydroxy)$C_{1-6}$alkyl; and
$R^9$, $R^{10}$ and $R^{11}$ independently represent hydrogen.

7. The compound according to claim 5, wherein X represents a methylene group.

8. The compound as claimed in claim 1 selected from the group consisting of
1-[2-(difluoromethoxy)phenyl]-8-(6-methoxypyridin-3-yl)-3,4-dihydro-1H-pyrano[4',3':4,5]imidazo[1,2-a]pyrazine;
1-[2-(difluoromethoxy)phenyl]-8-[2-(morpholin-4-yl)pyrimidin-5-yl]-3,4-dihydro-1H-pyrano[4',3':4,5]imidazo[1,2-a]pyrazine;
5-{1-[2-(difluoromethoxy)phenyl]-3,4-dihydro-1H-pyrano[4',3':4,5]imidazo[1,2-a]pyrazin-8-yl}pyridin-2(1H)-one;
(1S)-8-bromo-1-[2-(difluoromethoxy)phenyl]-3,4-dihydro-1H-pyrano[4',3':4,5]imidazo[1,2-a]pyrazine;
(1R)-8-bromo-1-[2-(difluoromethoxy)phenyl]-3,4-dihydro-1H-pyrano[4',3':4,5]imidazo[1,2-a]pyrazine;
(6R,8R)-8-[5-chloro-2-(difluoromethoxy)phenyl]-2-[6-(1-hydroxy-1-methyl-ethyl)-3-pyridyl]-7,8-dihydro-6H-cyclopenta[1,2]imidazo[3,4-b]pyrazin-6-ol;
(6S,8S)-8-[5-chloro-2-(difluoromethoxy)phenyl]-2-[6-(1-hydroxy-1-methyl-ethyl)-3-pyridyl]-7,8-dihydro-6H-cyclopenta[1,2]imidazo[3,4-b]pyrazin-6-ol,
2-[[(6R,8R)-8-[5-chloro-2-(difluoromethoxy)phenyl]-2-[6-(1-hydroxy-1-methyl-ethyl)-3-pyridyl]-7,8-dihydro-6H-cyclopenta[1,2]imidazo[3,4-b]pyrazin-6-yl]oxy]acetamide; and
2-[[(6S,8S)-8-[5-chloro-2-(difluoromethoxy)phenyl]-2-[6-(1-hydroxy-1-methyl-ethyl)-3-pyridyl]-7,8-dihydro-6H-cyclopenta[1,2]imidazo[3,4-b]pyrazin-6-yl]oxy]acetamide.

9. A pharmaceutical composition comprising a compound of formula (I) as claimed in claim 1 or an N-oxide thereof, or a pharmaceutically acceptable salt thereof, in association with a pharmaceutically acceptable carrier.

10. A method for the treatment of disorders for which the administration of an inhibitor of TNFα function is indicated which comprises administering to a patient in need of such treatment an effective amount of a compound of formula (I) as defined in claim 1, or an N-oxide thereof, or a pharmaceutically acceptable salt thereof.

11. A method according to claim 10 wherein the disorder is an inflammatory or autoimmune disorder, a neurological disorder, pain, a cardiovascular disorder, a metabolic disorder, an ocular disorder, or an oncological disorder.

* * * * *